US007825095B2

(12) United States Patent
Speirs et al.

(10) Patent No.: US 7,825,095 B2
(45) Date of Patent: *Nov. 2, 2010

(54) METHODS AND UNIT DOSE FORMULATIONS FOR THE INHALATION ADMINISTRATION OF AMINOGLYCOSIDE ANTIBIOTICS

(75) Inventors: Robert John Speirs, Mountlake Terrace, WA (US); Barbara Ann Schaeffler, Seattle, WA (US); Peter Bruce Challoner, Seattle, WA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 160 days.

This patent is subject to a terminal disclaimer.

(21) Appl. No.: 11/923,486

(22) Filed: Oct. 24, 2007

(65) Prior Publication Data

US 2008/0095717 A1 Apr. 24, 2008

Related U.S. Application Data

(63) Continuation of application No. 11/125,670, filed on May 10, 2005, now abandoned, which is a continuation of application No. 10/743,529, filed on Dec. 22, 2003, now Pat. No. 6,890,907, which is a continuation of application No. 10/151,701, filed on May 17, 2002, now abandoned.

(60) Provisional application No. 60/292,234, filed on May 18, 2001.

(51) Int. Cl.
*A61K 31/70* (2006.01)
*A61K 31/175* (2006.01)
*A01N 25/00* (2006.01)

(52) U.S. Cl. .......................... 514/38; 514/851; 514/958

(58) Field of Classification Search .................. 514/38, 514/851, 958
See application file for complete search history.

(56) References Cited

U.S. PATENT DOCUMENTS

| 5,508,269 | A  | 4/1996 | Smith |
| 5,758,637 | A  | 6/1998 | Ivri |
| 6,083,922 | A  | 7/2000 | Montgomery |
| 6,387,886 | B1 | 5/2002 | Montgomery |
| 6,890,907 | B2 | 5/2005 | Speirs |

FOREIGN PATENT DOCUMENTS

| WO | 9843650 A1 | 10/1998 |
| WO | 0035461 A1 | 6/2000 |
| WO | 0134232 A1 | 5/2001 |

OTHER PUBLICATIONS

Aerogen Inc. SEC Form 10-K, 2000.
* AeroGen's Annual Report 2000.

Coates, A.L., et al., "The Choice of Jet Nebulizer, Nebulizing Flow, and Addition of Albuterol Affects the Output of Tobramycin Aerosols," Chest 111(5):1206-1212, 1997.
Cooney, G.F., et al., "Absolute Bioavailability and Absorption Characteristics of Aerosolized Tobramycin in Adults With Cystic Fibrosis," Clin. Pharmacol. 34:255-259, 1994.
* Cystic L web page.
* De Young, L.R., et al., "The Aerodose Multidose Inhaler Device Design and Delivery Characteristics," Proceedings of Respiratory Drug Delivery VI, Hilton Head, S.C., Apr. 1998, pp. 91-95.
Durrani, F.K., et al., "Evaluation of a New, Shorter Method of Administration of Adrenergic Aerosols in the Treatment of Asthma," Annals of Allergy 61:147-150, 1988.
* Eisenberg, J., et al., "A Comparison of Peak Sputum Tobramycin Concentration in Patients With Cystic Fibrosis Using Jet and Ultrasonic Nebulizer Systems," Chest 111(4):955-962, 1997.
Faurisson, F., et al., "Étude Comparative sur les Performances et l'Ergonomie de Nébuliseurs dans la Mucoviscidose," Rev. Mal. Resp. 13:155-162, 1996.
Geller, D.E., et al., "Efficiency of Pulmonary Administration of Tobramycin Solution for Inhalation in Cystic Fibrosis Using an Improved Drug Delivery System," Chest 123:28-36, 2003.
* Gopalakrishnan, V., and W. Xia, "Aerodose™ Inhaler: Effect of Formulation Physicochemical Properties on Aerosol Attributes," Proceedings of Respiratory Drug Delivery VII, Tarpon Springs, Fla., May 14-18, 2000, pp. 299-301.
* Gopalakrishnan,V., et al., "Aerodose™ Inhaler: Comparison of In Vitro Particle Size Data, Computer Modeled and Scintigraphic Lung Deposition Profiles," Proceedings of Respiratory Drug Delivery VII, Tarpon Springs, Fla., May 14-18, 2000, pp. 303-306.
Ho, S.L., and A.L. Coates, "Effect of Dead Volume on the Efficiency and the Cost to Deliver Medications in Cystic Fibrosis With Four Disposable Nebulizers," Can. Respir. J. 6(3):253-260, 1999.
* Hüls, G., et al., "Pilot Study on Toleration of Inhalation With a New High Concentrated Tobramycin Solution Using an Improved Nebulizer," Netherlands Journal of Medicine 54:S37-S38, 1999.
Kendrick, A.H., et al., "Selecting and Using Nebuliser Equipment," Thorax 52(Suppl 2):S92-S101, 1997.
* Le Brun, P.P.H., et al., "Inhalation of Tobramycin in Cystic Fibrosis / Part 2: Optimization of the Tobramycin Solution for a Jet and an Ultrasonic Nebulizer," International Journal of Pharmaceutics 189:215-225, 1999.

(Continued)

*Primary Examiner*—James O Wilson
*Assistant Examiner*—Ebenezer Sackey
(74) *Attorney, Agent, or Firm*—Cozette M McAvoy

(57) ABSTRACT

A patient suffering from an endobronchial infection is treated by administering to the patient for inhalation a dose of less than about 4.0 ml of a nebulized aerosol formulation comprising from about 60 to about 200 mg/ml of an aminoglycoside antibiotic, such as tobramycin, in a physiologically acceptable carrier in a time period of less than about 10 minutes. Unit dose devices for storage and delivery of the aminoglycoside antibiotic formulations are also provided.

16 Claims, 8 Drawing Sheets

OTHER PUBLICATIONS

Le Conte, P., et al., "Lung Distribution and Pharmacokinetics of Aerosolized Tobramycin," Am. Rev. Respir. Dis. 147:1279-1282, 1993.

Littlewood, J.M. et al., "Aerosol Antibiotic Treatment in Cystic Fibrosis," Archives of Disease in Childhood 68:788-792, 1993.

* Luangkhot, N., et al., "Characterisation of Salbutamol Solution Compared to Budesonide Suspensions Consisting of Submicron and Micrometer Particles in the PARI LC STAR and a New PARI Electronic Nebuliser (e-FLOW)," Proceedings of Drug Delivery to the Lungs XI, London, Dec. 11-12, 2000.

MacLusky, I.B., et al., "Long-Term Effects of Inhaled Tobramycin in Patients With Cystic Fibrosis Colonized With Pseudomonas aeruginosa," Pediatric Pulmonology 7:42-48, 1989.

Makhoul, I. R., et al., "Antibiotic Treatment of Experimental Pseudomonas aeruginosa Pneumonia in Guinea Pigs: Comparison of Aerosol and Systemic Administration," J. Infectious Diseases 168:1296-1299, 1993.

Nikolaizik, W.H., et al., "Bronchial Constriction After Nebulized Tobramycin Preparations and Saline in Patients With Cystic Fibrosis," Eur. J. Pediatrics 155:608-611, 1996.

* Notice of Opposition, related EP Patent No. 1 320 355, Jan. 5, 2007.
* Pathogenesis Annual Report of 1999.
* "PathoGenesis Begins Clinical Trial of TOBI and AeroGen's Hand-Held AeroDose™ Inhaler," PR Newswire, Jul. 11, 2000, <http://www.prnewswire.com> [retrieved Nov. 24, 2006].

"PathoGenesis Inks Deal With AeroGen," Puget Sound Business Journal, © 2000 American City Business Journals Inc., <http://seattle.bizjournals.com/seattle/stories/2000/02/daily15.html> [retrieved Apr. 15, 2004].

Pathogenesis Corporation SEC Form 10-K, 1999.

Ramsey, B.W., et al., "Efficacy of Aerosolized Tobramycin in Patients With Cystic Fibrosis,"New England J. Med. 328:1740-1746, 1993.

* Ramsey, B.W., et al., "Intermittent Administration of Inhaled Tobramycin in Patients With Cystic Fibrosis," New England J. Med. 340(1):23-30, 1999.

* Seitz, D.J., et al., "Stability of Tobramycin Sulfate in Plastic Syringes," American Journal of Health System Pharmacy 37:1614-1615, 1980.

* Simon, M., and V. Gopalakrishnan, "Aerodose™ Inhaler-Aerosol Characteristics of a Systemic and a Respiratory Drug," Proceedings of Respiratory Drug Delivery VII, Tarpon Springs, Fla., May 14-18, 2000, pp. 307-309.

Smith, A.L., et al., "Safety of Aerosol Tobramycin Administration for 3 Months to Patients With Cystic Fibrosis," Pediatric Pulmonology 7:265-271, 1989.

Standaert, T.A., et al., "The Choice of Compressor Effects the Aerosol Parameters and the Delivery of Tobramycin From a Single Model Nebulizer," J. Aerosol Medicine 13(2):147-153, 2000.

* Stangl, R., et al., "Characterising the First Prototype of a Vibrating Membrane Nebuliser," Proceedings of Respiratory Drug Delivery VII, Tarpon Springs, Fla., May 2000.

* Stangl, R., et al., "Characterising the Functional Model of a Vibrating Membrane Nebuliser," Proceedings of Drug Delivery to the Lungs X, London, Dec. 2-3, 1999, pp. 1-4.

* Stangl, R., et al., "Estimating the Efficiency of a Vibrating Membrane Nebuliser," Proceedings of Drug Delivery to the Lungs XI, London, Dec. 11-12, 2000.

Steinkamp, G., et al., "Long-Term Tobramycin Aerosol Therapy in Cystic Fibrosis," Pediatric Pulmonology 6:91-98, 1989.

"TOBI® Tobramycin Solution for Inhalation," Prescribing Information, CHIRON Corporation, Emeryville, Calif., Apr. 2001, 4 pp.

* TOBI Package Insert.

Touw, D.J., et al., "Pharmacokinetics of Aerosolized Tobramycin in Adult Patients With Cystic Fibrosis," Antimicrobial Agents and Chemotherapy 41:184-187, 1997.

Valcke, Y.J., and R.A. Pauwels, "Pharmocokinetic Evaluation of Tobramycin in the Alveolar Lining Fluid of the Rat After Endotracheal Administration," Am. Rev. Respir. Dis. 144:1199-1201, 1991.

* Webb, A.K., and M.E. Dodd, "Nebulised Antibiotics for Adults With Cystic Fibrosis," Thorax 57(Suppl. 2):S69-S71, 1997.

* Weber, A., et al., "Effect of Nebulizer Type and Antibiotic Concentration on Device Performance," Pediatric Pulmonology 23:249-260, 1997.

Weber, A., et al., "Nebulizer Delivery of Tobramycin to the Lower Respiratory Tract," Pediatric Pulmonology 17:331-339, 1994.

Weber, A., et al., "Tobramycin Serum Concentrations After Aerosol and Oral Administration in Cystic Fibrosis," Am. J. Therapeutics 2:81-87, 1995.

Notice of Intent to Issue Ex Parte Reexamination Certificate dated Jun. 24, 2008, and Reexamination Reasons for Patentability/Confirmation dated Jun. 19, 2008, issued in Reexamination Control No. 90/007,749, filed Oct. 17, 2005.

Decision Rejecting the Opposition dated Sep. 19, 2008, issued in European Patent No. 1320355.

Statement Setting out the Grounds of Appeal dated Jan. 28, 2009, filed in European Patent Appeal Case No. T2197/08-3.3.02 relating to European Patent No. 1320355.

Patentee's Response to the Grounds of Appeal dated Jun. 19, 2009, filed in Patent Appeal Case No. T2197108-3.3.02 relating to European Patent No. 1320355.

Todisco T et al., "Aerosol delivery of new 1-9 drugs in pneumology", European Respiratory Journal, vol. 8, Suppl. 19, p. 129S, XP009131708, Sep. 20, 1995.

American Health concultants inc: "Other news to note (brief article)", XP002588650, Database accession No. 2000:63867, Bioworld Today, vol. 11, No. 42, Mar. 3, 2000.

METHODS AND UNIT DOSE FORMULATIONS FOR THE INHALATION ADMINISTRATION OF AMINOGLYCOSIDE ANTIBIOTICS

CROSS-REFERENCE TO RELATED APPLICATIONS

This application is a continuation of application Ser. No. 11/125,670, filed May 10, 2005, which is a continuation of application Ser. No. 10/743,529, filed Dec. 22, 2003 (now U.S. Pat. No. 6,890,907), which is a continuation of application Ser. No. 10/151,701, filed May 17, 2002 (now abandoned), which claims the benefit of Provisional Application No. 60/292,234, filed May 18, 2001, the disclosures of which are incorporated by reference herein.

FIELD OF THE INVENTION

The present invention relates to new and improved unit dose containers of aminoglycoside antibiotics, such as tobramycin, for delivery by aerosol inhalation, and to improved methods of treatment of susceptible acute or chronic endobronchial infections.

BACKGROUND OF THE INVENTION

Progressive pulmonary disease is the cause of death in over 90% of cystic fibrosis (CF) patients (Koch C. et al., "Pathogenesis of cystic fibrosis," *Lancet* 341(8852):1065-9 (1993); Konstan M. W. et al., "Infection and inflammation of the lung in cystic fibrosis," Davis P B, ed., *Lung Biology in Health and Disease, Vol.* 64. New York, N.Y.: Dekker: 219-76 (1993)). *Pseudomonas aeruginosa* is the most significant pathogen in CF lung disease. Over 80% of CF patients eventually become colonized with *P. aeruginosa* (Fitzsimmons S. C., "The changing epidemiology of cystic fibrosis," *J Pediatr* 122(1): 1-9 (1993)). The standard therapy for *P. aeruginosa* endobronchial infections is 14 to 21 days of parenteral antipseudomonal antibiotics, typically including an aminoglycoside. However, parenteral aminoglycosides, as highly polar agents, penetrate poorly into the endobronchial space. To obtain adequate drug concentrations at the site of infection with parenteral administration, serum levels approaching those associated with nephro-, vestibulo-, and oto-toxicity are required ("American Academy of Otolaryngology. Guide for the evaluation of hearing handicap," *JAMA* 241(19):2055-9 (1979); Brummett R. E., "Drug-induced ototoxicity," *Drugs* 19:412-28 (1980)).

Aerosolized administration of aminoglycosides offers an attractive alternative, delivering high concentrations of antibiotic directly to the site of infection in the endobronchial space while minimizing systemic bioavailability (Touw D. J. et al., "Inhalation of antibiotics in cystic fibrosis," *Eur Respir J* 8:1594-604 (1995); Rosenfeld M. et al., "Aerosolized antibiotics for bacterial lower airway infections: principles, efficacy, and pitfalls," *Clinical Pulmonary Medicine* 4(2): 101-12 (1997)).

Tobramycin is commonly prescribed for the treatment of serious *P. aeruginosa* infections. It is an aminoglycoside antibiotic produced by the actinomycete, *Streptomyces tenebrarius*. Low concentrations of tobramycin (<4 µg/mL) are effective in inhibiting the growth of many Gram-negative bacteria and under certain conditions may be bactericidal (Neu, H. C., "Tobramycin: an overview," *J Infect Dis* 134, Suppl: S3-19 (1976)). Tobramycin is poorly absorbed across mucosal surfaces, conventionally necessitating parenteral administration. Tobramycin activity is inhibited by purulent sputum: high concentrations of divalent cations, acidic conditions, increased ionic strength and macromolecules that bind the drug all inhibit tobramycin in this environment. It is estimated that 5 to 10 times higher concentrations of tobramycin are required in the sputum to overcome these inhibitory effects (Levy J. et al., "Bioactivity of gentamicin in purulent sputum from patients with cystic fibrosis or bronchiectasis: comparison with activity in serum," *J Infect Dis* 148(6):1069-76 (1983)).

Delivery of the poorly absorbed antibiotic tobramycin to the airway by the aerosol route of cystic fibrosis (CF) patients has been documented using the aerosol route. Much of this work has been done toward treatment of chronic lung infections with *P. aeruginosa* in cystic fibrosis (CF) patients. A multicenter, double blind, placebo-controlled, crossover trial of 600 mg tid of aerosolized tobramycin for endobronchial infections due to *P. aeruginosa* in 71 CF patients demonstrated a significant reduction in sputum density of this pathogen as well as improved spirometry in the treatment group. Emergence of *P. aeruginosa* strains highly resistant to tobramycin (defined as MIC≧128 µg/mL) was comparable in the placebo and treatment groups. The presence in the sputum of Gram-negative organisms other than *P. aeruginosa* intrinsically resistant to tobramycin occurred with equal frequency during administration of tobramycin or placebo (Ramsey B. et al., "Response to Letter to the Editor: Aerosolized tobramycin in patients with cystic fibrosis," *N Engl J Med* 329: 1660 (1993)).

Although this regimen was found to be both safe and efficacious, it is costly and inconvenient. A survey of the MICs for *P. aeruginosa* isolates from initial sputum cultures for patients at the Children's Hospital CF Center, Seattle, Wash., in 1993 found that 90% of isolates had MICs≦16 µg/mL and 98% of all isolates had MICs≦128 µg/mL. This survey suggested that achieving a sputum tobramycin concentration of 128 µg/mL should treat the endobronchial infection in CF patients (Levy J. et al., "Bioactivity of gentamicin in purulent sputum from patients with cystic fibrosis or bronchiectasis: comparison with activity in serum," *J Infect Dis* 148(6):1069-76 (1983)).

A randomized, crossover study compared the ability of several nebulizers to deliver tobramycin by measuring peak sputum tobramycin concentrations in samples collected ten minutes after completion of the aerosol dose. This study administered TOBI® tobramycin solution for inhalation, PathoGenesis Corporation, Seattle, Wash. (now Chiron Corporation, Emeryville, Calif.), containing 60 mg/mL tobramycin in 5 mL one quarter (¼) normal saline, using the Pari® LC jet nebulizer, Pari Respiratory Equipment, Inc., Richmond, Va. This delivery system was shown to deliver a mean peak sputum tobramycin concentration of 678.8 µg/g (s.d. 661.0 µg/g), and a median peak sputum concentration of 433.0 µg/g. Only 13% of patients had sputum levels ≦128 µg/g; 87% of patients achieved sputum levels of ≧128 µg/g (Eisenberg, J. et al., "A Comparison of Peak Sputum Tobramycin Concentration in Patients With Cystic Fibrosis Using Jet and Ultrasonic Nebulizer Systems. Aerosolized Tobramycin Study Group," *Chest* 111(4):955-962 (1997)). Recently, the Pari® LC jet nebulizer has been modified with the addition of one-way flow valves, and renamed the Pari® LC PLUS. The one-way valves in the Pari® LC PLUS have been described as permitting the delivery of more drug than the Pari® LC jet nebulizer, while decreasing the potential for accidental spillage and allowing for the use of an expiratory filter. Experience has shown that mean peak sputum tobramycin concentrations achieved using the Pari LC PLUS jet nebulizer are significantly higher than those using the Pari® LC jet nebulizer as described in Eisenberg et al. (1997), supra.

Two placebo-controlled, multicenter, randomized, double blind clinical trials of intermittent administration of inhaled tobramycin in cystic fibrosis patients with *P. aeruginosa* infection were reported in Ramsey, B. W. et al., "Intermittent Administration of Inhaled Tobramycin in Patients with Cystic Fibrosis. Cystic Fibrosis Inhaled Tobramycin Study Group." N. Engl. J. Med. 340(1):23-30 (1999). In these studies, five hundred twenty subjects were randomized to receive either 300 mg inhaled tobramycin or placebo twice daily for 28 days followed by 28 days off study drug. Subjects continued on treatment or placebo for three "on-off" cycles for a total of 24 weeks. Efficacy variables included sputum *P. aeruginosa* density. Tobramycin-treated patients had an average 0.8 $\log_{10}$ decrease in *P. aeruginosa* density from Week 0 to Week 20, compared with a 0.3 $\log_{10}$ increase in placebo-treated patients (P<0.001). Tobramycin-treated patients had an average 1.9 $\log_{10}$ decrease in *P. aeruginosa* density from Week 0 to Week 4, compared with no change in placebo-treated patients (P<0.001).

A preservative-free, stable, and convenient formulation of tobramycin (TOBI®) tobramycin solution for inhalation; 60 mg/mL tobramycin in 5 mL of ¼ normal saline) for administration via jet nebulizer was developed by PathoGenesis Corporation, Seattle, Wash. (now Chiron Corporation, Emeryville, Calif.). The combination of a 5 mL BID TOBI dose (300 mg tobramycin) and the PARI LC PLUS/PulmoAide compressor delivery system was approved under NDA 50-753, December 1997, for the management of *P. aeruginosa* in CF patients, and remains the industry standard for this purpose. The aerosol administration of a 5 ml dose of a formulation containing 300 mg of tobramycin in quarter normal saline for the suppression of *P. aeruginosa* in the endobronchial space of a patient is disclosed in U.S. Pat. No. 5,508,269, the disclosure of which is incorporated herein in its entirety by this reference.

Although the current conventional delivery systems have been shown to be clinically efficacious, they typically suffer from relatively low efficiency levels in delivering antibiotic solutions to the endobronchial space of a patient, thereby wasting a substantial portion of the nebulized antibiotic formulations and substantially increasing drug delivery costs. The low efficiency of current conventional delivery systems requires patients to devote relatively long time periods to receive an effective dose of the nebulized antibiotic formulations, which can lead to decreased patient compliance. Accordingly, there is a need for new and improved methods and devices for the delivery of aminoglycoside antibiotic compounds to a patient by inhalation to reduce administration costs, increase patient compliance and enhance overall effectiveness of the inhalation therapy.

SUMMARY OF THE INVENTION

It has now been discovered that patients suffering from an endobronchial infection can be effectively and efficiently treated by administering to the patient for inhalation a dose of less than about 4.0 ml of a nebulized aerosol formulation comprising from about 60 to about 200 mg/ml of an aminoglycoside antibiotic, such as tobramycin, in a physiologically acceptable carrier in a time period of less than about 10 minutes, more preferably less than about 8 minutes, and even more preferably less than about 6 minutes. In other aspects, the administered dose may be less than about 3.75 ml or 3.5 ml or less, and the aminoglycoside antibiotic formulation may comprise from about 80 to about 180 mg/ml of aminoglycoside antibiotic or more preferably from about 90 to about 150 mg/ml of aminoglycoside antibiotic.

In other aspects, the present invention provides unit dose formulations and devices adapted for use in connection with a high efficiency inhalation system, the unit dose device comprising a container designed to hold and store the relatively small volumes of the aminoglycoside antibiotic formulations of the invention, and to deliver the formulations to an inhalation device for delivery to a patient in aerosol form. In one aspect, a unit dose device of the invention comprises a sealed container, such as an ampoule, containing less than about 4.0 ml of an aminoglycoside antibiotic formulation comprising from about 60 to about 200 mg/ml of an aminoglycoside antibiotic in a physiologically acceptable carrier. The sealed container is preferably adapted to deliver the aminoglycoside antibiotic formulation to a high efficiency inhalation device for aerosolization and inhalation by a patient. In other aspects, the container of the unit dose device may contain less than about 3.75 ml, or 3.5 ml or less, of the aminoglycoside antibiotic formulation, and the aminoglycoside antibiotic formulation may comprise from about 80 to about 180 mg/ml, or from about 90 to about 120 mg/ml, of aminoglycoside antibiotic.

In yet other aspects, the present invention relates to a system for delivering an aminoglycoside antibiotic formulation to a patient in need of such treatment, comprising a unit dose device as described in detail above, comprising a container containing less than about 4.0 ml of an aminoglycoside antibiotic formulation comprising from about 60 to about 200 mg/ml of an aminoglycoside antibiotic in a physiologically acceptable carrier, and means for delivering the aminoglycoside antibiotic formulation from the unit dose device for inhalation by the patient in aerosolized form in less that 10 about minutes.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 is a graphical representation illustrating the mean relative changes in $FEV_1$% predicted from before to 30 minutes after dosing with 300 mg tobramycin with a PARI LC PLUS jet nebulizer/PulmoAide compressor delivery system, or with 30, 60, or 90 mg tobramycin with an Aerodose breath actuated nebulizer, as described in Example 1;

FIG. 2 is a graphical representation showing sputum tobramycin concentrations by time from dosing by the tobramycin formulations of FIG. 1, as described in Example 1;

FIG. 3 is a graphical representation showing sputum maximum plasma concentrations ($C_{max}$) following dosing by the tobramycin formulations of FIG. 1, as described in Example 1;

FIG. 4 is a graphical representation showing sputum area under the plasma concentration time profile ($AUC_{0-8}$) following dosing by the tobramycin formulations of FIG. 1, as described in Example 1;

FIG. 5 is a graphical representation showing serum tobramycin concentrations by time following dosing by the tobramycin formulations of FIG. 1, as described in Example 1;

FIG. 6 is a graphical representation showing serum maximum plasma concentrations ($C_{max}$) following dosing by the tobramycin formulations of FIG. 1, as described in Example 1;

FIG. 7 is a graphical representation showing serum area under the plasma concentration time profile ($AUC_{0-8}$) following dosing by the tobramycin formulations of FIG. 1, as described in Example 1;

DETAILED DESCRIPTION OF PREFERRED EMBODIMENTS

Figure 1:
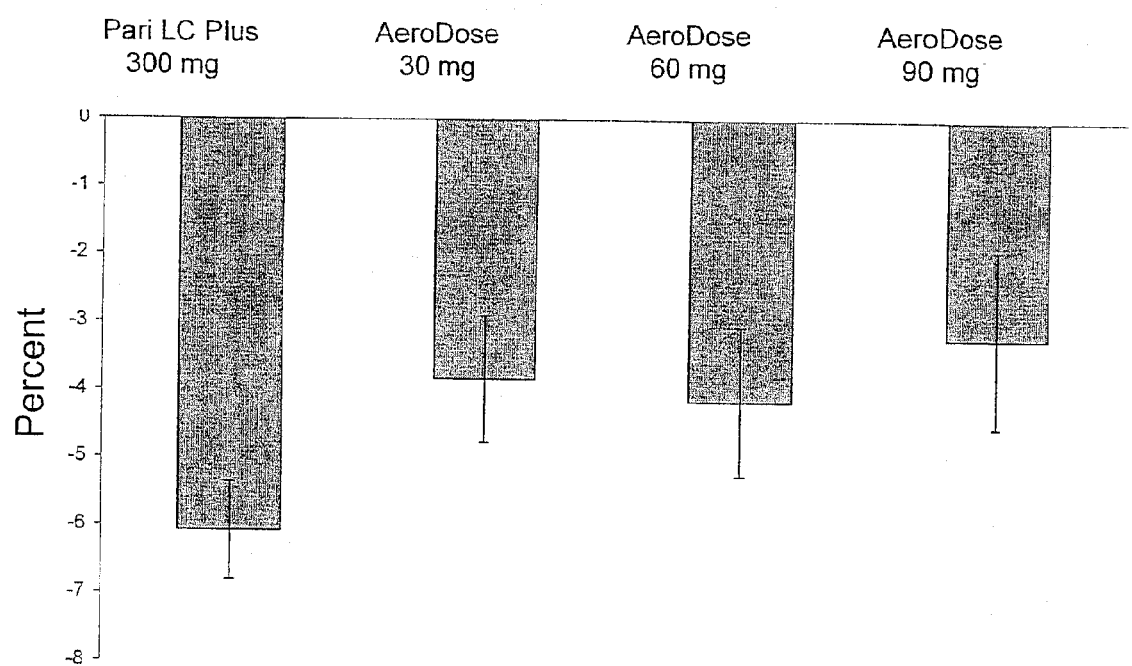

In accordance with the present invention, methods are provided for the treatment of a patient in need of treatment, such as a patient suffering from an endobronchial *P. aeruginosa* infection, comprising administering to the patient for inhalation a relatively small volume of an aminoglycoside antibiotic formulation over a relatively short period of time. This aspect of the invention is particularly suitable for formulation of concentrated aminoglycosides, such as tobramycin, for aerosolization by small volume, breath actuated, high output rate and high efficiency inhalers to produce a aminoglycoside aerosol particle size between 1 and 5 µm desirable for efficacious delivery of the aminoglycoside into the endobronchial space to treat susceptible microbial infections, such as *Pseudomonas aeruginosa* infections. The formulations preferably contains minimal yet efficacious amount of aminoglycoside formulated in smallest practical volume of a physiologically acceptable solution, for example an aqueous solution having a salinity adjusted to permit generation of aminoglycoside aerosol particles that are well-tolerated by patients but preventing the development of secondary undesirable side effects such as bronchospasm and cough. By the more efficient administration of the aminoglycoside formulation provided by the present invention, substantially smaller volumes of aminoglycoside than the conventional administration regime are administered in substantially shorter periods of time, thereby reducing the costs of administration and drug waste, and significantly enhancing the likelihood of patient compliance.

Thus, in accordance with one aspect of the present invention, methods are provided for the treatment of a patient in need of treatment, such as a patient suffering from an endobronchial *P. aeruginosa* infection, comprising administering to the patient for inhalation a dose of less than about 4.0 ml of a nebulized aerosol formulation comprising from about 60 to about 200 mg/ml of an aminoglycoside antibiotic in a time period of less than about 10 minutes. In other aspects, the dose of the aerosol formulation is administered to the patient in less than about 8 minutes. In yet other aspects, the dose of the aerosol formulation is administered to the patient in less than about 6 minutes.

The aerosol formulations administered in the practice of the invention may comprise from about 60 to about 200 mg/ml of aminoglycoside antibiotic. In other aspects of the invention, the aerosol formulations administered in the practice of the invention may comprise from about 80 to about 180 mg/ml of aminoglycoside antibiotic. In yet other aspects of the invention, the aerosol formulations administered in the practice of the invention may comprise from about 90 to about 150 mg/ml of aminoglycoside antibiotic.

In the practice of the methods of the invention, substantially smaller volumes of aerosol formulation are administered to the patient, as compared with the conventional administration processes. Thus, in one aspect a dose of less than about 4.0 ml of a nebulized aerosol formulation is administered to the patient. In another aspect, a dose of less than about 3.75 ml of a nebulized aerosol formulation is administered to the patient. In yet another aspect, a dose of 3.5 ml or less of a nebulized aerosol formulation is administered to the patient. In one aspect a dose of less than about 2.0 ml of a nebulized aerosol formulation is administered to the patient. In another aspect, a dose of less than about 1.5 ml of a nebulized aerosol formulation is administered to the patient. In yet another aspect, a dose of less than about 1.0 ml of a nebulized aerosol formulation is administered to the patient.

In yet other aspects, the present invention relates to a system for delivering an aminoglycoside antibiotic formulation to a patient in need of such treatment, comprising a unit dose device as described in detail herein, comprising a container containing less than about 4.0 ml of an aminoglycoside antibiotic formulation comprising from about 60 to about 200 mg/ml of an aminoglycoside antibiotic in a physiologically acceptable carrier, and means for delivering the aminoglycoside antibiotic formulation from the unit dose device for inhalation by the patient in aerosolized form in less that 10 about minutes.

In order to deliver the relatively small volumes of the relatively high concentration aminoglycoside antibiotic formulations to the patient for inhalation in the relatively short dosing periods of the invention, the antibiotic formulations are preferably administered with the use of an inhalation device having a relatively high rate of aerosol output. Useful devices may also exhibit high emitted dose efficiency (i.e., low residual volume in the device). In order to increase the overall efficiency of the system, emission may additionally be limited to periods of actual inhalation by the patient (i.e., breath actuated). Thus, while conventional air-jet nebulizers exhibit a rate of aerosol output on the order of 3 µl/sec, inhalation devices useful for use in the practice of the present invention will typically exhibit a rate of aerosol output of not less that about 4 µl/sec. In some cases, inhalation devices useful for use in the practice of the present invention will exhibit a rate of aerosol output of not less than about 5 µl/sec or even not less than about 8 µl/sec. In addition, while conventional air-jet nebulizers have a relatively low emitted dose efficiency and typically release about 55% (or less) of the nominal dose as aerosol, inhalation devices useful for use in the practice of the present invention may release at least about 75%, more preferably at least about 80% and most preferably at least about 85% of the loaded dose as aerosol for inhalation by the patient. In other aspects, conventional air-jet nebulizers typically continually release aerosolized drug throughout the delivery period, without regard to whether the patient is inhaling, exhaling or in a static portion of the breathing cycle, thereby wasting a substantial portion of the loaded drug dose. In some embodiments, inhalation devices for use in the present invention will be breath actuated, and restricted to delivery of aerosolized particles of the aminoglycoside formulation to the period of actual inhalation by the patient. One representative inhalation device meeting the above criteria and suitable for use in the practice of the invention is the Aerodose™ inhaler, available from Aerogen, Inc., Sunnyvale, Calif. The Aerodose™ inhaler generates an aerosol using a porous membrane driven by a piezoelectric oscillator. Aerosol delivery is breath actuated, and restricted to the inhalation phase of the breath cycle, i.e., aerosolization does not occur during the exhalation phase of the breath cycle. The airflow path design allows normal inhale-exhale breathing, compared to breath-hold inhalers. Additionally, the Aerodose™ inhaler is a hand-held, self-contained, and easily transported inhaler. Although piezoelectric oscillator aerosol generators, such as the Aerodose™ inhaler, represent one embodiment for use in the practice of the invention, other inhaler or nebulizer devices may be employed that meet the above performance criteria and are capable of delivering the small dosage volumes of the invention with a relative high effective deposition rate in a comparatively short period of time. In other embodiments of the invention devices useful for delivering the concentrated aminoglycoside formulations of the invention include conventional air-jet nebulizers coupled with a compressor capable of higher than conventional output pressures. Enhanced compressor output pressures useful in the practice of the invention will be readily determinable to those skilled in the art in view of the disclosure contained herein. As one representative example, the PARI LC PLUS™ jet nebulizer, PARI GmbH, Stamberg, Germany, driven by a Invacare MOBILAIRE™ compressor, Invacare Corporation, Elyria, Ohio, set for an output pressure of about 35 psi has been found to be capable of delivering 3.5 ml of the concentrated aerosolized aminoglycoside formulations of the invention (such as tobramycin) in 10 minutes or less, as is hereinafter described in detail in Example 3.

Aminoglycoside antibiotics useful in the practice of the invention include, for example, gentamicin, amikacin, kanamycin, streptomycin, neomycin, netilmicin and tobramycin. A presently particularly preferred aminoglycoside antibiotic for this purpose is tobramycin. Formulations according to the invention typically contain from about 60 to about 200 mg, more preferably from about 80 to about 180, and most preferably from about 90 to about 120 mg of aminoglycoside per ml of solution. The aminoglycoside antibiotic of the invention may be incorporated into sterile water or physiologically acceptable solution. Other components may be included in the formulation, as desired. In order to facilitate administration and compatibility with the endobronchial space, the aminoglycoside antibiotic of the invention is preferably formulated in a diluted physiological saline solution, such as in one quarter strength of normal saline, having a salinity adjusted to permit generation of tobramycin aerosol well-tolerated by patients but to prevent the development of secondary undesirable side effects such as bronchospasm and cough. Typically, about 90 to about 120 mg of aminoglycoside antibiotic is dissolved in 1 ml solution of a diluted, typically quarter normal saline containing about 0.225% NaCl. Quarter normal saline, that is 0.225% of sodium chloride, is a presently preferred vehicle for delivery of aminoglycoside into endobronchial space.

By way of illustration, high concentrations of tobramycin administered to the lungs by aerosolization result in maximization of sputum levels of tobramycin and in minimization of tobramycin serum levels. Thus, administration of tobramycin by aerosolization has the advantage of reducing systemic toxicity while providing efficacious concentrations of tobramycin in the sputum. The bronchial barrier restricts the movement of aerosolized tobramycin and prevents it from reaching high systemic levels.

In other aspects of the present invention, unit dose formulations and devices are provided for administration of an aminoglycoside antibiotic formulation to a patient with an inhaler, in accordance with the methods of the invention as described supra. Preferred unit dose devices comprise a container designed to hold and store the relatively small volumes of the aminoglycoside antibiotic formulations of the invention, and to deliver the formulations to an inhalation device for delivery to a patient in aerosol form. In one aspect, unit dose containers of the invention comprise a plastic ampoule filled with an aminoglycoside antibiotic formulation of the invention, and sealed under sterile conditions. Preferably, the unit dose ampoule is provided with a twist-off tab or other easy opening device for opening of the ampoule and delivery of the aminoglycoside antibiotic formulation to the inhalation device. Ampoules for containing drug formulations are well known to those skilled in the art (see, for example, U.S. Pat. Nos. 5,409,125, 5,379,898, 5,213,860, 5,046,627, 4,995,519, 4,979,630, 4,951,822, 4,502,616 and 3,993,223, the disclosures of which are incorporated herein by this reference). The unit dose containers of the invention may be designed to be inserted directly into an inhalation device of the invention for delivery of the contained aminoglycoside antibiotic formulation to the inhalation device and ultimately to the patient.

In accordance with this aspect of the invention, a unit dose device is provided comprising a sealed container containing less than about 4.0 ml of an aminoglycoside antibiotic formulation comprising from about 60 to about 200 mg/ml of an aminoglycoside antibiotic in a physiologically acceptable carrier, the sealed container being adapted to deliver the aminoglycoside antibiotic formulation to an inhalation device for aerosolization. Suitable aminoglycoside antibiotics for use in connection with this aspect of the invention include those aminoglycoside antibiotics described in detail, supra. In a presently preferred embodiment, the aminoglycoside antibiotic employed in the unit dose devices of the invention is tobramycin. In other aspects, the unit dose devices of the invention contain less than about 3.75 ml of the aminoglycoside solution. In other aspects, the unit dose devices of the invention contain 3.5 ml or less of the aminoglycoside solution.

In other aspects of the invention, the unit dose devices of the invention may contain an aminoglycoside antibiotic formulation comprising from about 80 to about 180 mg/ml of aminoglycoside antibiotic. In yet other aspects of the invention, the unit dose devices of the invention may contain an aminoglycoside antibiotic formulation comprising from about 90 to about 150 mg/ml of aminoglycoside antibiotic.

In preferred unit dose formulations of the invention, the physiologically acceptable carrier may comprise a physiological saline solution, such as a solution of one quarter strength of normal saline, having a salinity adjusted to permit generation of a tobramycin aerosol that is well-tolerated by patients, but that prevents the development of secondary undesirable side effects such as bronchospasm and cough.

These and other aspects of the inventive concepts may be better understood in connection with the following non-limiting examples.

EXAMPLES

Example 1

In Vivo Study 1

A comparison was made of the safety, pharmacokinetics, aerosol delivery characteristics, and nebulization time of the conventional dose and inhalation delivery system (5 mL ampoule containing 300 mg tobramycin and 11.25 mg sodium chloride in sterile water for injection (TOBI® tobramycin solution for inhalation, Chiron Corporation, Seattle, Wash.), pH 6.0; administered with a PARI LC PLUS™ jet nebulizer with a PulmoAide compressor) with 3 doses of TOBI (30 mg tobramycin in 0.5 mL solution, 60 mg in 1.0 mL, and 90 mg in 1.5 mL) using a AeroDose™ inhaler device.

The study was designed as an open label, randomized, multicenter, single dose, unbalanced, four treatment, three period crossover trial. Each patient was to receive three single doses of aerosolized antibiotic: the active drug control treatment during one treatment period and two of three experimental treatments during two additional treatment periods. Single dose administration during the three treatment periods was to occur at one-week intervals.

In accordance with the study design, forty eight eligible male and female patients 12 years of age or older with a confirmed diagnosis of cystic fibrosis were to be enrolled in the study and randomly assigned to one of 12 treatment sequences of three treatments each (one active control and two experimental treatments) with the constraint that the active control treatment was to be administered in either the first or the second of the three treatment periods. Experimental treatments were administered during all three treatment periods. Each patient inhaled a single dose of aerosolized control and two of three experimental treatments in accordance with the present invention as follows:
control delivery treatment (PARI LC PLUS jet nebulizer+ PulmoAide compressor):
TOBI 300 mg in 5 mL solution.
experimental delivery treatments (AeroDose™ inhaler breath actuated nebulizer):
TOBI 30 mg in 0.5 mL solution;
TOBI 60 mg in 1.0 mL solution;
TOBI 90 mg in 1.5 mL solution.

The duration of study participation for each patient was to be approximately five weeks including a brief (2 days to one week) screening period, three one-week treatment periods, and a one-week telephone follow-up period.

Control and Experimental Treatments

Each patient was to self-administer under research staff supervision a total of three single doses of aerosolized tobramycin during the study, one dose per crossover treatment period. Patients were to receive a single dose of the control delivery treatment during period 1 or period 2 of the three treatment periods. In addition, each patient was to receive single doses of two of the three experimental delivery treatments during the remaining two treatment periods. Control and experimental delivery treatments were specified as follows.

Control Delivery Treatment:
PARI LC PLUS jet nebulizer with PulmoAide compressor: preservative free tobramycin 60 mg/mL (excipient 5 mL of ¼ normal saline adjusted to a pH of 6.0±0.5); 300 mg in 5 mL.

Experimental Delivery Treatments:
Aerodose with a 3-4 µm mass medium diameter (MMD) aerosol particle size: preservative free tobramycin 60 mg/mL (excipient 0.5 mL of ¼ normal saline adjusted to a pH of 6.0±0.5); 30 mg in 0.5 mL;
Aerodose with a 3-4 µm MMD: preservative free tobramycin 60 mg/mL (excipient 1.0 mL of ¼ normal saline adjusted to a pH of 6.0±0.5); 60 mg in 1.0 mL;
Aerodose with a 3-4 µm MMD: preservative free tobramycin 60 mg/mL (excipient 1.5 mL of ¼ normal saline adjusted to a pH of 6.0±0.5); 90 mg in 1.5 mL.

Patients were placed upright in a sitting or standing position to promote normal breathing and were instructed to place the nose clips over the nostrils and to breath normally through the mouth until there was no longer any mist produced by the nebulizer. Aerosol delivery was anticipated to take 15 minutes to complete.

A pharmacist or coordinator prepared the 30 mg dose of TOBI by drawing 0.5 mL of the 60 mg/mL TOBI formulation into a one-mL syringe. Each syringe was labeled with the patient identification number. Study drug was dispensed into the medication reservoir as indicated in the Aerodose directions for use. TOBI 60 mg and 90 mg doses were similarly prepared by drawing two and three 0.5 mL aliquots, respectively, from the TOBI ampoule into two and three one-mL syringes.

Aerosol Delivery Systems

The control delivery system (PARI LC PLUS jet nebulizer) was used once per patient during the study for administration of TOBI 300 mg (control treatment). The experimental delivery system (Aerodose inhaler) was used to deliver only one dose of study treatments.

The control nebulizer, the PARI LC PLUS jet nebulizer with DeVilbiss PulmoAide compressor, generates aerosol by air-jet shear. A detailed comparison of experimental and control devices is provided in Table 1.

TABLE 1

| Device Characteristic | Aerodose Nebulizer | PARI LC PLUS Nebulizer and DeVilbiss PulmoAide Compressor |
|---|---|---|
| DEVICE COMPARISON | | |
| Aerosol generating principle | Piezoelectric vibration | Air-jet shear |
| Aerosol characteristics with TOBI | | |
| Mass median diameter (MMD) | 4.0 µm | 4.8 µm |
| Output rate | 8.0 µL/sec | 3.6 µL/sec |
| Emitted dose | 85% | 57% |
| Dose actuation | Breath-actuated by user inhalation | On/off switch; when on, medication aerosolized continuously |
| Control of aerosol generation | Breath actuated. An airflow sensor system is used to limit aerosol generation to inhalation | Continuous aerosol output during both inhalation and exhalation |
| User indicator lights | Green LED flashing for "device ready" and solid | None |

TABLE 1-continued

DEVICE COMPARISON

| Device Characteristic | Aerodose Nebulizer | PARI LC PLUS Nebulizer and DeVilbiss PulmoAide Compressor |
|---|---|---|
| | for "aerosolization" Red LED for "low battery" | |
| Physical characteristics | | |
| Size | 3.3" × 2.6" × 1.1" | 7.5" × 7.5" × 3.0" (nebulizer) 10.1" × 10.5" × 6.5" (compressor) |
| Weight | 140 gm | 68 gm (nebulizer) 3,200 gm (compressor) |
| Power source | Four AAA alkaline batteries | 115 VAC, 60 Hz |
| Power consumption | 2.5 watts | 90 watts (max.) |
| Where used | Fully portable | Restricted to power outlets supplying 115 VAC, 60 Hz |

Selection of Doses in the Study

Commercial TOBI 60 mg/mL in 5 mL solution administered by PARI LC PLUS jet nebulizer and powered by the PulmoAide compressor was the active drug control delivery system against which potential improvements in aerosol delivery technology by the Aerodose breath actuated nebulizer were compared in this example.

The selection of doses of experimental treatments (TOBI 30 mg in 0.5 mL solution, 60 mg in 1.0 mL, and 90 mg in 1.5 mL) was based on empirical data on the comparative predicted efficiency of the Aerodose inhaler relative to the PARI LC PLUS nebulizer. The selection of doses was also based on the assumption that TOBI delivered via the PARI LC PLUS jet nebulizer leads to the systemic absorption of approximately 11.7% of the administered dose {Pitlick, Nardella, et al., 1999}. Furthermore, the mean and standard deviation of the serum concentration one hour after inhalation was 1.0 µg/mL±0.58, suggesting a wide range of deposition (Table 5.2 C, Clinical Pharmacology, PathoGenesis NDA, #50,753). Due to design features of the Aerodose inhaler, it was estimated that between 50-70% of the drug would be delivered to the lung. This assumption is based on the predicted efficiency of a nebulized dose.

Patients were randomized to treatment sequence groups, and predose procedures were completed including a physical examination (only if abnormal during screening), recheck of inclusion and exclusion criteria, interim history review, spirometry, clinical evaluation, and blood and urine specimens for laboratory tests (only if abnormal during screening). A bronchodilator was to be administered before dosing if regularly used by the patient. Spirometry was completed 15-60 minutes after the bronchodilator, if applicable.

Patients received a single dose of study treatments during each of three treatment periods separated by an interval of 7 days between treatments. At the time of single dose administration during each period, patients were instructed to sit upright and use nose clips during aerosol dose administration.

Patients remained at the clinic through completion of 8-hour post treatment procedures (nebulization time, spirometry, and sputum, serum and urine specimens for tobramycin determinations). Patients were then discharged from the clinic and were expected to collect and return their 8-24 hour urine collection at the next visit, no later than 7 days after their previous visit. Patients were to refrigerate urine collections at all times except during transport.

Safety Variables

Safety was assessed by monitoring the incidence of bronchospasm and by the quantitative change in pulmonary function (measured as change in $FEV_1\%$ predicted), the incidence of treatment emergent adverse events, and the incidence of unusually high serum tobramycin results ($\geq 4$ µg/mL), the significance of clinical laboratory test results, and the significance of change in clinical evaluation results.

Bronchospasm (Airway Reactivity)

One objective of the study was to compare the rate of occurrence of bronchospasm (airway reactivity) between control and experimental delivery systems. Bronchospasm was measured by the change in forced expiratory volume in 1 second [$FEV_1$ (liters)] from before dosing to 30 minutes after dosing during periods 1, 2, and 3. The number and percent of patients who experienced predose to postdose decreases in $FEV_1$ (liters) that were $\geq 10\%$ and those that were $\geq 20\%$ were determined to assess the comparative incidence of bronchospasm among control and experimental treatments. Decreases in $FEV_1$ (liters) that were $\geq 20\%$ were considered clinically significant for the purposes of the study. Additionally, an acute decrease in $FEV_1$ (liters) $\geq 30\%$ from before to after treatment was considered a symptom of respiratory distress. In this event, continuation of the patient in the study was at the discretion of the investigator.

Norms have been developed for $FEV_1$. These norms are commonly used in studies of pulmonary patients. This study employed the Knudson equations that use age, gender, and height to predict a patient's $FEV_1$ values as if the patient was free of pulmonary function disease. The actual $FEV_1$ value is divided by the normative value, and the resulting ratio is multiplied by 100 to produce a measure that represents percentage of predicted normal function, commonly called percent predicted. The transformation is:

$$FEV_1\% \text{ predicted} = (FEV_{1\ actual\ value}/FEV_{1\ normative\ value}) \times 100$$

Relative change in $FEV_1\%$ predicted is defined as the percent change from predose to 30 minutes postdose in $FEV_1\%$ predicted and is calculated as:

relative change in $$FEV_1\% \text{ predicted} = [(FEV_{1\ (\%\ predicted\ at\ 30\ minutes\ post\text{-}dose)} - FEV_{1\ (\%\ predicted\ at\ predose)})/FEV_{1\ (\%\ predicted\ at\ predose)}] \times 100$$

Clinical Laboratory Tests

Serum creatinine, blood urea nitrogen (BUN), and dipstick urine protein results were obtained from specimens drawn during screening and before dosing during treatment period 3. Urine dipstick testing was always performed on fresh specimens. Serum and urine specimens that needed to be retained at the site (e.g., those drawn after shipping pick-up hours or on Friday or Saturday) were frozen until shipment at the next earliest shipping time. Specimens were covered with dry ice for shipping.

All out of range laboratory results were evaluated for clinical significance and drug relationship by the investigator using the following classification scheme:

clinically insignificant;
possible study medication relationship;
probable study medication relationship;
unrelated to study medication, related to concurrent illness;
unrelated to study medication, related to other concurrent medication;
other (investigator commentary).

Aerosol Delivery Variables

Evaluation of the aerosol delivery characteristics of the Aerodose breath actuated nebulizer, compared to characteristics of the FDA-approved PARI LC PLUS jet nebulizer with PulmoAide compressor, was based on determination of sputum, urine, and serum tobramycin concentrations, calculation of certain sputum and serum pharmacokinetic parameters, and measurement of nebulization time.

Sputum Tobramycin Concentrations

Before study treatments were administered, patients expectorated sputum produced from a deep cough into an individual specimen container. Immediately after treatment, patients rinsed their mouths three times with 30 mL of normal saline, gargled for 5-10 seconds, and expectorated the rinse.

Post treatment sputum specimens were collected following the normal saline gargle at 10 minutes and at 1, 2, 4, and 8 hours after completion of the aerosol drug administration for determination of sputum tobramycin concentrations. Sputum specimens were judged to be acceptable if collected within ±2 minutes of the scheduled 10-minute posttreatment collection time and within ±10 minutes of the scheduled 1-, 2-, 4-, and 8-hour collection times. After collection, specimens were immediately frozen for later determination of tobramycin concentrations in sputum. A minimum of 1 gram of sputum was required for analysis. Tobramycin concentrations in sputum (sputum LOQ=20.0 µg/gm) were measured by using HPLC.

Serum Tobramycin Concentrations

Whole blood was drawn by venipuncture, an indwelling heparin/saline lock, or a permanent venous access port at 10 minutes and at 1, 2, 4, and 8 hours after completion of dosing. Blood specimens were judged to be acceptable if collected within ±2 minutes of the scheduled 10-minute posttreatment collection time and within ±10 minutes of the scheduled 1-, 2-, 4-, and 8-hour collection times. Blood specimens were allowed to clot for 30 minutes and were then centrifuged at 1500×g for 10 minutes until clot and serum separated. Serum samples (3 mL) were pipetted into plastic vials and frozen immediately for later determination of serum tobramycin concentrations.

Tobramycin concentrations in serum were measured by Abbott TDxFLx® assay (Abbott Laboratories, Abbott Park, Ill.) [serum lower limit of quantitation (LOQ)=0.18 µg/mL].

Urine Tobramycin Recovery

Urine specimens were collected and combined in a 24-hour collection container during the 12 hours before treatment (−12-0 hour period) and during 0-8 hour and 8-24 hour collection periods after treatment according to instructions provided in the Study Manual. Total urine volume for the collection period was recorded, and a 10 mL aliquot from each urine collection was retained and frozen for later analysis of urine tobramycin concentration.

The recovery of tobramycin in urine (in milligrams) during 0-8 hour and 8-24 hour collection periods was calculated as follows.

urine tobramycin recovery (µg)=urine volume (mL)
·urine tobramycin concentration (µg/mL)

Urine tobramycin recovery was normalized for each collection period according to TOBI dose as follows.

dose-normalized urine tobramycin recovery (µg/mg)=
[urine tobramycin recovery (µg)÷TOBI dose (mg)]

The percent of the TOBI dose excreted in urine in the 24-hour period following treatment was calculated as follows.

% tobramycin excreted in urine=[(urinary recovery in µg÷1000 µg/mg)÷TOBI dose in mg]·100%.

If either the urine volume or the urine tobramycin concentration for a collection interval was missing, then the urine tobramycin recovery was not calculable for that interval. If calculated urine tobramycin recovery was missing for either the 0-8 hour or the 8-24 hour collection interval, then the 0-24 hour urine tobramycin recovery was not calculated. Missing urine tobramycin recovery values were not replaced by estimated values for analysis purposes.

Tobramycin concentrations in urine were measured by Abbott TDxFLx® assay [urine lower limit of quantitation (LOQ)=1.0 µg/mL].

Pharmacokinetic Parameters

The maximum tobramycin concentrations ($C_{max}$) in sputum and serum during the 8-hour posttreatment sampling period were identified for each patient during each treatment period, and the time at which $C_{max}$ was observed ($T_{max}$) was recorded.

Area under the concentration-time curve through 8 hours postdose ($AUC_{0-8}$) was calculated from sputum and serum tobramycin concentrations using the linear trapezoidal method. Nebulization time (excluding time for refilling) was added to the time between predose and 10 minutes postdose for $AUC_{0-8}$ calculations.

Area under the concentration-time curve extrapolated to infinity ($AUC_{0-\infty}$) was calculated for sputum and serum as follows.

$$AUC_{0-\infty} = AUC_{0-last} + C_{(last)} \div k_{el}$$

where: $AUC_{0-last}$ is area under the curve from predose through the last non-BQL time $C_{(last)}$ is the last non-BQL posttreatment concentration result $k_{el}$ is the elimination rate constant (terminal phase slope) and $k_{el}$=log 2÷$T_{1/2}$ where $T_{1/2}$ is the elimination half-life for the patient.

Relative systemic bioavailability was calculated based on serum $AUC_{0-8}$ values for control (TOBI 300 mg delivered by PARI LC PLUS nebulizer) and experimental (TOBI 30 mg, 60 mg, and 90 mg delivered by Aerodose inhaler) groups as follows.

relative bioavailability (%) = experimental group serum $AUC_{0-8}$ ÷ control group serum $AUC_{0-8}$ Missing tobramycin concentrations and those reported as zero or below quantifiable limits (BQL) were not to be replaced with any estimated value. $C_{max}$ and $AUC_{0-8}$ were always determinable except in the event that all posttreatment tobramycin concentrations were missing, zero, or BQL. There was no missing sputum $C_{max}$ and $AUC_{0-8}$ values among the 49 patients who completed the study (refer to report section 9.3.1 for details). Four completing patients had indeterminate serum $C_{max}$ and $AUC_{0-8}$ values due to BQL serum results for each posttreatment sampling time (refer to report section 9.4.1 for details).

Nebulization Time

The timing (duration) of nebulization began with the patient's first tidal breath after the device was in place and continued until the device aerosolized no more TOBI solution. Nebulization time did not include any interruptions or time needed for instillation of drug into the nebulizer between the repeat filling of the AeroDose™ inhaler. The length of any interruption in nebulization and the reason for interruption were recorded.

Safety Analyses

Reductions in $FEV_1\%$ predicted $\geq 10\%$ and $\geq 20\%$ were used as indicators of the occurrence of bronchospasm (airway reactivity). McNemar's test for paired comparisons (replacing the Cochran-Mantel-Haenszel (CMH) test) was used for control vs. experimental treatment comparisons of the incidence of patients with predose to 30-minute postdose decreases in $FEV_1\%$ predicted that were $\geq 10\%$ and $\geq 20\%$. In addition, pairwise t-tests were used to compare mean relative change in spirometry $FEV_1\%$ predicted from predose to postdose between each experimental treatment and the control treatment. All statistical analyses were performed using two-sided tests conducted at a 0.05 significance level (i.e., $\alpha = 0.05$). Since all statistical tests were exploratory in nature, no adjustment of p-values was made for multiple testing. Changes from predose to postdose in vital signs, body weight, and the incidence of abnormal and/or clinically significant laboratory and physical examination results were summarized and evaluated descriptively.

Individual patient serum tobramycin results were monitored for unusually high values ($\geq 4$ µg/mL) that might potentially indicate the occurrence of systemic toxicity.

Aerosol Delivery Analyses

The natural logarithms of $AUC_{0-8}$, $AUC_{0-\infty}$, and $C_{max}$ based on sputum and serum tobramycin concentrations were to be statistically analyzed using a mixed-effect repeated-measure analysis of variance model containing treatment, sequence, period, and carryover as fixed effects and patient as a random effect. In the planned analysis of variance model, sequence and carryover (treatment by period interaction) effects were confounded. The actual model used for the analysis was therefore modified by dropping the sequence term so that the assessment of carryover (i.e., treatment by period interaction) could proceed. When $AUC_{0-\infty}$ values were calculated, large outlier values were noted, and the analysis for this parameter was dropped.

Three hypotheses regarding whether the experimental delivery treatment of 30 mg, 60 mg, or 90 mg TOBI was equivalent to the control delivery treatment of 300 mg TOBI were to be tested in the model. The experimental treatment to control ratio for each of the log AUC and $C_{max}$ parameters was estimated with 90 percent confidence intervals (CIs). Upper and lower limits for the CIs were then obtained by back transformation (i.e., by exponentiating the log values of the upper and lower limits) to the original scale of the parameter. If the CIs for the ratio of experimental and control treatments contained the value of 1.0, it was concluded that the treatments were not significantly different at the $\alpha = 0.1$ for the 90% CIs.

If demographic or baseline characteristics showed important apparent differences between the three experimental AeroDose™ groups compared to all patients, then the discrepant factor and its interaction with the delivery treatment factor were to be added to the mixed-effect model. Exploratory evaluations of age, gender, body weight, and baseline pulmonary function ($FEV_1$ percent predicted) demonstrated no important effects on pharmacokinetic results.

Disposition of Patients

A total of 56 patients were screened for the study by the nine investigators. Fifty-three patients met entrance criteria, were enrolled in the study, and were randomized to one of the 12 sequences of treatment administration identified in the randomization code. A total of 3 patients failed to meet entrance criteria and were not enrolled in the study: 2 patients had screening $FEV_1\%$ predicted results that were below the 40% criterion required for entry, and one patient exhibited disqualifying serum creatinine, BUN, and/or proteinuria.

Accrual of the 53 randomized patients at 9 sites was as follows: 3 sites randomized 8 patients each, 2 sites randomized 7 patients, 3 sites randomized 4 patients, and one site randomized 3 patients. Fifty two patients received at least one dose of study treatments, and one patient was enrolled and randomized but withdrew from the study before the first study treatment due to increased productive cough with a significant decline in forced expiratory volume (FEV) since screening (both events and associated hyperventilation were considered SAEs due to hospitalization of the patient: included in study database).

Of the 52 patients who received study treatments, 49 patients completed the study, and 3 patients withdrew after having received one dose of study treatment. Two of the withdrawn patients discontinued the study during the control treatment period (TOBI 300 mg administered by PARI LC PLUS nebulizer), and one patient withdrew during the TOBI 90 mg by AeroDose™ inhaler treatment period.

Baseline Characteristics

Enrolled patients had documented laboratory (sweat chloride $\geq 60$ mEq/L by quantitative pilocarpine iontophoresis test (QPIT) and/or genotype with 2 identifiable mutations) and clinical evidence consistent with a diagnosis of cystic fibrosis. Patients met all inclusion and exclusion criteria except for one patient whose pulmonary function entrance requirement ($FEV_1 \geq 40\%$ of predicted based on gender, age, and height) was waived (the patient's screening $FEV_1\%$ predicted was 39.87%). The average $FEV_1\%$ predicted of all randomized patients was 66.4% at screening with a range from approximately 40% to 116%.

Patients reported no known local or systemic hypersensitivity to aminoglycosides. Patients had taken no loop diuretics, no form of aminoglycoside within 7 days before study treatments, and no investigational medications within 2 weeks before study treatments.

Female patients had a negative pregnancy test before study treatments, and all patients had serum creatinine $\leq 2.0$ mg/dL, BUN <40 mg/dL, and <2+ proteinuria at visit 1 screening, as required by the protocol. Screening or repeat serum creatinine and BUN results were within the normal ranges for these tests before study treatments. Screening or repeat urine protein results were positive 1+ in 3 patients, but this result did not preclude participation of these patients in the study.

No disqualifying medical history or physical examination findings were noted at visit 1 screening. Screening and visit 1 predose vital signs were unremarkable for nearly all patients. One patient exhibited low systolic and diastolic blood pressures at (72/49 mmHg), but these results did not preclude participation of the patient in the study.

Safety Evaluation

Extent of Exposure

Forty-nine patients received all 3 single doses of study treatments according to the randomization code, and 3 patients who withdrew from the study received one dose of study treatment. These 52 patients were included in the safety evaluation. Fifty-one of the 52 patients received a single dose of TOBI 300 mg, and 34, 32, and 33 of the 52 patients received a single dose of TOBI 30 mg, 60 mg, and 90 mg, respectively. Three of the 49 completing patients had to stop treatment due to inhaler malfunction and subsequently repeated the treatment period at a later date. As a result, these 3 patients received a partial dose of TOBI during the period in which the malfunction occurred (the amount of the partial dose was not recorded) and a full dose of TOBI during the repeated period.

Pulmonary Function Results

Bronchospasm

In one aspect, the study compared the rate of occurrence of bronchospasm (airway reactivity) between control and experimental delivery systems. The occurrence of bronchospasm was determined quantitatively based on the percent change in $FEV_1$ (liters) from before dosing to 30 minutes after dosing in each of the 3 treatment periods. For the purposes of the study, predose to postdose reductions in $FEV_1$ (liters)$\geq$10% and $\geq$20% were defined as bronchospasm; reductions in $FEV_1$ (liters)$\geq$20% were considered clinically significant.

Fifteen patients (9 male and 6 female) experienced 24 instances of bronchospasm during the study. Two instances of clinically significant bronchospasm were observed (decline in $FEV_1$ (liters)$\geq$20%: patient 105-1034 after TOBI 300 mg and patient 102-1040 after TOBI 60 mg). No statistically significant pairwise differences in the overall incidence of bronchospasm were noted between control and experimental treatments. No clear relationship appeared to exist between the incidence of bronchospasm and TOBI dose or delivery system (see Table 2 below).

One patient 34 experienced clinically significant bronchospasm at 30 minutes after completing the TOBI 300 mg dose during treatment period 1 (visit 2). This 32-year old male patient's $FEV_1$ was 2.55 L before dosing and 1.98 L (decline in $FEV_1$ (liters)$\geq$20%) at 30 minutes after dosing. He experienced moderate chest tightness that resolved spontaneously. This patient also experienced a second episode of bronchospasm 30 minutes after TOBI 60 mg during period 2. The $FEV_1$ was 2.47 L before dosing and 2.14 L (decline in $FEV_1$ (liters)$\geq$10% but <20%) at 30 minutes after dosing. No symptomatology was reported at the time of this event. No prestudy aminoglycoside use was noted for this patient.

One patient experienced one instance of clinically significant bronchospasm 30 minutes after TOBI 60 mg during period 3 (visit 4) of the crossover. This 36-year old male patient's $FEV_1$ was 2.26 L before dosing and 1.75 L (decline in $FEV_1$ (liters)$\geq$20%) at 30 minutes after dosing (Archival Listing 3), but he reported no other symptomatology at this time. No prestudy aminoglycoside use was noted for this patient. This episode of bronchospasm appeared due in part to an uncharacteristically high predose $FEV_1$ value. The 30-minute posttreatment value was similar to that obtained during period 2 when the change in $FEV_1$ did not meet the definition of bronchospasm.

Among the 13 patients who experienced clinically non-significant bronchospasm, one patient experienced a decline in $FEV_1$ (liters)$\geq$10% but <20% after all three study doses were administered, 6 patients experienced a decline in $FEV_1$ (liters)$\geq$10% after two doses of study medication, and 6 patients experienced a single instance of bronchospasm. Table 3 below lists instances of bronchospasm by patient, treatment period, and TOBI dose.

TABLE 3

Patient Dosing Regimen and Acute Bronchospasm

| Site-Patient ID/Gender | Period 1 (Visit 2) TOBI Dose Received | Period 2 (Visit 3) TOBI Dose Received | Period 3 (Visit 4) TOBI Dose Received |
|---|---|---|---|
| 108-1048 [b]/Female | 300 [c] | 30 [c] | 60 |
| 109-1015 [b]/Male | 300 | 30 [c] | 60 |
| 107-1027/Male | 300 | 30 [c] | 90 [c] |
| 103-1038 [b]/Female | 300 [c] | 60 | 30 |
| 105-1034/Male | 300 [d, e] | 60 [c] | 30 |
| 107-1026/Female | 300 | 60 [c] | 90 |
| 102-1009 [b]/Female | 300 [c] | 90 [c] | 30 |
| 102-1040 [b]/Male | 300 | 90 | 60 [d] |
| 106-1050 [b]/Female | 30 [c,e] | 300 | 90 |
| 102-1007 [b]/Male | 60 [c] | 300 [c] | 30 |
| 104-1021/Male | 60 [c] | 300 [c] | 30 |

TABLE 2

Incidence of Acute Bronchospasm by Treatment

| Bronchospasm Parameter | TOBI 300 mg PARI LC PLUS[1] (N = 51) | TOBI 30 mg Aerodose inhaler[2] (N = 34) | TOBI 60 mg Aerodose inhaler[2] (N = 32) | TOBI 90 mg Aerodose inhaler[2] (N = 33) |
|---|---|---|---|---|
| $FEV_1$ Decrease $\geq$10% | 9 (17.6%) | 5 (14.7%) | 6 (18.8%) | 4 (12.1%) |
| $FEV_1$ Decrease $\geq$20% | 1 (2.0%) | 0 (0.0%) | 1 (3.1%) | 0 (0.0%) |

Bronchospasm was defined by protocol as a decrease in $FEV_1$ (liters) $\geq$10% and $\geq$20% from predose to 30 minutes postdose. Declines $\geq$20% were considered clinically significant.
[1]Control (C) treatment = TOBI 300 mg delivered by PARI LC PLUS nebulizer.
[2]Experimental (E) treatments = TOBI 30, 60, or 90 mg delivered by Aerodose inhaler.

TABLE 3-continued

Patient Dosing Regimen and Acute Bronchospasm

| Site-Patient ID/Gender | Period 1 (Visit 2) TOBI Dose Received | Period 2 (Visit 3) TOBI Dose Received | Period 3 (Visit 4) TOBI Dose Received |
|---|---|---|---|
| 108-1044/Male | 60 | 300 [c] | 30 [c] |
| 105-1047/Female | 60 | 300 [c] | 90 |
| 106-1022 [b]/Male | 90 [c,e] | 300 | 30 |
| 106-1041 [b]/Male | 90 [c,e] | 300 [c] | 60 [c] |

Bronchospasm is defined as a decrease in $FEV_1$ (liters) $\geq 10\%$ and $\geq 20\%$ from predose to 30 minutes postdose. Declines $\geq 20\%$ were considered clinically significant.
[b] The patient used a bronchodilator before dosing with study medication.
[c] Bronchospasm (not clinically significant): decrease in $FEV_1$ (liters) $\geq 10\%$ but <20%.
[d] Bronchospasm (clinically significant): decrease in $FEV_1$ (liters) $\geq 20\%$.
[e] The patient also reported "lung function decrease" (COSTART term) as an AE during the designated treatment period.

Three of the 15 patients with bronchospasm reported treatment-related symptoms at the same time. One patient 15 experienced moderate wheezing (coded as asthma) after TOBI 30 mg during period 2, one patient 4 experienced moderate chest tightness (coded as chest pain as reported previously) after TOBI 300 mg during period 1, and one patient 41 experienced increased cough after TOBI 60 mg during period 3. All events resolved either spontaneously (chest tightness), with treatment (wheezing), or by holding and restarting therapy (increased cough). None of the adverse events led to a serious outcome.

Four of the 15 patients with bronchospasm (and one patient without bronchospasm) reported "lung function decreased" (COSTART term) as an adverse event. In addition to the 4 patients with bronchospasm identified in Table 3 above, one patient who experienced no bronchospasm, reported lung function decreased once after TOBI 60 mg and once after TOBI 90 mg delivered by the AeroDose™ inhaler.

Initial instances of bronchospasm occurred more frequently during period 1 than during periods 2 or 3 of the crossover. Nine of the 15 patients first experienced bronchospasm during the first treatment period (visit 2), five patients during the second treatment period, and one patient during the third treatment period.

Patients who routinely used a bronchodilator were permitted to continue to do so during the study. Bronchodilator doses were to be administered 15 to 60 minutes prior to study treatments. Nine of the 15 patients who experienced bronchospasm during the study used a bronchodilator prior to administration of study treatment.

Relative Change in $FEV_1\%$ Predicted

The magnitude of the relative change in $FEV_1\%$ predicted was calculated as a quantitative measure of the effect of TOBI treatments on pulmonary function during the study. There were no statistically significant differences among the 4 treatments and no evidence of the presence of period or carryover (treatment by period interaction) effects. Results of pairwise comparisons between control and experimental treatments are summarized in Table 4. Since the overall treatment difference was not statistically significant, the significant p-value for the TOBI 300 mg vs. TOBI 30 mg comparison in Table 4 below (p=0.019) should not be interpreted as conclusive evidence of a difference. FIG. 1 graphically illustrates the mean relative changes in $FEV_1\%$ predicted from before to 30 minutes after dosing for each of the treatments.

TABLE 4

MEAN (SD) RELATIVE CHANGE IN $FEV_1$ % PREDICTED

| $FEV_1$ % Predicted (%) Parameter | TOBI 300 mg PARI LC PLUS[1] (n = 51) | TOBI 30 mg Aerodose inhaler[2] (n = 34) | TOBI 60 mg Aerodose inhaler[2] (n = 32) | TOBI 90 mg Aerodose inhaler[2] (n = 33) |
|---|---|---|---|---|
| Predose | 67.8 (18.4) n = 51 | 65.5 (17.1) n = 34 | 65.4 (16.8) n = 32 | 71.3 (20.0) n = 33 |
| 30 minutes postdose | 63.7 (17.6) n = 51 | 63.0 (16.7) n = 34 | 62.5 (15.7) n = 32 | 68.7 (19.1) n = 32 |
| Relative change from predose[3] | −6.1 (5.2) n = 51 | −3.8 (5.4) n = 34 | −4.2 (6.2) n = 32 | −3.2 (7.4) n = 32 |
| P-value for crossover: | | Treatment: 0.141 | Period: 0.199 | Carryover: NC |
| Pairwise contrasts: C vs. E p-value (paired t-test): | | 0.019 | 0.058 | 0.083 |

[1]Control (C) treatment = TOBI 300 mg delivered by PARI LC PLUS nebulizer.
[2]Experimental (E) treatments = TOBI 30, 60, or 90 mg delivered by Aerodose inhaler.
[1]Relative change from predose = 100% · ((30 minute postdose value − predose value)/predose value).
NC = carryover (treatment by period interaction) effect not statistically significant and was dropped from final model.

Safety Conclusions

Nine males and six females experienced treatment-induced bronchospasm during the study. There was no difference in the rate of occurrence of TOBI induced bronchospasm between control and experimental delivery systems regardless of dose. The occurrence of bronchospasm was rarely associated with patient symptoms. All but four of the patients experiencing drug-induced bronchospasm had been prescribed bronchodilators prior to the study suggesting that they had a history of airway reactivity. The disproportionate number of males versus females experiencing airway reactivity is unusual in light of the fact that enrollment was approximately 60% female and 40% male. The pivotal trials showed that gender had no influence on drug induced airway reactivity. However, it would be difficult to base any conclusions on this finding due to the small patient numbers in this study.

Treatment-emergent adverse events occurred in all treatment groups regardless of causality. The most common treatment-emergent experiences were associated with Respiratory and Body as a Whole systems. The most common individual events were cough increased, rhinitis, sputum increased, asthma, chest pain, and headache. These events were also common to the patient's pretreatment symptoms reflecting the patients underlying disease. For the majority of treatment-emergent adverse events, there were no meaningful differences between TOBI doses or between the PARI LC PLUS nebulizer and the AeroDose™ inhaler.

The serious adverse events (SAEs) reported were primarily associated with an exacerbation of the patients underlying disease states. The one treatment-related SAE involved a possible sensitivity reaction that, if documented, would have occurred regardless of device or dose.

Review of the clinical chemistry, vital signs, and physical findings did not reveal any clinically significant safety issues associated with the dose or delivery system used to administer TOBI.

All the patients were on multiple concurrent medications appropriate to their disease state (cystic fibrosis), other underlying illnesses, and age throughout the study. The concurrent medications did not appear to have any influence on the safety profile of the study drug or either device during the study. Overall, no clinically significant or unexpected safety issues for TOBI were identified in the study. The study showed that there were no meaningful differences in the safety profiles of administering TOBI via the PARI LC PLUS delivery system in comparison with the Aerodose delivery system regardless of dose.

Aerosol Delivery Results

Data Analysis

Forty-nine of the 52 dosed patients completed the study and were evaluable for pharmacokinetics by reason of having completed at least 2 doses of study treatments. These 49 patients also constituted the "completers" subset of patients referred to in the summary tables. Three of the 52 dosed patients discontinued the study before completing 2 doses of study treatments and were not evaluable for pharmacokinetics. All 52 patients were evaluable for the aerosol delivery objective (nebulization time) of the study.

Sputum Tobramycin Concentrations and Pharmacokinetic Parameters

Compliance with Specimen Collection Requirements

Six of 49 completing patients had a total of 11 missing sputum specimens. No more than one sputum sample was missed per treatment-time (e.g., for TOBI 300 mg at one hour postdose). Two patients missed 2 or more sputum samples during the study, and four patients missed a single sputum sample.

A single completing patient provided no sputum pharmacokinetic data for the TOBI 60 mg treatment. One patient had missing sputum samples from 10 minutes through 8 hours after TOBI 60 mg treatment. After the database was locked, the missing sputum concentration results were located. Sputum tobramycin concentrations at 10 minutes and 1, 2, 4, and 8 hours were 0.82 µg/gm, BQL, 0.0, 0.0, and 0.0, respectively. The database was not subsequently unlocked to add these data, since the inclusion of these values would have had minimal impact on estimation and analyses of pharmacokinetic parameters. As a result, only $C_{max}$ (0.82 µg/gm) and $T_{max}$ (10 minutes=0.17 hour) values were excluded from TOBI 60 mg PK estimates and analyses; AUC values were incalculable due to BQL tobramycin concentrations from one through 8 hours after TOBI 60 mg treatment.

Sputum Tobramycin Concentrations

Pretreatment sputum tobramycin concentrations for all completing patients were below the limit of quantifiability (LOQ) throughout the study.

Figure 2:
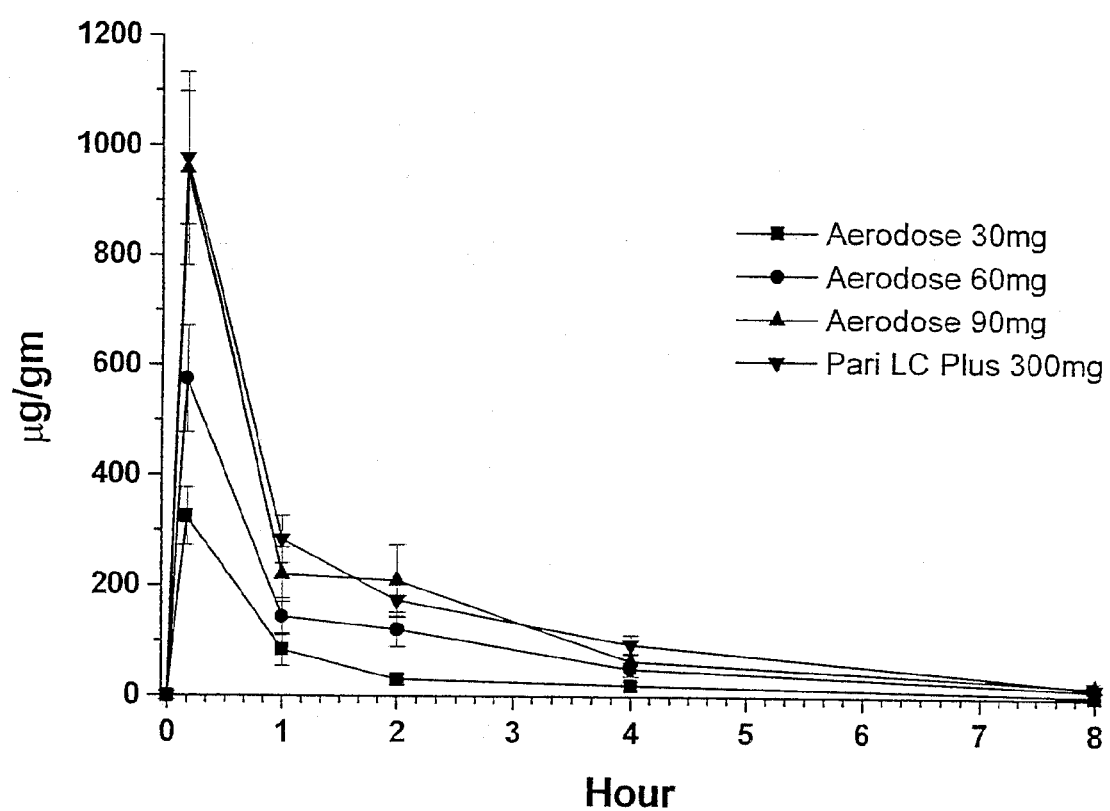

After dosing, sputum concentrations increased rapidly, reaching maximum concentrations within 10 minutes (see FIG. 2), and declined thereafter with median half-life values ranging from approximately 1.6 to 2.1 hours during the four treatments. The sputum concentrations were highly variable among patients, as coefficients of variation (standard deviation divided by the mean times 100%) approached or exceeded 100% for each treatment at all time points.

For the AeroDose™ inhaler, mean sputum tobramycin concentrations increased with increasing TOBI dose at each measurement time during the 8-hour postdose period. Mean sputum concentrations for the TOBI 90 mg treatment with the AeroDose™ inhaler were similar throughout the 8-hour period to those obtained for the TOBI 300 mg treatment with the PARI LC PLUS nebulizer.

By 2 hours after the end of TOBI 30 mg and by 8 hours after TOBI 60 mg, 90 mg, and 300 mg treatments, sputum concentrations were below LOQ in at least half of the patients. Period effects on sputum tobramycin concentrations were not observed.

After TOBI administration using the AeroDose™ inhaler, maximum plasma concentrations ($C_{max}$) and area under the plasma concentration time profile ($AUC_{0-8}$) increased linearly with dose (Table 5 below and FIGS. 3 and 4), suggesting linear pharmacokinetics. Dose normalized $C_{max}$ and AUC values were comparable among AeroDose™ dose levels, indicating dose proportionality (based on AUC values).

Comparing devices, mean $C_{max}$ and $AUC_{0-8}$ for the TOBI 90 mg treatment delivered by the AeroDose™ inhaler achieved similar levels as those obtained by the TOBI 300 mg treatment delivered by the PARI LC PLUS nebulizer. The dose normalized $C_{max}$ and $AUC_{0-8}$ results were higher during AeroDose™ treatments than during the PARI LC PLUS treatment, indicating that the AeroDose™ inhaler exhibited higher efficiency. The bioavailability of the AeroDose™ device was about 3-fold higher than that of the PARI LC PLUS nebulizer.

Exploratory analyses suggested that sputum pharmacokinetic results were unaffected by characteristics present before treatments began (age, gender, body weight, $FEV_1$% predicted at screening) and were unaffected by events noted after the start of treatments (device failure, occurrence of bronchospasm defined as a decrease ≧10% in $FEV_1$, and relative change in $FEV_1$% predicted).

TABLE 5

MEAN (SD) SPUTUM TOBRAMYCIN PHARMACOKINETIC PARAMETERS

| Sputum Pharmacokinetic Parameters | TOBI 300 mg PARI LC PLUS[a] (n = 49) | TOBI 30 mg Aerodose inhaler[b] (n = 34) | TOBI 60 mg Aerodose inhaler[b] (n = 32) | TOBI 90 mg Aerodose inhaler[b] (n = 32) |
|---|---|---|---|---|
| $C_{max}$ (µg/gm) | 985.65 (839.34) | 329.05 (311.30) | 577.83 (538.42) | 958.00 (952.30) |
| No. pts with data: | 49 | 34 | 31 | 32 |

TABLE 5-continued

MEAN (SD) SPUTUM TOBRAMYCIN PHARMACOKINETIC PARAMETERS

| Sputum Pharmacokinetic Parameters | TOBI 300 mg PARI LC PLUS[a] (n = 49) | TOBI 30 mg Aerodose inhaler[b] (n = 34) | TOBI 60 mg Aerodose inhaler[b] (n = 32) | TOBI 90 mg Aerodose inhaler[b] (n = 32) |
|---|---|---|---|---|
| E vs C p-value[c]: | | <0.001 | 0.002 | 0.856 |
| E/C (90% CIs)[d]: | | (0.23, 0.41) | (0.43, 0.75) | (0.72, 1.30) |
| Dose-normalized Cmax (µg/gm)/mg | 3.29 (2.80) | 10.97 (10.38) | 9.63 (8.97) | 10.64 (10.58) |
| No. pts with data: | 49 | 34 | 31 | 32 |
| E/C (90% CIs)[d]: | | | | (2.82, 5.13) |
| $T_{max}$ (hr) | 0.26 (0.38) | 0.24 (0.24) | 0.38 (0.76) | 0.33 (0.41) |
| No. pts with data: | 49 | 34 | 31 | 32 |
| $T_{1/2}$ (hr) | 6.41 (24.09) | 2.04 (1.31) | 12.89 (42.61) | 13.02 (36.91) |
| Median $T_{1/2}$ (hr) | 1.71 | 1.78 | 2.06 | 1.60 |
| No. pts with data: | 41 | 15 | 21 | 24 |
| $AUC_{0-8}$ (hr · µg/gm) | 1471.16 (1278.22) | 360.79 (422.23) | 804.78 (722.83) | 1275.23 (1358.52) |
| No. pts with data: | 49 | 34 | 31 | 32 |
| E vs C p-value[c]: | | <0.001 | <0.001 | 0.465 |
| E/C (90% CIs)[d]: | | (0.19, 0.28) | (0.45, 0.69) | (0.72, 1.14) |
| Dose-normalized $AUC_{0-8}$ (hr · µg/gm)/mg | 1.90 (4.26) | 12.03 (14.07) | 13.41 (12.05) | 14.17 (15.10) |
| No. pts with data: | 49 | 34 | 31 | 32 |
| E/C (90% CIs)[d]: | | | | (2.78, 4.12) |
| $AUC_{0-\infty}$ (hr · µg/gm) | 1996.36 (2013.70) | 638.68 (586.85) | 1661.66 (2334.89) | 5544.88 (14831.0) |
| No. pts with data: | 41 | 15 | 21 | 24 |

[a]Control (C) treatment = TOBI 300 mg delivered by PARI LC PLUS nebulizer.
[b]Experimental (E) treatments = TOBI 30, 60, or 90 mg delivered by Aerodose inhaler.
[c]Pairwise contrast: TOBI 300 mg PARI LC PLUS group vs TOBI (30, 60, 90 mg) Aerodose groups.
[d]Back-transformed 90% confidence intervals around the mean of the log ratio of E and C treatments.
Sputum limit of quantifiability (LOQ): 20 µg/gm.

Figure 3:
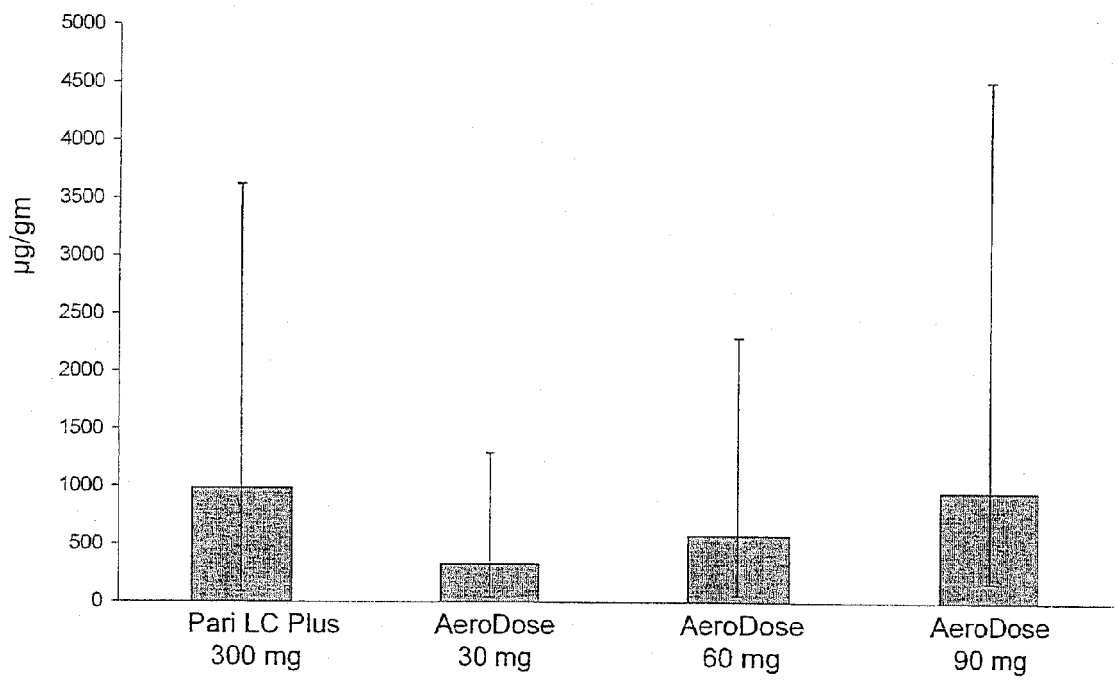
Figure 4:
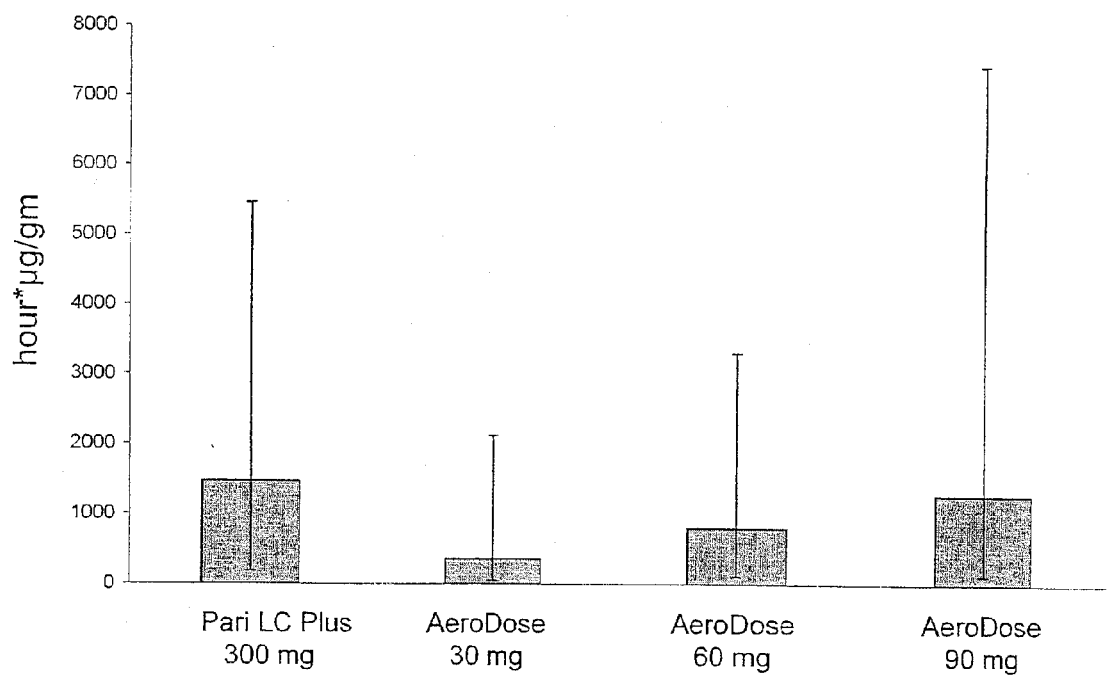

Differences among the treatment groups in $C_{max}$ and $AUC_{0-8}$ (Table 5 above; FIGS. 3 and 4) were statistically significant (p<0.001) with no evidence of period or carryover (treatment by period interaction) effects. In pairwise comparisons, $C_{max}$ and $AUC_{0-8}$ were significantly greater for TOBI 300 mg than for TOBI 30 mg and for TOBI 60 mg but not for TOBI 90 mg (90% CIs for $C_{max}$=(0.72, 1.30); for $AUC_{0-8}$ (0.72, 1.14)).

The AeroDose™ inhaler was more efficient, regardless of TOBI dose, than the PARI LC PLUS nebulizer based on dose normalized sputum $C_{max}$ and $AUC_{0-8}$ results. Dose normalized means for these pharmacokinetic parameters were similar among AeroDose™ treatments but approximately 3-fold higher than the dose normalized results after TOBI 300 mg delivered by the PARI LC PLUS nebulizer (see Table 5).

The time to maximum sputum tobramycin concentrations ($T_{max}$ in Table 5 above) was similar for all treatment groups and averaged between 0.24 and 0.38 hours for AeroDose™ doses compared to 0.26 hours for the TOBI 300 mg treatment using the PARI LC PLUS. Elimination half-life (median $T_{1/2}$ in Table 5) was also similar among AeroDose™ treatments, averaging 1.60 to 2.06 hours, compared to 1.71 hours for TOBI 300 mg.

Exploratory analyses revealed no substantial association between sputum pharmacokinetic results and patient characteristics present before treatments (age, gender, body weight, pulmonary function [$FEV_1$% predicted] at screening) or emergent events after the start of treatments (device failure, occurrence of bronchospasm [decrease ≧10% in $FEV_1$ from predose to 30 minutes postdose], relative change in $FEV_1$.

Serum Tobramycin Concentrations and Pharmacokinetic Parameters

Forty-four (44) of 49 completing patients had no measurable serum tobramycin concentrations before dosing in any of the 3 treatment periods, and five patients exhibited measurable predose serum tobramycin above the lower LOQ in the periods indicated in Table 6 below.

TABLE 6

MEASURABLE TOBRAMYCIN IN PREDOSE SERUM SPECIMENS

| | | Previous Treatment Period | | | Measurable[b] Predose |
|---|---|---|---|---|---|
| Patient | Treatment[a] Sequence | TOBI Dose (mg) | 8-hour Serum Tobramycin Concentration (µg/mL) | Serum $T_{1/2}$ (hr) | Tobramycin during Period Listed -- Tobramycin Concentration (µg/mL) |
| 107-1030 | C-1-2 | prestudy | na[c] | na[c] | Per 1 -- 0.70 |
| 107-1027 | C-1-3 | 300 | <0.20 | 1.68 | Per 2 -- 0.29 |
| 105-1034 | C-2-1 | prestudy | na[c] | na[c] | Per 1 -- 0.28 |
| | | 300 | 1.00 | 7.75 | Per 2 -- 0.23 |
| 103-1019 | 1-C-2 | 30 | 0.35 | 10.85 | Per 2 -- 0.20 |
| 102-1007 | 2-C-1 | prestudy | na[c] | na[c] | Per 1 -- 0.77 |

TABLE 6-continued

MEASURABLE TOBRAMYCIN IN PREDOSE SERUM SPECIMENS

| | | Previous Treatment Period | | | Measurable[b] Predose |
|---|---|---|---|---|---|
| Patient | Treatment[a] Sequence | TOBI Dose (mg) | 8-hour Serum Tobramycin Concentration (μg/mL) | Serum $T_{1/2}$ (hr) | Tobramycin during Period Listed -- Tobramycin Concentration (μg/mL) |
| | | 60 | 0.75 | 7.71 | Per 2 -- 1.38 |
| | | 300 | 0.96 | 10.62 | Per 3 -- 0.60 |

[a]Treatments: C = Control TOBI 300 mg using PARI LC PLUS; 1 = TOBI 30 mg using Aerodose inhaler; 2 = TOBI 60 mg using Aerodose inhaler; 3 = TOBI 90 mg using Aerodose inhaler.
[b]Measurable tobramycin in serum: tobramycin concentration > LOQ (0.2 μg/mL).
[c]na = not available before the start of Period 1.

Table 6 also identifies predose serum specimens for periods 2, 3, or both that had measurable tobramycin in 4 of the 5 patients. These findings are also reflected in non-zero mean amounts of predose tobramycin concentrations in periods 2 and 3. Three of the 5 patients exhibited measurable serum tobramycin after having received TOBI 300 mg during the immediately preceding study period.

These measurable predose results may represent carryover from previous treatment or non-specific assay interference, but the low frequency and magnitude of the results suggests that a substantial effect on posttreatment analyses was unlikely.

Figure 5:
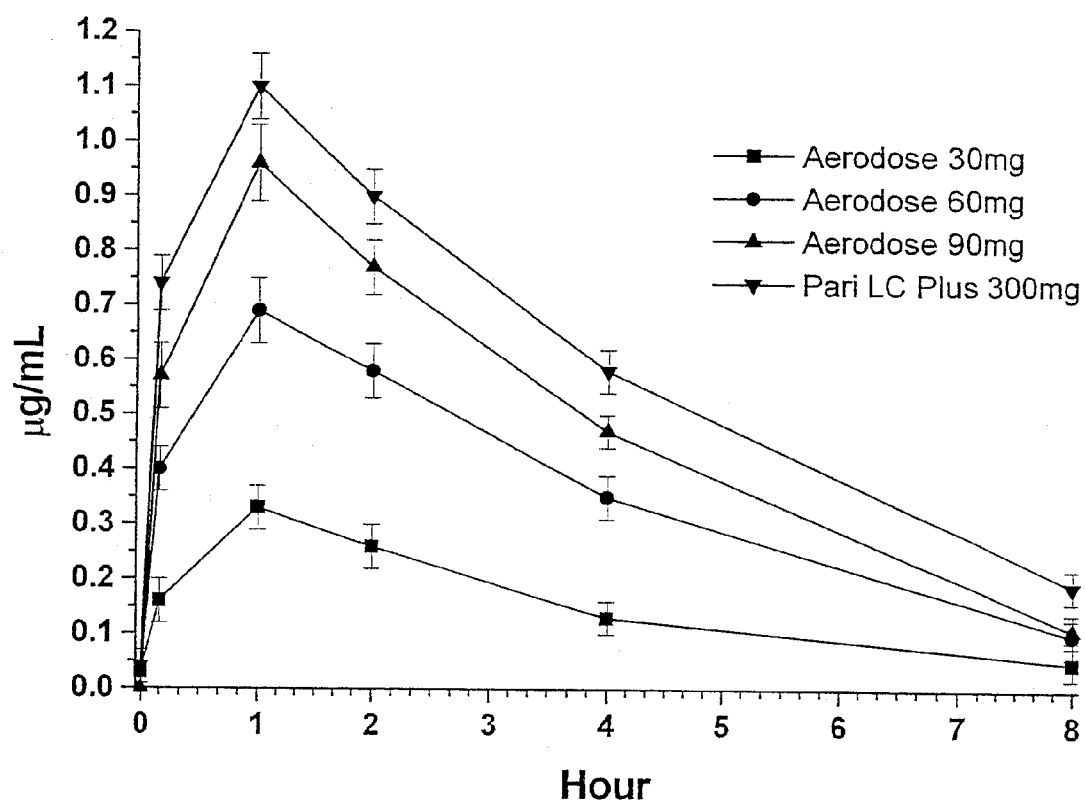

After each of the four TOBI treatments, serum tobramycin concentrations gradually increased, reaching a maximum at one hour after dosing (FIG. 5), and declined thereafter with median half-lives ranging from 2.73 to 4.27 hours (Table 7 below).

For the Aerodose inhaler, mean serum tobramycin concentrations increased with increasing TOBI dose at each time during the 8-hour posttreatment period, but mean values for TOBI 90 mg were less at each posttreatment time than those seen for TOBI 300 mg using the PARI LC PLUS nebulizer.

By 4 hours after the end of TOBI 30 mg and by 8 hours after TOBI 60 mg and 90 mg treatments, serum concentrations were below LOQ in at least half of the patients [median (50th percentile) serum concentrations=0.0 μg/mL]. More than half of the TOBI 300 mg patients remained above the serum LOQ at 8 hours posttreatment. There was no apparent pattern of change in posttreatment serum tobramycin concentrations from period to period for any of the 4 treatments, and there was no clear indication of the presence of a carryover (treatment by period interaction) effect in posttreatment results.

Serum Pharmacokinetic Parameters

After TOBI administration using the Aerodose inhaler, mean $C_{max}$ and AUC results increased linearly with dose after the administration of the 30, 60, and 90 mg doses (Table 7), suggesting linear pharmacokinetics. Dose normalized AUC results were similar among the Aerodose dose levels, suggesting dose proportionality.

Comparing devices, $C_{max}$ and $AUC_{0-8}$ for the TOBI 90 mg dose using the Aerodose inhaler were not as high as results achieved by the TOBI 300 mg dose using the PARI LC PLUS nebulizer. However, the dose-normalized parameters were higher for the Aerodose inhaler at all three TOBI dose levels, indicating better efficiency of the new device. Similar to the sputum data, the relative bioavailability was approximately 3-fold higher for the Aerodose inhaler as compared to the PARI nebulizer. The variability based on AUCs was similar for both devices.

Exploratory analyses suggested that serum pharmacokinetic results were unaffected by characteristics present before treatments began (age, gender, body weight, $FEV_1$% predicted at screening) and were unaffected by events noted after the start of treatments (device failure, occurrence of bronchospasm defined as a decrease ≧10% in $FEV_1$, and relative change in FEV1% predicted).

TABLE 7

MEAN (SD) SERUM TOBRAMYCIN CONCENTRATIONS BY TIME AND PHARMACOKINETIC PARAMETERS

| Serum Pharmacokinetic Parameters | TOBI 300 mg PARI LC PLUS[a] (n = 49) | TOBI 30 mg Aerodose inhaler[b] (n = 34) | TOBI 60 mg Aerodose inhaler[b] (n = 32) | TOBI 90 mg Aerodose inhaler[b] (n = 32) |
|---|---|---|---|---|
| $C_{max}$ (μg/mL) | 1.12 (0.44) | 0.38 (0.17) | 0.69 (0.34) | 0.96 (0.40) |
| No. pts with data: | 49 | 30 | 32 | 32 |
| E vs C p-value[c]: | | <0.001 | <0.001 | 0.027 |
| E/C (90% CIs)[d]: | | (0.29, 0.36) | (0.53, 0.66) | (0.75, 0.96) |
| Dose-normalized $C_{max}$ (μg/mL)/mg | 0.0037 (0.0015) | 0.0127 (0.0058) | 0.0116 (0.0056) | 0.0106 (0.0045) |
| No. pts with data: | 49 | 30 | 32 | 32 |
| E/C (90% CIs)[d]: | | | | (2.52, 3.25) |
| $T_{max}$ (hr) | 1.05 (0.38) | 1.14 (0.42) | 0.98 (0.28) | 1.14 (0.64) |
| No. pts with data: | 49 | 30 | 32 | 32 |
| $T_{1/2}$ (hr) | 3.42 (1.63) | 6.75 (5.31) | 4.16 (2.34) | 3.10 (1.10) |
| Median $T_{1/2}$ (hr) | 3.14 | 4.27 | 3.42 | 2.73 |
| No. pts with data: | 49 | 11 | 28 | 31 |
| $AUC_{0-8}$ (hr · μg/mL) | 4.96 (2.24) | 1.43 (1.43) | 2.98 (1.92) | 3.94 (1.52) |

TABLE 7-continued

MEAN (SD) SERUM TOBRAMYCIN CONCENTRATIONS
BY TIME AND PHARMACOKINETIC PARAMETERS

| Serum Pharmacokinetic Parameters | TOBI 300 mg PARI LC PLUS[a] (n = 49) | TOBI 30 mg Aerodose inhaler[b] (n = 34) | TOBI 60 mg Aerodose inhaler[b] (n = 32) | TOBI 90 mg Aerodose inhaler[b] (n = 32) |
|---|---|---|---|---|
| No. pts with data: | 49 | 30 | 32 | 32 |
| E vs C p-value[c]: | | <0.001 | <0.001 | 0.165 |
| E/C (90% CIs)[d]: | | (0.18, 0.25) | (0.46, 0.62) | (0.75, 1.03) |
| Dose-normalized $AUC_{0-8}$ (hr · μg/mL)/mg | 0.0166 (0.0075) | 0.0478 (0.0477) | 0.0496 (0.0319) | 0.0438 (0.0169) |
| No. pts with data: | 49 | 30 | 32 | 32 |
| E/C (90% CIs)[d]: | | | | (2.51, 3.21) |
| $AUC_{0-\infty}$ (hr · μg/mL) | 6.66 (4.32) | 6.49 (7.71) | 5.11 (4.62) | 5.02 (1.63) |
| No. pts with data: | 49 | 11 | 28 | 31 |

[a]Control (C) treatment = TOBI 300 mg delivered by PARI LC PLUS nebulizer.
[b]Experimental (E) treatments = TOBI 30, 60, or 90 mg delivered by Aerodose inhaler.
[c]Pairwise contrast: TOBI 300 mg PARI LC PLUS group vs TOBI (30, 60, 90 mg) Aerodose groups.
[d]Back-transformed 90% confidence intervals around the mean of the log ratio of E and C treatments.
Serum limit of quantifiability (LOQ): 0.2 μg/mL.

Figure 6:
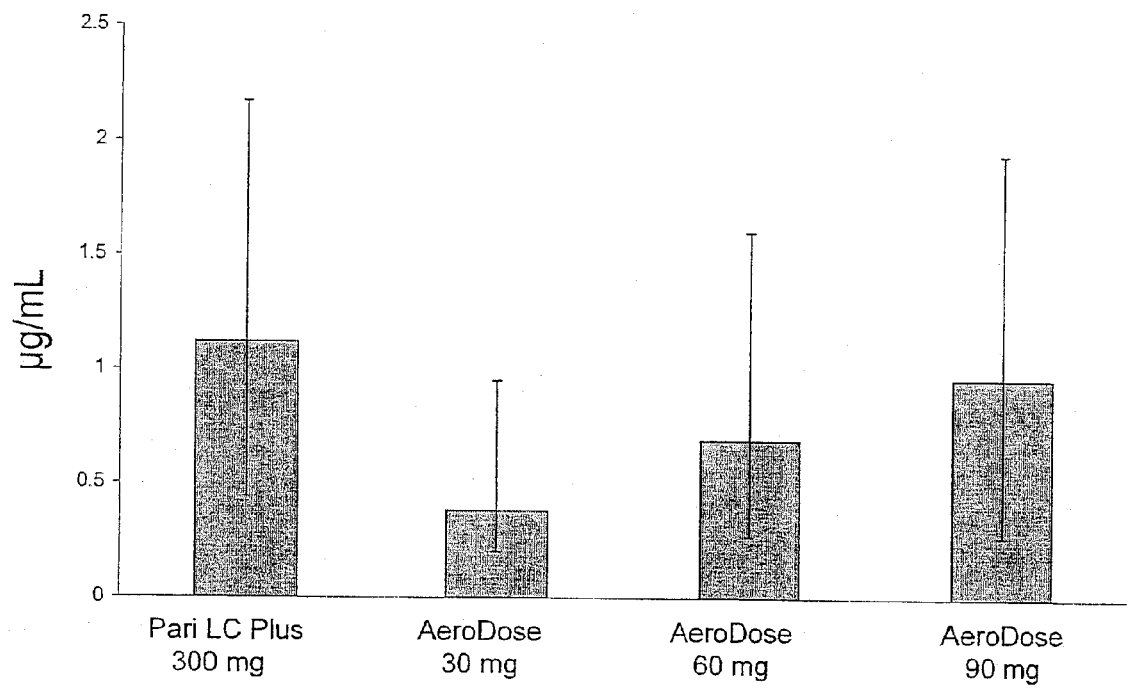
Figure 7:
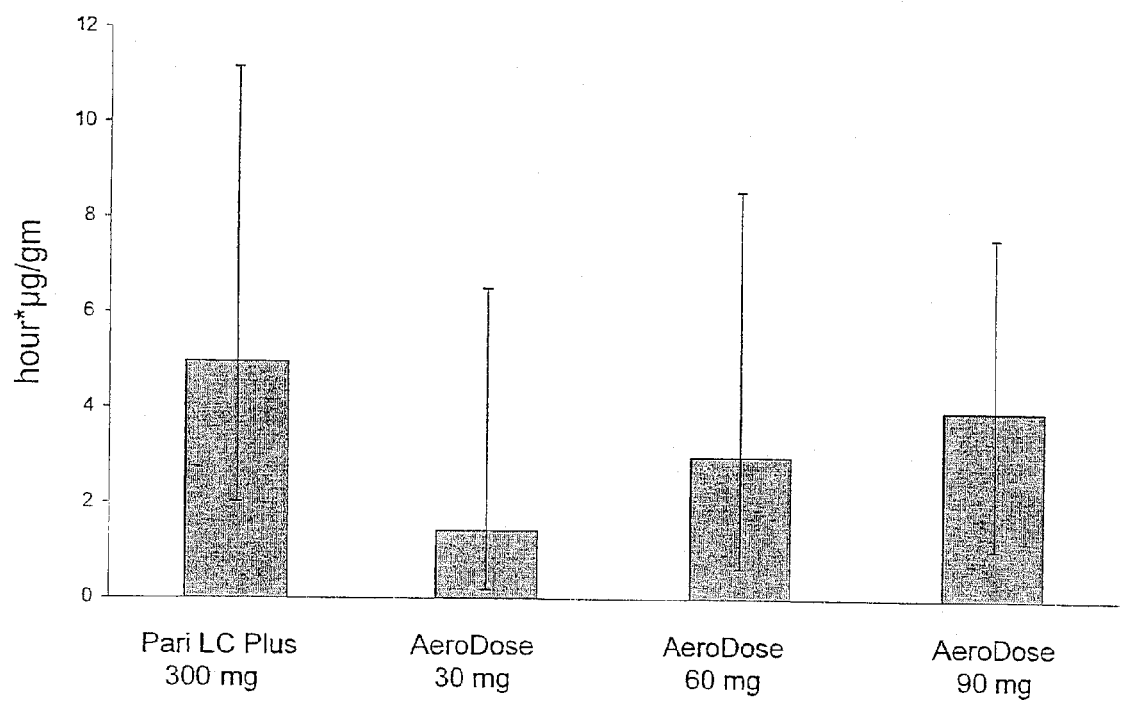

Differences among treatment groups in serum $C_{max}$ and $AUC_{0-8}$ (Table 7 above; FIGS. 6 and 7) were statistically significant (p<0.001) with no period or carryover effects in the overall analyses. In pairwise comparisons, $C_{max}$ and $AUC_{0-8}$ were significantly greater for TOBI 300 mg using the PARI LC PLUS than for TOBI 30 mg and TOBI 60 mg using the Aerodose inhaler (p<0.001 in each comparison). $C_{max}$ was statistically significantly higher (p=0.027) for TOBI 300 mg compared to the TOBI 90 mg dose, and $AUC_{0-8}$ was slightly but not significantly (p=0.165) greater for TOBI 300 mg than for TOBI 90 mg.

The Aerodose inhaler was more efficient, regardless of TOBI dose, than the PARI LC PLUS nebulizer based on dose normalized sputum $C_{max}$ and $AUC_{0-8}$ results. Dose normalized means for these pharmacokinetic parameters were similar among Aerodose treatments but approximately 3-fold higher than the dose normalized results after TOBI 300 mg delivered by the PARI LC PLUS nebulizer (Table 7).

$T_{max}$ (Table 7) was similar for the four treatments, averaging between 0.98 and 1.14 hours for Aerodose treatments and 1.05 hours for the TOBI 300 mg treatment using the PARI LC PLUS. Median $T_{1/2}$ ranged from 2.73 to 4.27 hours among the Aerodose dose levels, compared to 3.14 hours for TOBI 300 mg using the PARI LC PLUS nebulizer. Median $T_{1/2}$ results using the Aerodose inhaler appeared to decrease with increasing TOBI dose, but this was considered an artifact related to greater frequency of missing $T_{1/2}$ values (due to more BQL results) at lower TOBI dose levels.

Exploratory analyses revealed no substantial association between serum pharmacokinetic results and patient characteristics present before treatments (age, gender, body weight, pulmonary function [$FEV_1$% predicted] at screening) or emergent events after the start of treatments (device failure, occurrence of bronchospasm [decrease ≧10% in $FEV_1$ from predose to 30 minutes postdose], relative change in $FEV_1$.

Urinary Recovery of Tobramycin

Thirty-nine (39) of 49 completing patients had no measurable urine tobramycin concentrations before dosing in any of the 3 treatment periods, and 10 patients exhibited measurable predose urine tobramycin above the lower LOQ in the periods indicated in Table 8 below.

TABLE 8

MEASURABLE TOBRAMYCIN IN PREDOSE URINE SPECIMENS

| | | | Previous Period | | Measurable[b] Predose |
|---|---|---|---|---|---|
| Patient | Treatment[a] Sequence | TOBI dose (mg) | 8-24 hour Urine Tobramycin Concentration (μg/mL) | Serum $T_{1/2}$ (hr) | Tobramycin during Period Listed - Urine Tobramycin Concentration (μg/mL) |
| 103-1005 | C-1-2 | prestudy | na[d] | na[d] | Per 1 -- 3.80 |
| | | 300 | 3.92 | 4.80 | Per 2 -- 2.06 |
| | | 30 | 2.48 | not estimable | Per 3 -- 1.20 |
| 103-1039 | C-1-3 | prestudy | na[d] | na[d] | Per 1 -- 1.82 |
| | | 300 | 6.76 | 1.87 | Per 2 -- 2.58 |
| 104-1024 | C-1-3 | 300 | 5.14 | 3.16 | Per 2 -- 1.48 |
| 107-1027 | C-1-3 | prestudy | na[d] | na[d] | Per 1 -- 3.14 |
| | | 300 | 6.04 | 1.68 | Per 2 -- 1.58 |
| 104-1020 | C-2-1 | prestudy | na[d] | na[d] | Per 1 -- 1.74 |
| | | 300 | 13.40 | 2.93 | Per 2 -- 2.28 |
| | | 60 | 5.80 | 12.96 | Per 3 -- 1.30 |
| 109-1014 | C-2-3 | 60 | <1.0 | 4.06 | Per 3 -- 13.22 |
| 106-1025 | 1-C-2 | 300 | 5.14 | 3.80 | Per 3 -- 2.70 |
| 103-1012 | 2-C-3 | 300 | 2.26 | 3.63 | Per 3 -- 1.16 |

TABLE 8-continued

MEASURABLE TOBRAMYCIN IN PREDOSE URINE SPECIMENS

| | | | Previous Period | | Measurable[b] Predose |
|---|---|---|---|---|---|
| Patient | Treatment[a] Sequence | TOBI dose (mg) | 8-24 hour Urine Tobramycin Concentration (µg/mL) | Serum $T_{1/2}$ (hr) | Tobramycin during Period Listed - Urine Tobramycin Concentration (µg/mL) |
| 101-1002 | 3-C-1 | 300 | 7.82 | 3.37 | Per 3[c] -- 1.12 |
| 103-1006 | 3-C-2 | prestudy | na[d] | na[d] | Per 1 -- 2.72 |
| | | 90 | 10.10 | 3.14 | Per 2 -- 3.10 |
| | | 300 | 8.06 | 4.48 | Per 3 -- 2.08 |

[a]Treatments: C = Control TOBI 300 mg using PARI LC PLUS; 1 = TOBI 30 mg using Aerodose inhaler; 2 = TOBI 60 mg using Aerodose inhaler; 3 = TOBI 90 mg using Aerodose inhaler.
[b]Measurable tobramycin in urine: tobramycin concentration > LOQ (1.0 µg/mL).
[c]Dosing interrupted by inhaler malfunction.
[d]na = not applicable; previous urine specimens were not collected.

Table 8 shows that measurable urine tobramycin was recovered before dosing in periods 2, 3, or both for all 10 patients. Nine of the 10 patients had measurable predose urine tobramycin after TOBI 300 mg treatment during the preceding study period. One patient exhibited measurable tobramycin in both predose serum and predose urine, and these events both followed TOBI 300 mg administration during the previous period.

Although carryover effect cannot be ruled out, the overall results suggest that such an effect is unlikely. The elimination half-life in sputum ranged from 1.60 to 2.06 hours, and in serum ranged from 2.73 to 4.27 hours, with no substantial differences between the four treatments. Additionally, the amount of tobramycin excreted in urine was larger during the 0-8 hour period compared to the 8-24 hour period, consistent with the short $T_{1/2}$ of tobramycin. More importantly, in clinical Phase III studies in patients, multiple daily administrations did not result in any accumulation. Therefore it can be concluded that such carryover effect is most likely due to nonspecificity of the assay.

Consistent with the serum data, the amount of tobramycin excreted in urine was higher for TOBI 300 mg compared to TOBI 90 mg (Table 9 below). However, the percent of dose excreted in urine was 3-fold higher for the Aerodose inhaler at all dose levels (16 to 18%) as compared to the PARI LC PLUS nebulizer.

TABLE 9

MEAN (SD) URINARY RECOVERY OF TOBRAMYCIN BY TIME

| Urine Tobramycin Recovery | TOBI 300 mg PARI LC PLUS[a] (n = 49) | TOBI 30 mg Aerodose inhaler[b] (n = 34) | TOBI 60 mg Aerodose inhaler[b] (n = 32) | TOBI 90 mg Aerodose inhaler[b] (n = 32) |
|---|---|---|---|---|
| Collection Interval Before and After Dosing: | | | | |
| 12-0 hr predose | 305.1 | 122.8 | 67.9 | 615.5 |
| (µg) | (1412.0) | (340.7) | (192.8) | (3202.5) |
| No. pts with data | 48 | 33 | 32 | 31 |
| 0-8 hr postdose | 15003.0 | 4835.6 | 8490.3 | 12304.8 |
| (µg) | (7116.2) | (2649.6) | (3159.6) | (5352.7) |
| No. pts with data | 48 | 34 | 32 | 32 |
| Dose-normalized | 50.0 | 161.2 | 141.5 | 136.7 |
| (µg)/mg | (23.7) | (88.3) | (52.7) | (59.5) |
| No. pts with data | 48 | 34 | 32 | 32 |
| E/C (90% CIs)[d]: | | | | (2.50, 3.62) |
| 8-24 hr postdose | 3072.1 | 794.1 | 1367.4 | 2095.2 |
| (µg) | (2271.2) | (853.1) | (1118.8) | (1818.7) |
| No. pts with data | 47 | 34 | 31 | 31 |
| Dose-normalized | 10.2 | 26.5 | 22.8 | 23.3 |
| (µg)/mg | (7.6) | (28.4) | (18.6) | (20.2) |
| No. pts with data | 47 | 34 | 31 | 31 |
| E/C (90% CIs)[d]: | | | | (2.44, 3.48) |
| Total 0-24 hour | 18113.2 | 5629.7 | 9802.7 | 14588.1 |
| (µg) | (8303.4) | (2993.6) | (3771.0) | (6044.9) |
| No. pts with data | 46 | 34 | 31 | 31 |
| Dose-normalized | 60.4 | 187.7 | 163.4 | 162.1 |
| (µg)/mg | (27.7) | (99.8) | (62.8) | (67.2) |
| No. pts with data | 46 | 34 | 31 | 31 |
| E/C (90% CIs)[d]: | | | | (2.23, 3.27) |

TABLE 9-continued

MEAN (SD) URINARY RECOVERY OF TOBRAMYCIN BY TIME

| Urine Tobramycin Recovery | TOBI 300 mg PARI LC PLUS[a] (n = 49) | TOBI 30 mg Aerodose inhaler[b] (n = 34) | TOBI 60 mg Aerodose inhaler[b] (n = 32) | TOBI 90 mg Aerodose inhaler[b] (n = 32) |
|---|---|---|---|---|
| Percent of Dose Excreted (%)[c] | 6.0 | 18.8 | 16.3 | 16.2 |

[a]Control (C) treatment = TOBI 300 mg delivered by PARI LC PLUS nebulizer.
[b]Experimental (E) treatments = TOBI 30, 60, or 90 mg delivered by Aerodose inhaler.
[c]% excreted = [(urinary recovery in μg ÷ 1000 μg/mg) ÷ Dose in mg] · 100%.
Urine limit of quantifiability (LOQ): 1.0 μg/mL urine.

Figure 8:
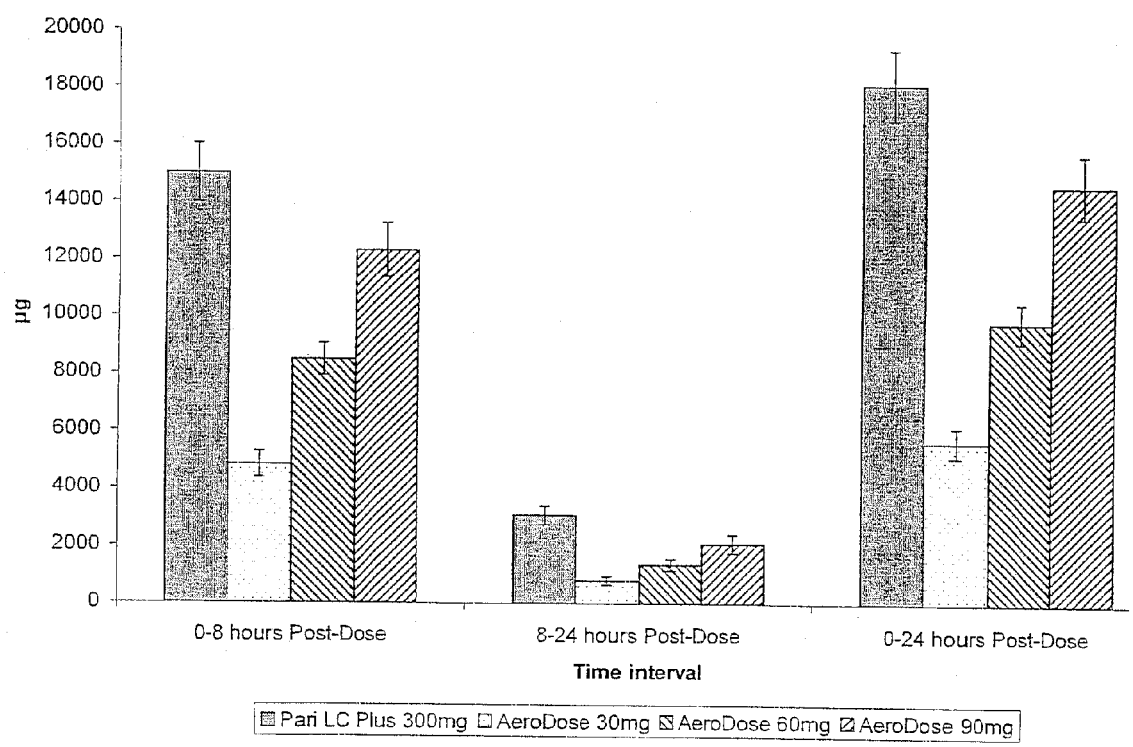
FIG. 8 is a graphical representation showing the mean recovery of tobramycin from urine 0-8, 8-24 and 0-24 hours post dosing with the formulations of FIG. 1, as described in Example 1.

For the Aerodose inhaler, mean 24-hour recovery of tobramycin from the urine increased with increasing TOBI dose during the study (Table 9 above; FIG. 8). Tobramycin recovery appeared to be dose proportional for the Aerodose inhaler, as mean 24-hour recovery normalized for dose was similar among Aerodose treatments.

Comparing devices, mean recovery for the TOBI 90 mg treatment was less than that seen for TOBI 300 mg using the PARI LC PLUS nebulizer. However, a greater percentage of the administered TOBI dose was recovered in the urine of patients who were dosed with the Aerodose inhaler (18.8%, 16.3%, and 16.2%, respectively), irrespective of TOBI dose, than was recovered from patients who were dosed with the PARI LC PLUS nebulizer (6.0% of the administered TOBI 300 mg dose).

The largest amount of tobramycin was recovered during the first 8 hours after dosing. There was no apparent pattern of period-to-period change in posttreatment urine tobramycin recovery for any of the 4 treatments. Although a potential carryover could not be ruled out in approximately 20% of the patients due to recovery of measurable tobramycin in predose urine, there was no clear indication of the presence of a carryover (treatment by period interaction) effect in posttreatment results.

The percent of administered dose recovered in urine over 24 hours postdose does not represent the delivered dose in the lung or absolute bioavailability. It is understood that a substantial amount of lung deposited dose still remains in the body at 24 hours postdose.

Nebulization Time

Figure 9:
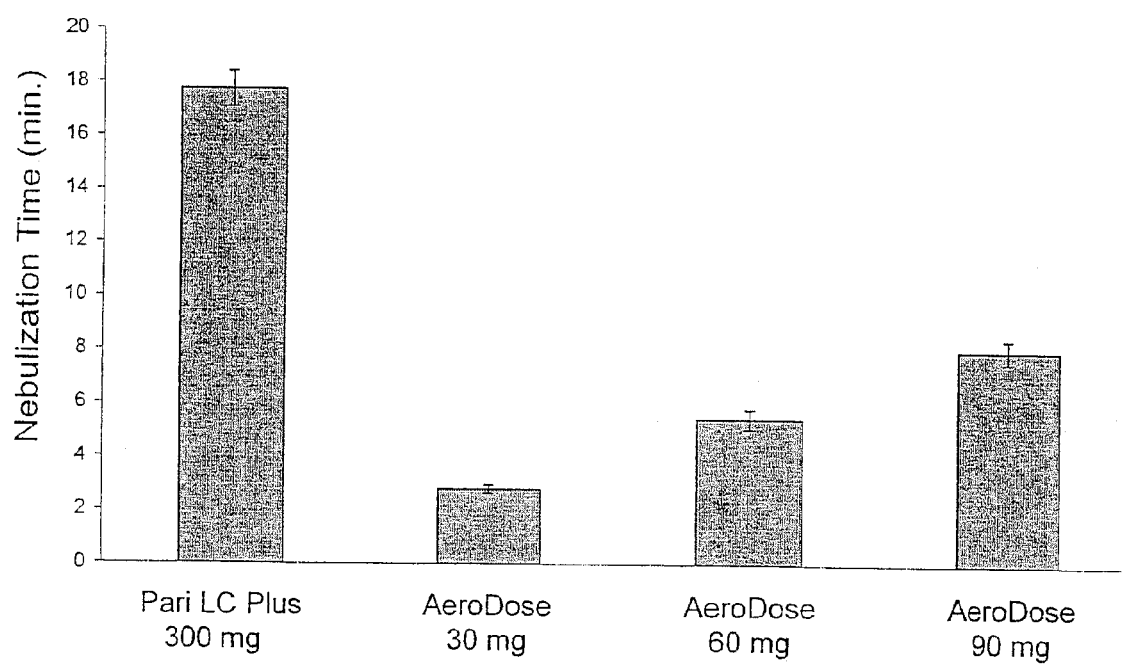
FIG. 9 is a graphical representation showing the mean nebulization time in minutes for dosing with the formulations of FIG. 1, as described in Example 1.

Mean total nebulization time increased with increasing TOBI dose (Table 10 below; FIG. 9) and was substantially less when the Aerodose inhaler was used at each TOBI dose level (mean ±SD for TOBI 30 mg=2.8±1.0 min; TOBI 60 mg=5.4±2.1 min; TOBI 90 mg=8.0±2.5 min) than when the PARI LC PLUS nebulizer was used (TOBI 300 mg=17.7±4.7 min).

Conclusions

The Aerodose inhaler substantially reduced the amount of time required to nebulize the administered TOBI dose, compared to the approved PARI LC PLUS nebulizer, and nebulization time increased with increasing TOBI dose (TOBI 300 mg delivered by PARI LC PLUS mean=17.7 minutes vs. 2.8 minutes, 5.4 minutes, and 8.0 minutes for TOBI 30 mg, 60 mg, and 90 mg, respectively).

Sputum tobramycin concentrations throughout the 8-hour sampling period after dosing increased with increasing TOBI dose through 90 mg delivered by the Aerodose inhaler, but results for TOBI 90 mg and TOBI 300 mg delivered by the PARI LC PLUS nebulizer did not differ substantially or consistently. Sputum tobramycin results were highly variable, with coefficients of variation approaching or exceeding 100% for each treatment at all time points. On average, sputum concentrations reached their maximum at 10 minutes after each of the 4 treatments. By 2 hours after TOBI 30 mg and by 8 hours after TOBI 60 mg, 90 mg, and 300 mg, sputum concentrations were below the lower limit of quantifiability (LOQ) in at least half of the patients.

The mean of the maximum sputum concentration was significantly greater after TOBI 300 mg (mean=985.65 μg/gm) than after TOBI 30 mg (329.05 μg/gm: p<0.001) and TOBI 60 mg (577.83 μg/gm: p=0.002) but not TOBI 90 mg (958.00 μg/gm: p=0.856; 90% CIs for the ratio of TOBI 90 mg/TOBI 300 mg $C_{max}$=0.72, 1.30). The Aerodose inhaler was more efficient than the PARI LC PLUS nebulizer based on sputum $C_{max}$ results adjusted for TOBI dose administered (TOBI 300 mg with PARI LC PLUS: dose-normalized mean $C_{max}$=3.29 (μg/gm)/mg; TOBI 30, 60, and 90 mg with Aerodose=10.97, 9.63, and 10.64 (μg/gm)/mg, respectively).

Mean sputum $T_{max}$ was virtually identical for TOBI 300 mg (mean=0.26 hr) and TOBI 30 mg (0.24 hr) but was slightly less than $T_{max}$ for TOBI 60 mg (0.38 hr) and TOBI 90 mg (0.33 hr).

TABLE 10

MEAN (SD) NEBULIZATION TIME

| Parameter | TOBI 300 mg PARI LC PLUS[1] (n = 51) | TOBI 30 mg Aerodose inhaler[2] (n = 34) | TOBI 60 mg Aerodose inhaler[2] (n = 32) | TOBI 90 mg Aerodose inhaler[2] (n = 33) |
|---|---|---|---|---|
| Nebulization Time[3] (min) | 17.7 (4.7) | 2.8 (1.0) | 5.2 (2.1) | 8.0 (2.5) |
| No. pts with data | 51 | 34 | 32 | 32 |

[1]Control (C) treatment = TOBI 300 mg delivered by PARI LC PLUS nebulizer.
[1]Experimental (E) treatments = TOBI 30, 60, or 90 mg delivered by Aerodose inhaler.
[2]Total duration of nebulization excluding fill time.

Mean sputum $AUC_{0-8}$ was significantly greater after TOBI 300 mg (mean=1471.16 hr·μg/gm) than after TOBI 30 mg (360.79 hr·μg/gm: p<0.001) and TOBI 60 mg (804.78 hr·μg/gm: p<0.001) but not TOBI 90 mg (1275.23 hr·μg/gm: p=0.465; 90% CIs for the ratio of TOBI 90 mg/TOBI 300 mg $AUC_{0-8}$=0.72, 1.14). The greater efficiency of the Aerodose inhaler was also seen in dose-normalized $AUC_{0-8}$ results (TOBI 300 mg with PARI LC PLUS=4.90 [hr·μg/gm]1 mg; TOBI 30, 60, and 90 mg with Aerodose=12.03, 13.41, and 14.17 [hr·μg/gm]/mg, respectively).

No inferential analyses of sputum $AUC_{0-\infty}$ were performed due to high variability that increased with increasing TOBI dose.

Serum tobramycin concentrations also increased with increasing TOBI dose at each time during the 8-hour post-treatment observation period. Mean serum tobramycin concentrations reached their maximum at one hour after each treatment. By 4 hours after TOBI 30 mg and by 8 hours after TOBI 60 mg and TOBI 90 mg, serum concentrations were below LOQ in at least half of the patients. More than half of the TOBI 300 mg patients remained above the serum LOQ at 8 hours posttreatment.

Mean serum $C_{max}$ was significantly greater after TOBI 300 mg (mean=1.12 μg/mL) than after the other 3 treatments (TOBI 30 mg=0.38 μg/mL, p<0.001; TOBI 60 mg=0.69 μg/mL, p<0.001; TOBI 90 mg=0.96 μg/mL, p=0.027). The Aerodose inhaler was also more efficient than the PARI LC PLUS nebulizer based on serum $C_{max}$ results adjusted for TOBI dose administered (TOBI 300 mg with PARI LC PLUS: dose-normalized mean $C_{max}$=0.0037 (μg/mL)/mg; TOBI 30, 60, and 90 mg with Aerodose=0.0127, 0.0116, and 0.0106 (μg/mL)/mg, respectively.

Mean serum $T_{max}$ was similar for the 4 treatments (mean=1.05 hr, 1.02 hr, 0.98 hr, and 1.14 hr for TOBI 300 mg, 30 mg, 60 mg, and 90 mg, respectively).

Mean serum $AUC_{0-8}$ was significantly greater after TOBI 300 mg (mean=4.96 hr·μg/mL) than after TOBI 30 mg (1.43 hr·μg/mL, p<0.001) and TOBI 60 mg (2.98 hr·μg/mL, p<0.001) but not TOBI 90 mg (3.94 hr·μg/mL, p=0.165; 90% CIs for the ratio of TOBI 90 mg/TOBI 300 mg $AUC_{0-8}$=0.75, 1.03). The greater efficiency of the Aerodose inhaler was also seen in dose-normalized $AUC_{0-8}$ results (TOBI 300 mg with PARI LC PLUS=0.0166 [hr·μg/mL]/mg; TOBI 30, 60, and 90 mg with Aerodose=0.0478, 0.0496, and 0.0438 [hr·μg/mL]/mg, respectively).

Serum $AUC_{(0-\infty)}$ was not analyzed statistically due to high variability but generally appeared to increase as the TOBI dose increased.

Recovery of tobramycin from the urine within 24 hours after dosing increased with increasing TOBI dose during the study (expressed in mg [mg=μg/1000], mean urine tobramycin recovery=18.1 mg, 5.6 mg, 9.8 mg, and 14.6 mg after TOBI 300 mg, TOBI 30 mg, TOBI 60 mg, and TOBI 90 mg doses, respectively). Most of the tobramycin was recovered within the first 8 hours after dosing. Normalized for dose, urine tobramycin recovery within 24 hours was 6.0%, 18.8%, 16.3%, and 16.2% of the administered TOBI 300 mg, TOBI 30 mg, TOBI 60 mg, and TOBI 90 mg doses, respectively.

Results of the present study showed that TOBI 300 mg delivered by the PARI LC PLUS nebulizer (the control delivery system) and TOBI 30 mg, 60 mg, and 90 mg delivered by the Aerodose inhaler (the experimental delivery system) were safe and well-tolerated by male and female cystic fibrosis patients. Fifteen patients (9 male and 6 female) experienced 24 instances of bronchospasm (decline in $FEV_1$ (liters) ≧10%). There were no statistically significant differences between control and any experimental treatment in the incidence of bronchospasm. There were no overall treatment differences in quantitative change in $FEV_1$ from predose to 30-minute postdose measurement times.

The study found no evidence that CF patients were at increased risk by reason of inhaling single TOBI doses of 30 mg, 60 mg or 90 mg compared to the single TOBI 300 mg dose delivered by the PARI LC PLUS jet nebulizer. The most frequently reported treatment emergent adverse events (cough increased, rhinitis, sputum increased, chest pain, asthma, and headache) and the SAEs reported by 4 of the patients were primarily associated with patients' underlying CF disease and related medical conditions. The incidence of these events before and after study treatments was substantially similar, suggesting that neither TOBI dose levels nor control and experimental inhalers altered ongoing symptomatology associated with patients' underlying medical conditions. There were also no clinically significant safety issues reflected in clinical laboratory test results, vital signs, or physical findings.

In this example, the Aerodose inhaler substantially reduced the time required for nebulization of all three dose levels (30 mg, 60 mg, and 90 mg) of TOBI compared to the nebulization time for the approved TOBI 300 mg delivery system using the PARI LC PLUS jet nebulizer. Average nebulization times were 2.8, 5.4, and 8.0 minutes using the Aerodose inhaler to deliver TOBI 30 mg, 60 mg, and 90 mg, respectively vs. 17.7 minutes using the PARI LC PLUS nebulizer to deliver TOBI 300 mg. The Aerodose inhaler therefore cut nebulization time of the TOBI 90 mg dose by more than 50% compared to the PARI LC PLUS nebulizer in the present study, and nebulization times for lower TOBI doses were reduced by even greater amounts. Present nebulization time results in CF patients ≧12 years of age with baseline $FEV_1$% predicted ≧40% were consistent with those obtained after single doses of TOBI 60 mg using the Aerodose inhaler (mean=5.7 minutes) but slightly less than TOBI 300 mg results using the PARI LC PLUS nebulizer (mean=20.4 minutes) in the TOBI gamma scintigraphy study of tobramycin deposition in the lungs of healthy adult male and female volunteers of Example 2, infra.

This example demonstrates that TOBI 90 mg (but not TOBI 60 mg or TOBI 30 mg) delivered by the Aerodose inhaler achieved similar actual pulmonary deposition, systemic absorption, and urinary recovery of tobramycin as that achieved by administration of the TOBI 300 mg dose delivered by the PARI LC PLUS nebulizer. Normalized for TOBI dose, the Aerodose inhaler was substantially more efficient than the PARI LC PLUS nebulizer in the delivery of aerosolized tobramycin to the lungs and to the systemic circulation.

Pulmonary deposition of tobramycin was measured by determination of sputum tobramycin concentrations and by calculation of sputum pharmacokinetic parameters. Maximum sputum tobramycin concentrations were reached by 10 minutes after administration of each treatment, and concentrations were below the LOQ in half or more of the patients at 2 hours after TOBI 30 mg and at 8 hours after TOBI 60 mg, 90 mg, and 300 mg. The extent of pulmonary deposition of tobramycin, as measured by maximum sputum concentrations and sputum $AUC_{0-8}$ results, increased with increasing TOBI dose through 90 mg, but TOBI 90 mg and TOBI 300 mg did not differ statistically (mean sputum $C_{max}$=958.00 and 985.65 μg/gm; mean sputum $AUC_{0-8}$=1275.23 and 1471.16 hr·μg/gm, respectively). Mean sputum $C_{max}$ results after TOBI 30 mg and 60 mg doses were significantly less than that of the TOBI 300 mg dose. Present sputum $C_{max}$ results achieved after the single TOBI 300 mg dose were slightly less than sputum tobramycin concentrations achieved 10 minutes after a single TOBI 300 mg dose (mean sputum tobramycin concentration=1237 µg/gm, median=1090 µg/gm) in two large previously conducted Phase III pivotal trials.

The results of this example demonstrate that at least one of the three TOBI doses (TOBI 90 mg) delivered by the experimental Aerodose inhaler achieved similar actual sputum tobramycin concentrations and that these results in turn were similar to sputum results obtained in the prior pivotal studies supporting the commercial TOBI product. It is also important that present sputum results demonstrated that the experimental Aerodose inhaler was substantially more efficient, regardless of TOBI dose, in delivery of aerosolized tobramycin to the lung than the PARI LC PLUS jet nebulizer. Dose-normalized sputum $C_{max}$ was 10.97, 9.63, and 10.64 (µg/gm)/mg for TOBI 30 mg, 60 mg, and 90 mg delivered by Aerodose inhaler, respectively, compared to 3.29 (µg/gm)/mg for TOBI 300 mg delivered by PARI LC PLUS. Similarly, dose-normalized sputum $AUC_{0-8}$ was 12.03, 13.41, and 14.17 [hr·µg/gm]/mg for TOBI 30 mg, 60 mg, and 90 mg delivered by Aerodose inhaler, respectively, compared to 4.90 [hr·µg/gm]/mg for TOBI 300 mg delivered by PARI LC PLUS.

Systemic absorption of tobramycin was measured by determination of serum tobramycin concentrations and by calculation of serum pharmacokinetic parameters. Maximum serum tobramycin concentrations were reached at one hour after each of the four TOBI treatments, and concentrations were below LOQ in half or more of the patients by 4 hours after TOBI 30 mg and by 8 hours after TOBI 60 mg and 90 mg. More than half of the patients at TOBI 300 mg had measurable serum tobramycin at 8 hours postdose. The extent of absorption of tobramycin, as measured by serum $C_{max}$ results, increased with increasing TOBI dose, as $C_{max}$ was significantly greater after TOBI 300 mg (mean=1.12 µg/mL) than after each of the lower TOBI doses (mean=0.38, 0.69, and 0.96 µg/mL for TOBI 30 mg, 60 mg, and 90 mg doses, respectively). Serum $C_{max}$ for TOBI 300 mg in the present study was slightly higher (mean ±SD=1.10±0.44 µg/mL with a mean $T_{max}$ of 1.05 hr) than the mean serum tobramycin concentration reported at one hour after TOBI 300 mg in the TOBI NDA (0.95±0.50 µg/mL). Serum $C_{max}$ achieved by the Aerodose inhaler at the TOBI 90 mg dose level in the current study was virtually identical to the NDA serum concentrations one hour after TOBI 300 mg (mean=0.96±0.37 µg/mL), although it was significantly (p=0.027) less than the current TOBI 300 mg.

Thus, present serum tobramycin results demonstrated that TOBI 90 mg delivered by the Aerodose inhaler were similar ($AUC_{0-8}$) or nearly similar ($C_{max}$) to those obtained after TOBI 300 mg delivered by the PARI LC PLUS nebulizer in the present study and in the prior pivotal studies supporting the TOBI commercial product. Present serum results also demonstrated that the experimental Aerodose inhaler was substantially more efficient, regardless of TOBI dose, in delivery of aerosolized tobramycin to the systemic circulation than the PARI LC PLUS jet nebulizer. Dose-normalized serum $C_{max}$ was 0.0127, 0.0116, and 0.0106 (µg/mL)/mg for TOBI 30 mg, 60 mg, and 90 mg delivered by Aerodose inhaler, respectively, compared to 0.0037 (µg/mL)/mg for TOBI 300 mg delivered by PARI LC PLUS. Similarly, dose-normalized serum $AUC_{0-8}$ was 0.0478, 0.0496, and 0.0438 [hr·µg/mL]/mg for TOBI 30 mg, 60 mg, and 90 mg delivered by Aerodose inhaler, respectively, compared to 0.0166 [hr·µg/mL]/mg for TOBI 300 mg delivered by PARI LC PLUS. The greater efficiency of the Aerodose inhaler observed in present serum tobramycin results is consistent with greater efficiency and less wastage of the tobramycin dose observed in earlier studies.

Urinary recovery of tobramycin was measured by determining the cumulative amount of tobramycin recovered in urine collected for 24 hours after dosing. The amount of urinary tobramycin recovered within 24 hours postdose increased with increasing TOBI dose (expressed in mg [mg=µg/1000], mean urine tobramycin recovery=5.6 mg, 9.8 mg, 14.6 mg, and 18.1 mg tobramycin after TOBI 30 mg, 60 mg, 90 mg, and 300 mg). The results were not tested statistically, and it was not possible to determine whether TOBI 90 mg and TOBI 300 mg results for 24-hour recovery of urine tobramycin were similar or different.

Normalized for dose by dividing the mean amount of tobramycin recovered by the nominal amount of TOBI administered, urinary recovery of tobramycin was approximately 18.8%, 16.3%, 16.2%, and 6.0% of the administered TOBI 30 mg, 60 mg, 90 mg, and 300 mg doses, respectively.

During the study, measurable tobramycin (i.e., above the lower limit of quantifiability [LOQ] of the assay) was detected in 12-hour predose urine collections in a total of 10 patients, including 5 patients before the first dose of study treatments in period one and all 10 patients before the second or third doses in periods 2 and 3 or both. Similarly, measurable tobramycin was detected in predose serum specimens in a total of 5 patients, including 3 patients before the first dose of study treatments in period one and 4 patients before dosing in periods 2, or 3, or both. A single patient had measurable tobramycin in both urine and serum.

Substantial variability is known to occur among patients in the rate and extent of uptake, renal accumulation, and elimination of aminoglycoside antibiotics, even in patients with normal renal function. Each of these factors may lengthen the amount of time that measurable concentrations of aminoglycoside antibiotics may be detected in serum and urine. The present study employed a prestudy washout interval of 7 days from previous prescription aminoglycoside antibiotic use and a 7-day interval between the 3 single doses of TOBI, an aminoglycoside antibiotic, during the crossover treatment periods. It is plausible that prestudy and on-study washout intervals in the study may have been too short for complete elimination of residual tobramycin previously administered, if any. Measurable amounts of tobramycin for these patients would have had little effect on study results, since the amounts and concentrations detected were very small in nearly all cases, and no unusually high serum or urine tobramycin results were noted during the study.

The Aerodose inhaler was a safe and efficient aerosolization and delivery device for TOBI during the study.

Example 2

Scintigraphy Study

In order to assess the in vivo lung deposition of 300 mg tobramycin (TOBI®) inhaled using the PARI LC PLUS™ jet nebulizer/DeVilbiss PulmoAide® compressor delivery system (current commercial delivery system) compared with the deposition of 60 mg tobramycin (TOBI®) using the AeroDose™ inhaler in accordance with the present invention, a gamma scintigraphy study was performed. The imaging technique of gamma scintigraphy is a well-established method[10-12] that provides precise quantification of drug delivered to the lungs[13]. It also provides an assessment of the distribution of deposited drug in different lung regions (peripheral, intermediate and central lung regions corresponding to small airways, medium sized airways and large airways, respectively[14]). Gamma scintigraphy is the only non-invasive method currently available for obtaining this type of information.

The study of this example was designed as an open label, randomized, single center, single dose, two period crossover Phase I study of aerosol delivery characteristics and safety of two inhalation devices in healthy adult volunteers. A maximum of 14 healthy male or non-pregnant, non breast-feeding female volunteers aged 18 to 65 years of age were to receive in random order two single doses of aerosolized antibiotic mixed with a sterile radiotracer (technetium bound to diethylenetriaminepentaacetic acid: $^{99m}$Tc DTPA) separated by a washout interval of a minimum of 44 hours between doses. Radiolabeled aerosols consisted of a single 300 mg dose in a 5 mL solution of TOBI delivered by the control delivery system (PARI LC PLUS jet nebulizer with a PulmoAide compressor) and a single 60 mg dose in a 1 mL solution of TOBI delivered by the experimental delivery system (Aerodose inhaler).

Aerosol delivery characteristics of control and experimental delivery systems were compared on the basis of lung deposition of radiolabeled tobramycin determined by gamma scintigraphy, time to complete nebulization of aerosolized doses, serum concentrations of tobramycin determined by Abbott TDxFLx assays, and serum tobramycin pharmacokinetic parameters.

The safety of control and experimental TOBI delivery systems was compared on the basis of changes in pulmonary function, the incidence of treatment emergent adverse events, and the occurrence of clinically significant laboratory and clinical evaluations and of unusually high serum tobramycin concentrations.

The duration of study participation for each subject was to be approximately five weeks including a screening period of up to 3 weeks in duration, two treatment periods of approximately 9 hours each separated by a minimum 44-hour washout interval, and a follow-up period through 2 weeks after the end of dosing.

Treatments

TOBI® was administered by inhalation as a single 300 mg dose and as a single 60 mg dose to each subject during the study. The 300 mg dose was supplied as a commercial ampoule of TOBI. The 60 mg dose of tobramycin solution was prepared by study site personnel by withdrawing 1.0 mL of solution from the 300 mg/5 mL commercial ampoule of TOBI into two unit dose syringes containing 0.5 mL each.

Sterile $^{99m}$Tc DTPA was added as a radiotracer to both 300 mg and 60 mg solutions at the study site prior to instillation into the nebulizer. Sufficient $^{99m}$Tc DTPA was added to both the 300 mg and the 60 mg dose so that no more than 10 MBq $^{99m}$Tc DTPA was delivered to the subject with each single dose administered.

Using control and experimental aerosol delivery systems, each subject was to self-administer two single aerosolized doses of radiolabeled ($^{99m}$Tc DTPA) TOBI, one dose in each of two crossover treatment periods, according to the randomization scheme for the study. Subjects were instructed to use nose clips and breathe in a normal breathing pattern while inhaling the medication according to the instructions for use for each inhaler.

Control and experimental treatment delivery systems were specified as follows.

Control Treatment Delivery System: PARI LC PLUS jet nebulizer with DeVilbiss PulmoAide compressor delivering 300 mg (5 mL) of TOBI.

Experimental Treatment Delivery System: Aerodose inhaler delivering 60 mg (1 mL) of TOBI.

When the PARI LC PLUS nebulizer was used, 5 mL radiolabeled TOBI was added to the drug reservoir and nebulized without interruption until the nebulizer reservoir was dry. The PARI system was configured such that exhalation by the subject did not result in escape of radioactive aerosol into the surrounding atmosphere. Exhaled droplets were collected using a filter attached to the side of the inhaler by a T-piece. In addition, a scavenger filter was placed above the inhaler, which was in turn connected to a vacuum pump. The scavenger system was used to collect any radiolabeled droplets escaping from the inhaler.

When the Aerodose inhaler was used, one 0.5 mL aliquot of radiolabeled TOBI was added to the drug reservoir and nebulized to dryness. A second 0.5 mL dose was then added to the reservoir and nebulized to dryness. The inhaler was surrounded with an exhaled air collection box. Air was drawn through a filter at the back of the box using a vacuum pump.

Start and stop times of nebulization for both the Aerodose and PARI LC PLUS nebulizers were to be recorded in CRFs. Nebulization time for the Aerodose inhaler was not to include the time needed to refill the drug reservoir according to the protocol.

Enrolled volunteers were randomly assigned to two treatment sequence groups as illustrated below according to a randomization scheme.

PARI 300 mg/Aerodose 60 mg:
- period 1: PARI LC PLUS with TOBI 300 mg
- period 2: Aerodose with TOBI 60 mg Aerodose 60 mg/PARI 300 mg:
- period 1: Aerodose with TOBI 60 mg
- period 2: PARI LC PLUS with TOBI 300 mg All subjects randomly assigned to a single treatment sequence group received control and experimental treatments in the same order during the study, while subjects assigned to the other treatment sequence group received treatments in the reverse order. Table 11 below shows the two sequences of treatment administration employed during the study via the randomization process.

TABLE 11

TREATMENT SEQUENCE GROUPS AND SEQUENCE OF TREATMENTS IN THE STUDY

| Treatment Sequence Group[1] | Treatment Period 1 | Treatment Period 2 |
|---|---|---|
| C-E[2] | C | E |
| E-C | E | C |

[1]Subjects were randomly assigned to the two treatment sequence groups.
[2]C and E refer to control and experimental treatments administered during the study as follows:
C = PARI LC PLUS jet nebulizer (60 mg/mL; 300 mg in 5 mL)
E = Aerodose inhaler (60 mg/mL; 60 mg in 1.0 mL)

Before dosing, TOBI formulations were radiolabeled with $^{99m}$Tc-DTPA in preparation for gamma scintigraphy to determine posttreatment tobramycin deposition in the lungs. Subjects practiced the inhalation procedure with both control and experimental devices filled with normal saline. When the investigator was satisfied that the subject could reproducibly perform the correct inhalation technique, the inhaler was filled with the radiolabeled formulation, and the subject inhaled the radiolabeled dose until the nebulizer was dry and nebulization was stopped.

Immediately following inhalation of radiolabeled, aerosolized tobramycin, scintigraphic images were recorded to determine radioactivity associated with lung and oropharyngeal tobramycin deposition and with external items such as nebulizer parts, mouthpieces, filters, and tissues used by subjects. If not previously done within the last 5 years, a posterior lung ventilation scan was also performed during the study after subjects inhaled the radioactive inert gas $^{81m}$Kr to determine the lung outlines and facilitate the determination of regional deposition of radiolabeled tobramycin.

Deposition of Tobramycin

Assessment and comparison of tobramycin deposition patterns between PARI LC PLUS and Aerodose delivery systems was a primary objective of the study. Deposition patterns of inhaled, radiolabeled tobramycin were determined using scintigraphic imaging methodology. Lung, oropharyngeal, and (if necessary) abdominal radioactivity was measured from images obtained immediately after inhalation of each single dose of radiolabeled tobramycin using a gamma camera (General Electric Maxicamera) with a 40 cm field of view and fitted with a low energy parallel hole collimator. Images were obtained as described below:

posterior view of the chest;
    anterior view of the chest;
    right lateral view of the oropharynx;
    anterior and posterior abdominal views if necessary, i.e., if activity had spread through the intestine, beyond the field of view in either of the chest images;
    items external to the body of the subject as follows:
        for the PARI LC PLUS system:
            nebulizer cup
            mouthpiece
            exhalation filter and T-piece
            scavenger filter
            any tissues used by the subject
        for the Aerodose system:
            Aerodose inhaler
            exhaled air containment box and filter
            any tissues used by the volunteer Additionally, a posterior lung ventilation scan was performed using the radioactive inert gas, krypton ($^{81m}$Kr), to determine the lung outlines. The lung outlines were used to divide lung images of each subject into central, intermediate, and peripheral lung zones in order to determine the amount of aerosolized tobramycin deposited in each of these zones[17]. Lung ventilation scans taken for subjects who participated in earlier studies were acceptable for use for this study provided the scan was obtained within the last five years and the subject had no record of serious lung disease in the intervening period.

Deposition zones of interest on scintigraphic images were additionally drawn around the oropharynx, esophagus, and stomach (including any activity in the small intestine). The counts obtained within all regions of interest were corrected for background radioactivity, radioactive decay, and for tissue attenuation[18]. In regions where both anterior and posterior images were recorded, the geometric mean of counts in both images was calculated prior to correction for tissue attenuation. Determination of the percentage of the dose deposited in the oropharynx included activity adhering to the mouth and oropharynx together with any swallowed activity detected in the esophagus, stomach, and intestine.

All images were recorded using Micas X plus software installed on a UNIX based computer system. Images were stored on digital audio tape (DAT) for subsequent analysis and archiving. Scintigraphic data were analyzed by Pharmaceutical Profiles Ltd. (PPL) in accordance with the PPL Standard Operating Procedure N 1013 "Lung Quantitative Data Analysis". The data were summarized to obtain the following parameters:

whole lung deposition (% of metered dose);
    central lung zone deposition (% of metered dose);
    intermediate lung zone deposition (% of metered dose);
    peripheral lung zone deposition (% of metered dose);
    ratio of peripheral to central zone deposition (lung penetration index);
    oropharyngeal deposition (including esophagus and stomach) (% of metered dose);
    inhaler deposition (PARI LC PLUS or AeroDose) (% of metered dose);
    radioaerosol in exhaled air (filters) (% of metered dose);
    radioaerosol on PARI LC PLUS mouthpiece, T-piece, scavenger filter and subject tissues (% of metered dose);
    radioaerosol on Aerodose exhaled air collection box and subject tissues (% of metered dose).

The counts in each area were expressed as a percentage of the metered dose that was determined from the sum of the total body counts in addition to those deposited on the inhaler and the exhalation filter. Since the volume of TOBI placed into each of the two inhalers was different, direct comparisons of the percentage deposition values was problematic. To aid interpretation of the data, the percentage deposition values were multiplied by the nominal metered dose (300 mg for the PARI LC PLUS and 60 mg for the Aerodose inhaler) to obtain amounts of drug deposited in milligrams for each of the deposition parameters listed above.

Nebulization Time

Assessment and comparison of nebulization time between PARI LC PLUS and Aerodose delivery systems was another objective of the study. Elapsed time from the start of nebulization (defined as the subject's first tidal breath after the inhaler was in place) until no more TOBI solution was aerosolized by the inhaler was measured by staff at the site using a stopwatch. Nebulization time was not to include time needed for instillation of drug into the nebulizer between the repeat filling of the Aerodose inhaler. The length of any interruption in nebulization and the reason for interruption were recorded.

Serum tobramycin concentrations were determined for the present study, and pharmacokinetic parameters were calculated, to provide preliminary estimates of the bioavailability of 60 mg TOBI delivered by the Aerodose system in comparison with that of the marketed 300 mg TOBI formulation. Additionally, unusually high serum tobramycin results ($\geq 4$ µg/mL) were considered an important measure of safety during the study.

Venous blood samples (8 mL) for the determination of serum tobramycin concentrations were collected by intravenous cannula or by venipuncture before each single dose of TOBI and at 30 minutes and 1, 2, 4, and 8 hours after completion of dosing. The first one mL of blood withdrawn from the cannula was discarded, and the subsequent 7 mL was withdrawn into serum sampling tubes. Cannulae were frequently flushed with saline during the course of the treatment day.

Blood samples were centrifuged at approximately 1600 g for 10 minutes at 4° C. The resulting serum fraction was split into two aliquots by pipetting into two prelabeled polypropylene screw cap tubes. Tubes were stored at −20° C. for each study period and were then transferred to a −70° C. freezer.

The maximum tobramycin concentration ($C_{max}$) and the time to reach $C_{max}$ ($T_{max}$) were the observed values. The elimination rate constant ($k_{el}$: used to calculate $AUC_{0-\infty}$; see next paragraph) was calculated as the negative slope of the log plasma concentration vs. time plot using the last two measurable concentrations. Use of more than two concentrations at or after $T_{max}$ is preferred for calculation of the elimination rate constant; however, several subjects had only two measurable tobramycin concentrations at the terminal phase after TOBI 60 mg using the Aerodose inhaler. The alternate method of calculating $k_{el}$ using the last two measurable concentrations was employed for all subjects for both period 1 and period 2.

Area under the curve through 8 hours postdose ($AUC_{0-8}$) and extrapolated to infinity ($AUC_{0-\infty}$) were calculated for serum tobramycin concentrations using the linear trapezoid rule. Actual nebulization time was added to the time between predose and 30 minutes after the end of inhalation when calculating $AUC_{0-8}$. $AUC_{0-\infty}$ was extrapolated from the last measurable concentration to infinite time by adding the quantity equal to the last measurable concentration divided by the elimination rate constant ($k_{el}$).

Statistical Methods Planned in the Protocol

Scintigraphic data were analyzed in accordance with the current version of the PPL Standard Operating Procedure N 1013 "Lung Quantitative Data Analysis". Manipulation and calculation of radioactivity counts were accomplished using a custom written region of interest program, where regions of interest were central, intermediate, peripheral, and stomach/intestines if necessary. Numerical data were downloaded automatically from the Park Medical computer into a customized spreadsheet.

Due to the small number of subjects in the study, statistical analysis was performed only on whole lung deposition data and on selected pharmacokinetic parameters. All other study data were summarized descriptively. Descriptive summaries for quantitative data included sample size, mean, standard deviation, median, minimum, maximum, and/or range values as appropriate. Descriptive summaries for qualitative or categorical data included number and percent of subjects with the characteristic. All clinical data manipulations, analyses, summaries, and transformations employed SAS version 6.12[20-22].

Aerosol Delivery Analyses

Whole lung deposition was the primary endpoint for the analysis. The Wilcoxon one-sample, matched-pairs, signed ranks test was used to determine whether differences between the whole lung deposition patterns (percent and amount of metered dose deposited) for the two inhalers were significant. The significance level was set at $\alpha=0.05$.

Serum pharmacokinetic parameters ($C_{max}$, $AUC_{0-8}$, and $AUC_{0-\infty}$) were analyzed for differences between delivery systems using a repeated measures analysis of variance. The statistical model included study period and delivery systems as fixed effects and subject as the random effect. The carry-over effect from treatment period 1 to 2 was also investigated. The significance level was set at $\alpha=0.05$, and tests of significance were two-sided.

Additional deposition measures of interest, nebulization time, serum tobramycin concentrations and pharmacokinetic parameters were summarized and evaluated descriptively for apparent differences between aerosol delivery systems.

Study Drug Administration

All subjects were successfully dosed according to the randomization schedule for the study, and all subjects received and completed both inhalation administrations. All subjects received single doses of TOBI 300 mg and TOBI 60 mg during the study.

Deposition of Radiolabeled Tobramycin

Tobramycin deposition results indicated that the Aerodose system was more efficient than the PARI LC PLUS system. The Aerodose system with TOBI 60 mg delivered a greater percentage of the dose to the lungs (mean ±SD=34.8±10.1%) than the PARI system with TOBI 300 mg (8.2±3.6%), and the difference was statistically significant (p=0.005) (see Table 12 below). Results from the analysis (n=9) that excluded data from one patient were similar (means=35.4% vs. 9.1% for Aerodose and PARI systems, respectively; p=0.008).

The actual amount of drug delivered to the lungs (Table 13 below) was slightly but not significantly less (p=0.202) using the Aerodose inhaler (20.9±6.0 mg) than using the PARI inhaler (24.5±10.7 mg). Excluding subject 1007, the analysis showed significantly less (p=0.04) deposition of the Aerodose 60 mg dose (21.2 mg) than the PARI 300 mg dose (27.2 mg).

TABLE 12

MEAN (SD) PERCENTAGE DEPOSITION OF THE METERED TOBI DOSE

| Zone of Deposition | Intent to Treat (n = 10) | | Excluding Subject 1007 (n = 9) | | p-value* |
|---|---|---|---|---|---|
| | TOBI 300 mg PARI LC PLUS | TOBI 60 mg AeroDose | TOBI 300 mg PARI LC PLUS | TOBI 60 mg AeroDose | |
| Whole lung | 8.2 (3.6)* | 34.8 (10.1)* | 9.1 (2.2) | 35.4 (10.5) | 0.005 |
| central | 2.4 (1.2) | 10.1 (4.0) | 2.7 (0.9) | 10.2 (4.2) | |
| intermediate | 2.7 (1.2) | 11.6 (3.6) | 3.0 (0.8) | 11.8 (3.7) | |
| peripheral | 3.1 (1.3) | 13.2 (3.4) | 3.5 (0.7) | 13.4 (3.5) | |
| ratio: peripheral/central | 1.2 (0.5) | 1.4 (0.4) | 1.4 (0.3) | 1.4 (0.4) | |
| Oropharynx (including esophagus and stomach) | 14.4 (6.7) | 31.5 (11.6) | 16.0 (4.7) | 31.5 (12.3) | |
| Inhaler | 42.6 (6.7) | 15.2 (8.4) | 43.5 (6.4) | 15.1 (8.9) | |
| Exhalation filter | 31.6 (10.9) | 16.9 (5.6) | 28.3 (2.7) | 16.3 (5.6) | |
| PARI-specific: | | | | | |
| mouthpiece | 1.0 (0.5) | | 1.0 (0.5) | | |
| T-piece | 2.0 (0.6) | | 2.0 (0.5) | | |
| tissue | 0.0 (0.1) | | 0.0 (0.1) | | |
| scavenger filter | 0.1 (0.1) | | 0.1 (0.1) | | |

TABLE 12-continued

MEAN (SD) PERCENTAGE DEPOSITION OF THE METERED TOBI DOSE

| | Intent to Treat (n = 10) | | Excluding Subject 1007 (n = 9) | | |
|---|---|---|---|---|---|
| Zone of Deposition | TOBI 300 mg PARI LC PLUS | TOBI 60 mg AeroDose | TOBI 300 mg PARI LC PLUS | TOBI 60 mg AeroDose | p-value* |
| AeroDose-specific: | | | | | |
| box | | 1.7 (1.5) | | 1.6 (1.6) | |
| tissue | | 0.0 (0.1) | | 0.0 (0.1) | |

*Wilcoxon matched-pairs signed ranks test on intent to treat dataset. Excluding Subject 1007: p = 0.008. Statistical significance: p ≦0.05.

The Aerodose inhaler deposited proportionally more (Table 12 above) tobramycin in the lungs than in the oropharynx (mean 34.8% vs. 31.5% of the 60 mg dose), while the PARI LC PLUS nebulizer deposited less tobramycin in the lungs than in the oropharynx (mean 8.2% vs. 14.4% of the 300 mg dose). The ratio of lung to oropharyngeal deposition (whole lung deposition divided by oropharynx deposition in Table 12 above) was approximately 1.1 for the Aerodose inhaler compared to approximately 0.6 for the PARI LC PLUS nebulizer.

Regional deposition within the lung was predominantly peripheral and very similar for both inhalers (ratio of radioactivity in peripheral to central zones: Aerodose=1.4±0.4; PARI LC PLUS=1.2±0.5).

Substantially less tobramycin was deposited on the Aerodose inhaler (15.2±8.4%; 9.1±5.1 mg; Tables 4 and 5, respectively) and exhalation filter (16.9±5.6%; 10.1±3.3 mg) than on the PARI LC PLUS nebulizer (42.6±6.7%; 127.8±20.0 mg) and filter (31.6±10.9%; 94.8±32.7 mg). No more than 2% of the metered dose was deposited on inhaler-specific surfaces or tissue paper used by subjects.

Nebulization Time

The nebulization time (i.e., time required from first tidal breath until the nebulizer ran dry) was significantly shorter (p=0.005) for the Aerodose delivery system (mean ±SD=5.70±1.16 minutes) than for the PARI LC PLUS system (20.40±3.47 minutes) (Table 14 below).

TABLE 14

MEAN (SD) NEBULIZATION TIME

| Nebulization Time* Parameter | Intent to Treat (n = 10) | | |
|---|---|---|---|
| Nebulization Time (minutes): | TOBI 300 mg PARI LC PLUS | TOBI 60 mg AeroDose | p-value |
| Mean | 20.40 | 5.70 | 0.005 |
| SD | 3.47 | 1.16 | |
| Minimum | 17.0 | 4.0 | |
| Maximum | 29.0 | 8.0 | |
| no. subjects | 10 | 10 | |

TABLE 13

MEAN (SD) AMOUNT (MG) OF DEPOSITION OF THE METERED TOBI DOSE

| | Intent to Treat (n = 10) | | Excluding Subject 1007 (n = 9) | | |
|---|---|---|---|---|---|
| Zone of Deposition | TOBI 300 mg PARI LC PLUS | TOBI 60 mg AeroDose | TOBI 300 mg PARI LC PLUS | TOBI 60 mg AeroDose | p-value* |
| Whole lung | 24.5 (10.7)* | 20.9 (6.0)* | 27.2 (6.7) | 21.2 (6.3) | 0.202 |
| central | 7.3 (3.6) | 6.0 (2.4) | 8.0 (2.8) | 6.1 (2.5) | |
| intermediate | 8.0 (3.7) | 6.9 (2.1) | 8.9 (2.5) | 7.1 (2.2) | |
| peripheral | 9.3 (3.8) | 7.9 (2.1) | 10.4 (2.0) | 8.1 (2.1) | |
| Oropharynx (including esophagus and stomach) | 43.3 (20.2) | 18.9 (6.9) | 48.1 (14.0) | 18.9 (7.4) | |
| Inhaler | 127.8 (20.0) | 9.1 (5.1) | 130.5 (19.2) | 9.0 (5.4) | |
| Exhalation filter | 94.8 (32.7) | 10.1 (3.3) | 84.8 (8.1) | 9.8 (3.4) | |
| PARI-specific: | | | | | |
| mouthpiece | 3.0 (1.4) | | 3.1 (1.5) | | |
| T-piece | 6.1 (1.7) | | 5.9 (1.6) | | |
| tissue | 0.1 (0.2) | | 0.1 (0.2) | | |
| scavenger filter | 0.4 (0.4) | | 0.4 (0.4) | | |
| AeroDose-specific: | | | | | |
| box | | 1.0 (0.9) | | 1.0 (0.9) | |
| tissue | | 0.0 (0.1) | | 0.0 (0.1) | |

*Wilcoxon matched-pairs signed ranks test on intent to treat dataset. Excluding Subject 1007: p = 0.04. Statistical significance: p ≦0.05.

Serum Tobramycin Concentrations and Pharmacokinetic Parameters

Administration of TOBI 300 mg using the PARI LC PLUS delivery system produced higher mean serum tobramycin concentrations, a higher mean $C_{max}$, and a greater $AUC_{(0-8)}$ than administration of TOBI 60 mg using the Aerodose delivery system. The mean time to maximum tobramycin concentration ($T_{max}$) was similar for the two delivery systems.

Serum tobramycin concentrations for all subjects were below quantifiable limits before dosing in both period 1 and period 2. FIGS. 1 through 20 graphically illustrate serum tobramycin concentrations before and after period 1 and period 2 dosing for all individual subjects.

After dosing, two subjects had serum tobramycin concentrations that could not be measured (i.e., results were below the quantifiable limit of 0.20 µg/mL) during one of the two treatment periods. These two subjects were inevaluable for pharmacokinetic analysis during the period indicated but provided evaluable results for the alternate period.

Consistent with the high efficiency of the Aerodose system, mean serum tobramycin concentrations were slightly lower throughout the 8-hour postdose observation period after delivery of TOBI 60 mg using the Aerodose system than after delivery of TOBI 300 mg using the PARI LC PLUS system (Table 15 below). Maximum plasma concentrations for both regimens were reached within 2 hours after the end of inhalation (TOBI 300 mg and PARI inhaler: 1 hr and 2 hr means=0.63 µg/mL; TOBI 60 mg and Aerodose inhaler: 2 hr mean=0.48 µg/mL). By 8 hours after the end of inhalation, the plasma concentrations were below the limit of quantitation in 5 subjects after the Aerodose inhaler and in two subjects after the PARI LC PLUS nebulizer.

TABLE 15

SERUM TOBRAMYCIN CONCENTRATIONS
AND PHARMACOKINETIC PARAMETERS

| | Intent to Treat (n = 10) | |
|---|---|---|
| Parameter* | TOBI 300 mg PARI LC PLUS[a] | TOBI 60 mg AeroDose[b] |
| Serum Tobramycin (µg/mL): Time Before and After Dosing: | | |
| Predose | 0.00 (0.00) 9 | 0.00 (0.00) 9 |
| 30 minutes | 0.42 (0.24) 9 | 0.22 (0.23) 9 |
| 1 hour | 0.63 (0.29) 9 | 0.41 (0.22) 9 |
| 2 hours | 0.63 (0.25) 9 | 0.48 (0.20) 9 |
| 4 hours | 0.50 (0.16) 9 | 0.38 (0.10) 9 |
| 8 hours | 0.22 (0.14) 9 | 0.13 (0.12) 9 |
| Pharmacokinetic Parameters: | | |
| $C_{max}$ (µg/mL) | 0.677 (0.279) 9 | 0.482 (0.201) 9 |
| $T_{max}$ (hr) | 2.213 (0.923) 9 | 2.207 (0.788) 9 |
| $T_{1/2}$ (hr) | 4.269 (1.058) 9 | 6.071 (3.357) 9 |
| $AUC_{(0-8)}$ (µg/mL · hr) | 3.622 (1.319) 9 | 2.553 (0.989) 9 |
| $AUC_{(0-\infty)}$ (µg/mL · hr) | 5.273 (1.699) 9 | 4.630 (0.967) 9 |
| Pharmacokinetic Parameters Normalized to Dose: | | |
| $C_{max}$ (µg/mL)/mg | 0.002 (0.001) 9 | 0.008 (0.003) 9 |
| $AUC_{(0-8)}$ (µg/mL · hr)/mg | 0.012 (0.004) 9 | 0.043 (0.016) 9 |
| $AUC_{(0-\infty)}$ (µg/mL · hr)/mg | 0.018 (0.006) 9 | 0.077 (0.016) 9 |

*Cell entries are mean, (SD), no. of subjects.
[a]TOBI 300 mg summary statistics exclude BQL results for Subject 1007 throughout period 2.
[b]TOBI 60 mg summary statistics exclude BQL results for Subject 1006 throughout period 1.

Pharmacokinetic Results

The mean of the maximum tobramycin concentrations for all subjects ($C_{max}$ in Table 15 above) was greater after TOBI 300 mg delivered by the PARI LC PLUS system (mean ±SD=0.677±0.279 µg/mL) than after TOBI 60 mg delivered by the Aerodose system (0.482±0.201 µg/mL). This mean difference in log $C_{max}$ was statistically significant (p=0.0018), and there was no evidence to suggest the presence of a carryover effect in $C_{max}$ (p=0.6400). The Aerodose inhaler was more efficient than the PARI LC PLUS nebulizer based on $C_{max}$ results adjusted for TOBI dose administered (TOBI 300 mg with PARI LC PLUS=0.002±0.001 (µg/mL)/mg; TOBI 60 mg with Aerodose=0.008±0.003 (µg/mL)/mg).

The time to maximum tobramycin concentrations ($T_{max}$) was virtually identical for the two delivery systems (mean=2.213 hours for PARI LC PLUS and 2.207 hours for Aerodose systems in Table 15 above). $T_{max}$ results in the present study were consistent with observations in a previous study[15] that peak serum tobramycin concentrations occurred at 1 to 2 hours after inhalation.

The mean elimination half-life ($T_{1/2}$) was 4.269 hours for the PARI LC PLUS system and 6.071 hours for the Aerodose system (Table 7).

The mean area under the serum concentration-time curve through 8 hours postdose ($AUC_{(0-8)}$) was significantly greater (p=0.0002 on log $AUC_{(0-8)}$) after TOBI 300 mg delivered by the PARI LC PLUS system (3.622±1.319 µg/mL·hr) than after TOBI 60 mg delivered by the Aerodose system (2.553±0.989 µg/mL·hr). There was no evidence (p=0.7858) to suggest the presence of carryover effect in $AUC_{(0-8)}$. The greater efficiency of the Aerodose inhaler was also seen in dose-normalized $AUC_{(0-8)}$ results (TOBI 300 mg with PARI LC PLUS=0.012±0.004 [µg/mL·hr]/mg; TOBI 60 mg with Aerodose=0.043±0.16 [µg/mL·hr]/mg).

The mean area under the serum concentration by time curve extrapolated to infinity ($AUC_{(0-\infty)}$ in Table 7 above) was not significantly different (p=0.5477 on log $AUC_{(0-\infty)}$) after administration of TOBI 300 mg using the PARI system (5.273±1.699 µg/mL·hr) than after administration of TOBI 60 mg using the Aerodose system (4.630±0.967 µg/mL·hr). No carryover effect was detected (p=0.6006). The greater efficiency of the Aerodose inhaler was similarly seen in dose-normalized $AUC_{(0-\infty)}$ results (TOBI 300 mg with PARI LC PLUS=0.018±0.006 [µg/mL·hr]/mg; TOBI 60 mg with Aerodose=0.077±0.16 [µg/mL·hr]/mg).

Unplanned, exploratory analyses suggested that female subjects achieved slightly higher $C_{max}$, $AUC_{(0-8)}$ and $AUC_{(0-\infty)}$ results than male subjects after both TOBI 300 mg and TOBI 60 mg treatments.

Extent of Exposure

The duration of exposure to study drug and the dose of study drug were not varied in this study. All 10 subjects received a single 300 mg (5 mL) TOBI dose using the PARI LC PLUS jet nebulizer with the DeVilbiss PulmoAide compressor delivery system (control treatment) on one occasion and a single 60 mg (1 mL) TOBI dose using the Aerodose inhaler (experimental treatment) on a second occasion. Each dose was radiolabeled with up to 10 MBq $^{99m}$Tc-DTPA and administered in a randomized two-way crossover fashion separated by a 44-hour minimum washout period.

The mean whole lung deposition using the PARI LC PLUS nebulizer was 8.2% (24.5 mg) of the 300 mg TOBI dose. The mean whole lung deposition using the Aerodose inhaler was 34.8% (20.9 mg) of the 60 mg TOBI dose. A mean of 14.4% (43.3 mg) and 31.5% (18.9 mg) of the corresponding doses were deposited in the oropharynx using the PARI LC PLUS and Aerodose inhalers, respectively. Both inhaler systems were configured such that each subject's exhaled material was collected and did not escape with radioactive aerosol into the surrounding atmosphere. The PARI LC PLUS nebulizer also included a system to collect any radiolabeled droplets escaping from the nebulizer.

Bronchospasm

In this study, decreases in the relative $FEV_1\%$ predicted $\geq 10\%$ (not clinically significant if <20%) and $\geq 20\%$ (clinically significant) from predose measurements to 30-minutes postdose measurements with each delivery system were used as indicators of bronchospasm (airway reactivity). Reductions in $FEV_1\%$ predicted $\geq 20\%$ were considered clinically significant for the purposes of the study. No subject had a drop in $FEV_1\%$ predicted $\geq 10\%$ from predose to postdose regardless of delivery system during this study.

Discussion and Overall Conclusions

The study of this example demonstrates that the AeroDose™ inhaler was more efficient in delivery of aerosolized tobramycin to the lungs of healthy adult volunteers than the approved PARI LC PLUS jet nebulizer with DeVilbiss PulmoAide compressor. Since the Aerodose inhaler is breath-actuated and generates aerosol only during inhalation, proportionally more of the Aerodose dose should be delivered to the lungs than is delivered by the PARI LC PLUS, and there should be minimal wastage of drug by aerosolization during exhalation or by incomplete aerosolization of the contents of the drug reservoir.

During the study, the Aerodose inhaler delivered a significantly greater percentage of the dose to the lungs than the PARI LC PLUS nebulizer (mean 34.8% vs. 8.2%: p=0.005). The actual amount of the dose deposited in the lungs was slightly but not significantly less using the Aerodose inhaler than using the PARI LC PLUS nebulizer (20.9 mg vs. 24.5 mg: p=0.202). These data demonstrate that the Aerodose inhaler delivered nearly as much tobramycin to the lungs as the PARI LC PLUS nebulizer despite nebulizing one-fifth the amount of tobramycin.

Approximately 32% of the Aerodose dose was wasted on the inhaler and exhalation filter combined. By contrast, more than 74% of the PARI LC PLUS dose was wasted by deposition on the inhaler and exhalation filter.

When the Aerodose inhaler was used, 15.2% (9.1 mg) of the 60 mg TOBI dose remained deposited on the inhaler, and 16.9% (10.1 mg) was deposited on the exhalation filter. Since no aerosolization occurred during exhalation when the Aerodose was used, the observed deposition could have been due only to seepage through the mouth-inhaler seal or to residual radiolabeled tobramycin inhaled but immediately exhaled and not deposited in either the lungs or the oropharynx (including esophagus and stomach). Four subjects were noted to have either experienced problems maintaining a seal around the mouthpiece of the Aerodose inhaler or reported that the inhaler failed to nebulize one of the two aliquots of the dose solution. These subjects had approximately 47%, 19%, 53%, and 26%, respectively, of the 60 mg dose deposited on the inhaler and exhalation filter combined. The highest two of these figures were above the range noted for the rest of the subjects (ranging from 17% to 40% deposited on inhaler and exhalation filter combined). Problems with incomplete nebulization or wide variation in subject inhalation effectiveness may have contributed to the amount of wastage of drug during Aerodose usage in the present study.

By comparison, when the PARI LC PLUS jet nebulizer was used, 42.6% (127.8 mg) of the 300 mg TOBI dose remained deposited on the inhaler, and 31.6% (94.8 mg) was deposited on the exhalation filter. Presumably, most or all of the exhalation filter deposition was due to continued aerosolization and consequent loss of drug while subjects exhaled.

Thus, both the Aerodose inhalers and PARI LC PLUS nebulizers wasted drug product in the present study by reason of retention of radiolabeled drug on or in the inhaler or deposition of drug on the exhalation filter (an average of approximately 19 of 60 mg wasted when the Aerodose inhaler was used and approximately 223 of 300 mg wasted when the PARI LC PLUS nebulizer was used). The proportion of the total dose wasted using the Aerodose inhaler was less than half of that wasted using the approved PARI LC PLUS nebulizer.

The Aerodose inhaler also appeared to exhibit better "targeting" or delivery of the dose to the lungs, the target site of the usual *P. aeruginosa* infection in cystic fibrosis patients, than the PARI LC PLUS nebulizer. The Aerodose inhaler deposited slightly more tobramycin in the lungs than in the oropharynx, esophagus, and stomach (lungs 34.8% vs. 31.5% of the 60 mg dose). By comparison, the PARI LC PLUS nebulizer deposited proportionally less of the dose in the lungs than in oropharynx, esophagus, and stomach (lungs 8.2% vs. 14.4% of the 300 mg dose). The ratio of lung to oropharyngeal, esophagus, and stomach combined was approximately 1.1 for the Aerodose inhaler and 0.6 for the PARI LC PLUS nebulizer.

In addition to greater efficiency by greater delivery of drug to the lungs and proportionally greater targeting of the lungs, the Aerodose inhaler was also anticipated to be more efficient by reason of proportionally greater delivery of tobramycin to peripheral rather than central lung regions. The Aerodose particle MMD is smaller (mean MMD=4.0 μm) than that produced by the PARI LC PLUS nebulizer (mean MMD=4.8 μm), so the expectation was that the Aerodose inhaler would deposit a greater proportion of aerosol generated during inhalation in the peripheral airways than the PARI LC PLUS. During the study, the Aerodose inhaler deposited 13.2% (7.9 mg) of the 60 mg dose in the peripheral airways, while the PARI LC PLUS nebulizer deposited 3.1% (9.3 mg) in peripheral airways. Although the Aerodose inhaler achieved proportionally greater peripheral deposition than the PARI LC PLUS nebulizer, both inhalers fell short of amounts predicted for peripheral deposition based on theoretical considerations (Aerodose estimated to peripherally deposit 60% (36 mg) of the 60 mg dose=1.0 mL fill volume·0.95 aerosolization·0.62 respirable particles; PARI LC PLUS estimated to peripherally deposit 16% (48 mg) of the 300 mg dose=5.0 mL fill volume·0.64 aerosolization·0.44 respirable particles).

Results of the study also showed that the Aerodose inhaler required significantly less nebulization time than the PARI LC PLUS nebulizer (mean 20.4 vs. 5.7 minutes, respectively). The 5.7 minute average nebulization time for the Aerodose inhaler did not include the amount of time needed to fill the drug reservoir before nebulization of the second aliquot. Based on nebulization time results and other inhaler features including portability, ease of use, and lack of a need for a compressor, it is anticipated that the Aerodose inhaler would improve patient compliance.

Serum tobramycin concentrations, maximum concentrations, and extent of absorption were greater after administration of TOBI 300 mg using the PARI LC PLUS nebulizer than after administration of TOBI 60 mg using the Aerodose inhaler. These results appeared to be consistent with amounts of tobramycin deposited in lungs and oropharynx (including esophagus and stomach) combined where systemic absorption occurred (mean tobramycin deposited in lungs and oropharynx combined=67.8 mg after TOBI 300 mg; mean=39.8 mg after TOBI 60 mg). Mean serum tobramycin concentrations were higher throughout the 8-hour observation period after administration of TOBI 300 mg using the PARI LC PLUS nebulizer than after administration of TOBI 60 mg using the Aerodose inhaler. Mean $C_{max}$ values were 0.677 and 0.482 µg/mL for TOBI 300 mg and TOBI 60 mg, respectively (statistically significant: p=0.0018). Mean $T_{max}$ results for both inhalers were virtually identical (2.213 and 2.207 hours, respectively). Apparent absorption of tobramycin was significantly greater during the 8-hour postdose period after TOBI 300 mg than after TOBI 60 mg (mean $AUC_{0-8}$=3.622 and 2.553 µg/mL·hr, respectively; statistically significant: p=0.0002), but no treatment differences were noted in $AUC_{0-\infty}$ (TOBI 300 mg and TOBI 60 mg means=5.273 and 4.630 µg/mL·hr, respectively; p=0.5499).

Current results suggested that the 60 mg TOBI dose aerosolized using the Aerodose inhaler produced tobramycin deposition and serum tobramycin concentration results that were significantly or substantially less than results obtained after aerosolization of the approved TOBI 300 mg dose using the PARI LC PLUS nebulizer. Normalized for administered dose, the Aerodose inhaler was substantially more efficient on a per milligram basis in delivery of tobramycin to the systemic circulation than the PARI LC PLUS nebulizer. These results are consistent with the higher deposition (on a milligram basis) in the lung.

Results of the study also showed that single doses of TOBI 300 mg delivered using the PARI LC PLUS jet nebulizer and of TOBI 60 mg delivered using the Aerodose breath actuated nebulizer were safe and well-tolerated by healthy adult male and female volunteers. No instances of bronchospasm were observed, and no notable quantitative changes in pulmonary function were seen. No notable adverse events (AEs) were reported by subjects, and there were no apparent differences between treatment groups in incidence of any AE. Six treatment emergent AEs were reported by 4 subjects, but all events were mild in intensity. Two instances of headache were considered possibly or definitely related to treatment. No clinically significant laboratory results or changes in results were observed. No adverse vital signs, body weights, physical findings, or electrocardiogram results were observed. No evidence of systemic toxicity, as measured by unusually high serum tobramycin concentrations, was observed.

Example 3

In Vivo Study 2

A comparison was made of the safety, pharmacokinetics, aerosol delivery characteristics, and nebulization time of the conventional dose and inhalation delivery system (5 mL ampoule containing 300 mg tobramycin and 11.25 mg sodium chloride in sterile water for injection (TOBI® tobramycin solution for inhalation, Chiron Corporation, Seattle, Wash.), pH 6.0; administered with a PARI LC PLUS™ jet nebulizer with a DeVilbiss PulmoAide™ compressor set to deliver an output pressure of 20 psi—the "control delivery system") with a dose of 420 mg Tobramycin Solution for Inhalation at 120 mg/mL (excipient 3.5 mL of ¼ normal saline adjusted to a pH of 6.0±0.5; 420 mg in 3.5 mL) delivered by the PARI LC PLUS™ jet nebulizer with a Invacare MOBILAIRE™ compressor set to deliver an output pressure of 35 psi (the "experimental delivery system").

The study was designed as an open label, randomized, single-dose, multicenter, two treatment, active-control, and parallel trial. Each patient was administered a single aerosolized dose of study drug with either the control delivery system or the experimental delivery system. In accordance with the study design, a total of 36 eligible male and female patients 12 years of age or older with a confirmed diagnosis of cystic fibrosis were enrolled with a minimum of 4 patients at each site. A 2:1 randomization ratio was employed for assignment of patients to the treatment groups. In the presence of the investigator or study coordinator, each patient was to self-administer either a single dose of 300 mg TOBI® with the control delivery treatment or a single dose of 420 mg Tobramycin Solution for Inhalation with the experimental delivery treatment as listed below.

Control Treatment:
Aerosolized 300 mg TOBI® was delivered by PARI LC PLUS jet nebulizer/DeVilbiss PulmoAide compressor: Preservative free tobramycin for inhalation 60 mg/mL (excipient 5 mL of ¼ normal saline adjusted to a pH of 6.0±0.5); 300 mg in 5 mL; lot number 03K1C (TOBI® at 60 mg/mL).

Experimental Treatment (420 mg Tobramycin Solution for Inhalation or "TSI"):
Aerosolized 420 mg Tobramycin Solution for Inhalation (TSI) was delivered by PARI LC PLUS jet nebulizer/Invacare MOBILAIRE compressor: Preservative free tobramycin 120 mg/mL (excipient 3.5 mL of ¼ normal saline adjusted to a pH of 6.0±0.5); 420 mg in 3.5 mL.

Both 300 mg TOBI® and 420 mg Tobramycin Solution for Inhalation are sterile, non-pyrogenic, preservative-free antibiotics prepared for aerosolization. Each mL of TOBI® contains 60 mg tobramycin and 2.25 mg sodium chloride in sterile water for injection, pH 6.0±0.5 (control treatment). Each mL of TSI contains 120 mg tobramycin and 2.25 mg sodium chloride in sterile water for injection, pH 6.0±0.5 (experimental treatment). Drug supplies for this study were manufactured by Automated Liquid Packaging (ALP), Woodstock, Ill. All repackaging, labeling, and distribution for clinical use was provided by Packaging Coordinators, Inc. (PCI), Philadelphia, Pa. Study drug and device supplies were shipped from Chiron Corporation, Emeryville, Calif. for each patient upon enrollment in the study.

The duration of study participation for each patient was approximately two weeks including a brief (one day one week before treatment) screening period, one day treatment period, and a follow-up one-week after treatment. Study treatments were evaluated for safety and aerosol delivery characteristics up to eight hours post-dose on the day of the single dose treatment administration. The patient was to return to the clinic for a seven day post-treatment follow-up assessment of safety. There were no planned interim safety analyses.

Criteria for Evaluation:

Safety:
  Incidence of bronchospasm defined as $FEV_1$ decrease of $\geq 10\%$ and $FEV_1$ decrease of $\geq 20\%$ from predose to 30 minutes postdose;
  Relative change and absolute change in airway response ($FEV_1$) after single dose of study drug;
  Laboratory measures of safety (clinical lab tests, spirometry testing);
  Incidence of treatment emergent adverse events.

Aerosol Delivery:
  Pharmacokinetic assessment of sputum and serum tobramycin concentrations;
    Sputum was collected at pre-dose and 15 minutes, 1, 2, 4, and 8 hours after dosing;
    Serum was collected at pre-dose and 10 minutes, 1, 2, 4, 6, and 8 hours after dosing;
  Nebulization time.
  Statistical methods: All patients who received a dose of study treatment were evaluated for safety and aerosol delivery characteristics.

Rate of bronchospasm measured by the percent of patients with ≧10% and ≧20% relative decrease in $FEV_1\%$ from pre-dose to 30 minutes post-dose was summarized and compared between treatments using the Fisher's exact test.

A two sample t-test was used to compare the relative change in $FEV_1\%$ from predose to 30 minutes postdose between experimental and control treatments. Summary statistics for relative and absolute change in $FEV_1$ were tabulated by treatment.

Sputum and serum area under curve ($AUC_{0-8}$) and maximum concentrations ($C_{max}$) were summarized and analyzed for treatment differences using a general linear model analysis of variance (ANOVA). Pharmacokinetic parameters were calculated using a non-compartmental model. Sputum and serum concentrations were summarized and graphically illustrated by treatment.

Laboratory measures of safety and incidence of treatment-emergent adverse events were summarized and descriptively compared between treatments.

Nebulization time was recorded and summarized for each of the two delivery treatments.

Safety Variables

Aerosol delivery variables were tobramycin concentrations in sputum and serum, sputum and serum tobramycin pharmacokinetic parameters, and aerosol nebulization time. Safety variables were the incidence and severity of bronchospasm, measured as the number of patients experiencing a ≧10% and a ≧20% decrease in forced expiratory volume in one second ($FEV_1$) within 30 minutes after dosing (a ≧20% decrease in $FEV_1$ was considered clinically significant), the incidence of treatment emergent adverse events (AEs), clinical laboratory test results, the number of patients with serum tobramycin concentrations ≧4 μg/mL, physical examination findings, and vital signs results.

Primary Aerosol Delivery Variables

Evaluation of the aerosol delivery characteristics of 420 mg Tobramycin Solution for Inhalation at 120 mg/mL delivered by the PARI LC PLUS™/Invacare MOBILAIRE™ delivery system compared to 300 mg TOBI® at 60 mg/mL delivered by the FDA-approved PARI LC PLUS™/DeVilbiss PulmoAide™ delivery system was based on determination of sputum and serum tobramycin concentrations, calculation of certain sputum and serum pharmacokinetic parameters, and measurement of nebulization time.

Sputum Tobramycin Concentrations: Sputum samples were expectorated by patients from a deep cough and collected before day 1 dosing (predose) and at 0.25, 1, 2, 4, and 8 h after the end of the nebulization period. Sputum samples were collected as close as possible to specified times and were considered to have been drawn on time within ±2 minutes for the 15-minute posttreatment collection and within ±10 minutes for the 1-, 2-, 4-, and 8-hour posttreatment collections. Samples collected outside these intervals were considered protocol deviations. A minimum 100 mg sputum (not saliva) sample was collected before the single dose of study treatment to determine the baseline tobramycin concentration. Immediately after dosing, patients rinsed their mouths with 30 mL of normal saline, gargled for 5-10 seconds, and expectorated the rinse. This sequence of post-treatment rinsing was repeated for a total of three rinses. Sputum samples were stored at −70° C. or below until analysis. The concentration of tobramycin was analyzed using reversed-phase high-performance liquid chromatography (HPLC) with ultraviolet detection. Patient sputum samples were first liquefied with 0.2 N NaOH and diluted with Tris buffer (20.0 g Trizma base/L). Sputum standard samples were prepared by spiking diluted pooled sputum from CF patients with tobramycin to final concentrations of 0, 20, 40, 100, 200, 400, and 1000 μg/g of sputum. Assay quality control samples were prepared by spiking diluted pooled sputum to contain 40, 300, and 800 μg/g. The internal standard sisomycin (100 μL, 0.15 mg/mL in Tris buffer) was added to 100 μL of each standard, control, and subject sample, followed by 400 μL of acetonitrile and 50 μL of 2,4-dinitrofluorobenzene (0.17 g/mL). The sample reaction mixtures were heated in a dry-block heater for 1 h at 80° C. After addition of 600 μL of 60/40 acetonitrile/water (v/v), 50 μL was analyzed by HPLC. Samples were injected onto a Waters Nova-Pak® C-18, 3.9×150 mm, 4 μm column connected to a Waters HPLC with 600E pump, 486 or 2487 ultraviolet detector ($\lambda_{max}$=360 nm) and 717 Plus autosampler. The mobile phase consisted of 0.2% acetic acid in acetonitrile (39/61, v/v), pumped at a rate of 1.5 mL/min for 5 min, 2.0 mL/min for an additional 9 or 10 min, depending on the length of the run. Waters Millennium-32 C/S LC Software (version 3.20) was used to operate the Waters HPLC instruments as well as acquire raw data, process, compute, and report the analytical results. The ratio of the peak height of tobramycin to the internal standard sisomycin (PHR) was calculated. The assay was completed in 8 runs. Retention time ranges of 4.2 to 4.4 min, and 10.8 to 11.8 min were observed for tobramycin and sisomycin, respectively. A linear relationship existed between PHR and concentration from 20 to 1000 μg/g for sputum. The regression model was PHR=Bx+A (x=tobramycin concentration), weighted 1/x. The lower limit of quantitation was 20 μg/g. The concentrations of the standard samples were within 97 to 105% of the nominal concentration, with coefficients of variation not higher than 3.4%. The precision of the assay, as reflected by the CV of the quality control samples, was 2.3%, 2.2% and 2.6%, for the 40, 300, and 800 μg/g samples, respectively. The accuracy of the method, reflected by the interassay recoveries of the quality control samples, was 103%, 99%, and 98% for the 40, 300, and 800 μg/g quality control samples, respectively. Overall, this method exhibited suitable accuracy and precision for pharmacokinetic analysis.

Serum Tobramycin Concentrations: Blood samples were collected at predose and at 0.167, 1, 2, 4, 6, and 8 h after the end of the nebulization period. Samples were collected as close as possible to specified times and were considered to have been drawn on time within ±2 minutes for the 10-minute posttreatment collection and within ±10 minutes for the 1-, 2-, 4-, 6-, and 8-hour posttreatment collections. Samples collected outside these intervals were considered protocol deviations. Serum was harvested and stored at −70° C. or below until analysis. Concentrations of tobramycin in serum were analyzed with a modified fluorescence polarization immunoassay (FPIA) method using the Abbott TDx®/TDxFLx® System. Samples were added directly to the dilution well of the sample cartridge. The net polarization was acquired by the TDx®/TDxFLx® apparatus and manually entered into an Oracle database. A weighted four parameter logistic equation was used to calculate the concentrations of tobramycin. The concentrations of tobramycin were reported in terms of free base equivalents. For assaying the subject samples of the study, calibration standards (0.050, 0.100, 0.200, 0.400, 0.600, 0.800, 1.000 μg/mL) and quality control samples (0.150, 0.400, and 0.750 μg/mL) were prepared in house. The assay was completed in 8 runs. A linear relationship existed between polarization response and concentration from 0.050 μg/mL to 1.00 μg/mL. The lower limit of quantitation was 0.050 μg/mL. The precision of the assay, as reflected by the CV of the quality control samples, was 3.3%, 4.9%, and 4.9% for the 0.150, 0.400, and 0.750 μg/mL samples, respectively.

The accuracy of the method, reflected by the mean interassay recoveries of the quality control samples, was 101%, 103%, and 104% for the 0.150, 0.400, and 0.750 pg/mL samples, respectively. Overall, this method exhibited suitable accuracy and precision for pharmacokinetic analysis.

Nebulization Time:

Nebulization time was defined as the length of time from the start of the patient's first tidal breath to completion of aerosol administration. Aerosol administration was complete when the nebulizer began to sputter. If aerosol administration was interrupted for any reason, the time of interruption and start and stop times of continued aerosol administration were recorded. If dosing was interrupted, nebulization time was considered to be not calculable.

Residual Tobramycin in the Nebulizer: The amount of residual tobramycin solution remaining in the nebulizer after completion of aerosol administration was determined by recording pretreatment and posttreatment weight of the nebulizer system including nebulizer, filter valve, and study drug. The research coordinator collected residual study drug remaining in the nebulizer after aerosol administration into a vial labeled with patient information. The vial was returned for measurement of the amount of drug output from the nebulizer and for determination of the extent of the concentration of study drug left in the nebulizer.

Safety Variables

Bronchospasm: The study protocol prospectively identified bronchospasm as an adverse airway response to inhalation of aerosolized antibiotic of particular relevance to patients with cystic fibrosis. In order to determine whether current study treatments produced bronchospasm, patients performed spirometry (pulmonary function) tests to measure $FEV_1$ before and 30 minutes following completion of study treatment administration according to the method described in the protocol. Airway response to the study drug was assessed by evaluating the relative percent change in $FEV_1$ from predose to 30 minutes after the end of treatment using the following formula.

$$\text{relative } FEV_1 \text{ \% change} = \frac{30 \text{ min postdose } FEV_1 - \text{predose } FEV_1}{\text{predose } FEV_1} \times 100\%$$

Bronchospasm was defined as a decrease in $FEV_1$ of $\geq 10\%$ at 30 minutes after dosing, relative to the predose result. A decrease in $FEV_1$ of $\geq 20\%$ was considered to represent clinically significant bronchospasm. Moreover, if there was a posttreatment decrease in $FEV_1$ of $\geq 30\%$, spirometry was to be repeated until the $FEV_1$ decrease was <10% below the predose result. An $FEV_1$ % decrease $\geq 30\%$, and all symptoms associated with the change in pulmonary function, were to be recorded as adverse events. The protocol defined the severity of decrease in $FEV_1$ based in part on the National Cancer Institute (NCI) Common Toxicity Criteria Adverse Events Grading Scale. However, slight inconsistencies in the protocol definitions of bronchospasm and of the severity of $FEV_1$ changes were noted during preparation of the analyses and report. To resolve the differences, the actual system used during the analysis to classify the severity of $FEV_1$ changes relative to the predose result is listed below.

TABLE 16

AIRWAY RESPONSE ($FEV_1$) (BRONCHOSPASM) $FEV_1$ % DECREASE BELOW PREDOSE VALUE

| Severity | Protocol Classification | Analysis Classification |
|---|---|---|
| Mild: | $\geq 10\%$-$\leq 20\%$ | $\geq 10\%$-$<20\%$ |
| Moderate: | $>20\%$-$\leq 30\%$ | $\geq 20\%$-$<30\%$ |
| Severe: | $>30\%$ | $\geq 30\%$ |

Clinical Laboratory Tests

At screening, laboratory tests were performed to measure serum creatinine, blood urea nitrogen (BUN), urine protein (proteinuria by dipstick), and to detect pregnancy in females of childbearing potential. If abnormal at screening, serum creatinine, BUN, and urine protein tests were to be repeated before the time of dosing. Final test results were obtained based on specimens drawn at the follow-up visit on day 8 of the study.

After the mean body weight difference between treatment groups became known by Chiron personnel, estimated creatinine clearance was calculated for patients using the Cockroft-Gault equation below to evaluate renal clearance characteristics of the two groups and to clarify the pharmacokinetic results of the study.

Male Patients:
estimated creatinine
clearance (mL/min)=(140-age[yr])(body weight[kg])/72*(serum creatinine [mg/dL])

Female Patients:
estimated creatinine
clearance (mL/min)=0.85*((140-age[yr])(body weight[kg])/72*(serum creatinine [mg/dL])

All abnormal laboratory test results, whether present on entry into the study or arising during the study, were evaluated by the study investigator for clinical significance and relationship to study drug. If the abnormal result was considered unrelated to study drug, the investigator was to identify the probable cause of the result. Laboratory results considered markedly abnormal and clinically significant were BUN >16 mmole/l (>45 mg/dl), serum creatinine >177 μmole/l (>2 mg/dl), and proteinurea $\geq 3^+$.

Other Safety Variables

Serum assay results were screened for tobramycin concentrations $\geq 4$ μg/mL from specimens collected from 10 minutes through 8 hours after completion of study treatments. In parallel, patient records and CRFs were examined for evidence of systemic toxicity potentially related to elevated tobramycin levels. Assay results were not available until after patients' discharge from the study, so screening for unusually high serum tobramycin concentrations and evidence of systemic toxicity was undertaken when all pertinent results were received.

Pharmacokinetics

Pharmacokinetic parameters for both sputum and serum tobramycin were derived to characterize aerosol delivery capabilities of control and experimental treatments. The concentration (C) versus time (t) data (Listings 16.2.5.2 and 16.2.5.3) were analyzed by model-independent methods to obtain the pharmacokinetic parameters. The areas under the plasma concentration-time curve from time zero (predose) to infinity (AUC) and under the first moment of the plasma concentration-time curve (AUMC) were obtained by the trapezoidal rule, extrapolated to infinity. The terminal rate constant ($\lambda_z$) was determined by log-linear regression of the terminal phase. The maximum concentration ($C_{max}$) and the time to maximum after the end of the nebulization period ($t_{max}$) were obtained by inspection. In addition, the following parameters were calculated:

$$t_{1/2} = \ln(2)/\lambda_z$$

$$CL/F = D/AUC$$

$$V_z/F = CL_{po}/\lambda_z$$

where $t_{1/2}$ is the terminal half-life, CL/F is the total body clearance, and $V_z/F$ is the terminal volume of distribution. Since the absolute bioavailability of tobramycin (F) in the two formulations used in this study is not known, the calculated clearance and volume of distribution are hybrid parameters that do not account for differences in bioavailability between the two formulations. All parameters were calculated for serum; only AUC, $C_{max}$, $t_{max}$, $\lambda_z$, and $t_{1/2}$ were calculated for sputum.

Concentrations below the lower limit of quantitation were treated as zero for all calculations. Since there was an insufficient volume of matrix to assay tobramycin in the following time points, they were excluded from the pharmacokinetic analysis:

TABLE 17

EXCLUSIONS FROM PHARMACOKINETIC ANALYSIS

| Matrix | Subject | Time |
|---|---|---|
| Serum | 01-110 | 6 |
| | 02-116 | 1 |
| | 03-102 | 0.167, 1, 2 |
| | 03-105 | 0, 0.167, 1, 2, 4, 6, 8 |
| | 03-131 | 0.167 |
| | 05-125 | 4, 8 |
| | 06-120 | 2 |
| Sputum | 08-127 | 2 |

Data Handling

Case report form data were entered in duplicate into a Clintrial™ database by the department of Biostatistics and Clinical Data Management (BCDM) at Chiron Corporation. Data quality assurance was performed using PL/SQL and SAS™ 6.12 or higher software (SAS Institute, Cary, N.C.). Analysis was performed by Chiron Corporation, using SAS version 6.12 or higher software, based on a predefined analysis plan developed by Chiron Corporation. The estimated overall database error rate was 0.xx % with an upper 95% confidence limit of 0.xx %. This upper confidence limit is below the departmental standard of 0.5%.

Statistical Methods and Determination of Sample Size

Statistical and Analytical Plans: Serum and sputum pharmacokinetic parameters, the incidence of bronchospasm, and the relative change from predose in 30-minute postdose $FEV_1\%$ predicted were analyzed statistically to assess the significance of any apparent differences between test and reference treatments. All statistical tests described in following sections were two-tailed tests of significance, and the criterion for statistical significance was set at $\alpha=0.05$ unless otherwise noted.

Primary Aerosol Delivery Analyses:

All patients who received the single dose of test or reference treatment were included in the analysis and evaluation of aerosol delivery characteristics. Aerosol delivery was characterized on the basis of serum and sputum tobramycin concentrations, derived serum and sputum pharmacokinetic parameters, and nebulization time. The effect of treatment (300 mg TOBI vs 420 mg TSI), gender, and age group (less than 18, 18 years or older) on the AUC, $C_{max}$, $\lambda_z$, CL/F, and $V_z/F$ of tobramycin in serum, and on the AUC, $C_{max}$, and $\lambda_z$ of tobramycin in sputum, was analyzed by a three-way analysis of variance. Furthermore, the relationship between body weight and AUC, $C_{max}$, CL/F, and $V_z/F$ of tobramycin in serum, and between body weight and AUC and $C_{max}$ of tobramycin in sputum were analyzed by regression analysis. All tests employed a significance level $\alpha=0.05$. All parameters are expressed as the mean ±SD. A harmonic half-life was estimated as:

$$\overline{t_{1/2}} = \ln(2)/\overline{\lambda_z}$$

in which $\overline{\lambda_z}$ is the arithmetic mean of the terminal rate constants at each dose. The standard deviation of the harmonic half-life, $SD(\overline{t_{1/2}})$, was obtained as:

$$SD(\overline{t_{1/2}}) = \frac{\ln(2)}{\overline{\lambda_z}} \times \frac{SD(\overline{\lambda_z})}{\overline{\lambda_z}}$$

where $SD(\overline{\lambda_z})$ is the standard error of the mean terminal rate constant at each dose.

Safety Analyses

Analysis of Airway Response:

The primary safety variable was the rate of bronchospasm, defined as a $\geq 10\%$ decrease in $FEV_1$ from predose to 30 minutes after treatment on day 1 of the study. Secondary safety variables were (a) the rate of clinically significant bronchospasm, defined as a $\geq 20\%$ decrease in $FEV_1$ from predose to 30 minutes after treatment on day 1, and (b) the relative change in $FEV_1$ from predose to 30 minutes after treatment on day 1. The rates of occurrence of all instances of bronchospasm ($FEV_1\%$ decrease $\geq 10\%$) and of all instances of clinically significant bronchospasm ($FEV_1\%$ decrease $\geq 20\%$) were analyzed to assess the statistical significance of test vs. reference treatment differences using the Fisher's Exact test. The protocol specified that the treatment difference in the incidence of bronchospasm would be tested for statistical significance using the Cochran-Mantel-Haenszel test. Due to the low incidence of bronchospasm in the enrolled patients, the Fisher's exact test was used for this analysis since it makes no assumptions regarding the minimum expected cell frequencies. The test vs. reference treatment difference in mean relative change from predose in 30-minute postdose $FEV_1\%$ predicted was tested for statistical significance using the two-sample t-test.

Adverse Events: The total incidence of individual treatment emergent adverse events (percent of patients who experienced the event at least once during or after study treatment) was evaluated descriptively for any noteworthy differences between test and reference treatments. AEs were also summarized by severity (mild, moderate, severe) and drug relationship (unrelated, possibly related) for test and reference treatments.

Disposition of Subjects

A total of 40 patients were screened for the study by the eight investigators. Thirty-eight of the 40 screened patients met entrance criteria, were enrolled in the study (Table 18), and were randomized to one of the two treatments. Enrollment and randomization of the 38 patients at the eight sites was as summarized in Table 18 below:

TABLE 18

ENROLLMENT AND RANDOMIZATION BY SITE AND TREATMENT

| Site | 300 mg TOBI ®<br>PARI LC PLUS ™/DeVilbiss<br>PulmoAide ™ Delivery System<br>(no. patients<br>enrolled and randomized) | 420 mg TSI<br>PARI LC PLUS ™/Invacare<br>MOBILAIRE ™ Delivery System<br>(no. patients<br>enrolled and randomized) |
|---|---|---|
| 01 | 2 | 2 |
| 02 | 1 | 3 |
| 03 | 2 | 6 |
| 04 | 0 | 2 |
| 05 | 2 | 4 |
| 06 | 2 | 3 |
| 07 | 2 | 2 |
| 08 | 3 | 2 |
| Total enrolled and randomized | 14 | 24 |

Two of the 40 screened patients failed to meet entrance criteria and were not enrolled in the study: one patient did not meet the protocol inclusion criterion requiring patients to have screening $FEV_1$% predicted results that were $\geq 25$%; and one patient did not meet the exclusion criterion requiring patients to have not taken inhaled or intravenous aminoglycosides within seven days before study treatment administration. Thirty-eight patients met all study entry criteria and were randomized to treatments. Thirty-seven of the 38 randomized patients received one dose of study treatment (Table 18). One patient was enrolled and randomized but was withdrawn from the study before dosing due to staff inability to establish venous access for predose day 1 (visit 2) blood draws. The 37 randomized and dosed patients constituted the intent to treat (ITT) population. All 37 patients who received study treatments completed the study.

Aerosol Delivery Evaluation

Data Sets Analyzed

All 37 patients in the ITT population (i.e., those who were randomized and received a dose of study treatment) were evaluable for the aerosol delivery objective of the protocol. Twenty four patients received a dose of 420 mg TSI using the PARI LC PLUS™/Invacare MOBILAIRE™ Delivery System, and 13 patients received a dose of 300 mg TOBI® using the PARI LC PLUS™/DeVilbiss PulmoAide™ Delivery System. Patient 08/137 was excluded from all aerosol delivery evaluations due to withdrawal from the study before dosing.

Demographic and Other Baseline Characteristics

Demographic Characteristics:

Nineteen male and 18 female patients, 12 to 44 years of age and diagnosed with cystic fibrosis, constituted the ITT population. Thirty-one patients were Caucasian, four patients were Hispanic, and two patients were black. Gender and race distributions were similar between the 420 mg TSI and 300 mg TOBI® treatment groups. On the average, ITT patients in the 300 mg TOBI® group were approximately 2.7 years older, 4.9 centimeters taller, and 10.7 kilograms heavier at screening (visit 1) than ITT patients in the 420 mg TSI group. A similar treatment difference in mean body weight was apparent before day 1 (visit 2) dosing, and no noteworthy change in mean weight was noted between screening and day 1.

Analysis of Aerosol Delivery

Primary Aerosol Delivery Analysis: Examination of the mean plasma concentration-time plot for both formulations in serum (FIG. 10) indicates that tobramycin is rapidly absorbed: all subjects achieved maximum concentrations in the time span of 10 min to 4 h. An elimination phase was also observed in the concentration-time profiles, with individual estimates of half-life ranging from 1.1 to 6.8 h. In sputum (FIG. 11), maximum concentrations were achieved between 15 min and 2 h, and individual estimates of half-life ranged from 0.48 to 9.47 h. These estimates are consistent with previous studies.

Serum and sputum pharmacokinetic parameters are summarized in Tables 19 and 20 as follows.

TABLE 19

SERUM PHARMACOKINETIC PARAMETERS (MEAN ± SD) OF TOBRAMYCIN AFTER ADMINISTRATION OF 300 MG TOBI AND 420 MG TSI

| Parameter | 300 mg TOBI | 420 mg TSI |
|---|---|---|
| AUC (μg h/mL) | 4.38 ± 1.97 | 4.41 ± 1.69 |
| $C_{max}$ (μg/mL) | 0.861 ± 0.344 | 0.906 ± 0.542 |
| Median $t_{max}$ (h) | 1 (1-4)* | 1 (0.17-2) |
| $\lambda_z$ (h$^{-1}$) | 0.250 ± 0.052 | 0.243 ± 0.098 |
| $t_{1/2}$ (h) | 2.78 ± 0.58 | 2.86 ± 1.15 |
| CL/F (L/h) | 88 ± 62 | 114 ± 59 |
| $V_z$/F (L) | 379 ± 325 | 511 ± 278 |

TABLE 20

SPUTUM PHARMACOKINETIC PARAMETERS (MEAN ± SD) OF TOBRAMYCIN AFTER ADMINISTRATION OF 300 MG TOBI AND 420 MG TSI

| Parameter | 300 mg TOBI | 420 mg TSI |
|---|---|---|
| AUC (μg h/g) | 1521 ± 845 | 1176 ± 686 |
| $C_{max}$ (μg/g) | 930 ± 795 | 935 ± 1040 |
| Median $t_{max}$ (h) | 0.25 (0.25-2)* | 0.25 (0.25-0.25) |
| $\lambda_z$ (h$^{-1}$) | 0.59 ± 0.31 | 0.52 ± 0.37 |
| $T_{1/2}$ (h) | 1.17 ± 0.98 | 1.33 ± 0.95 |

Figure 10:
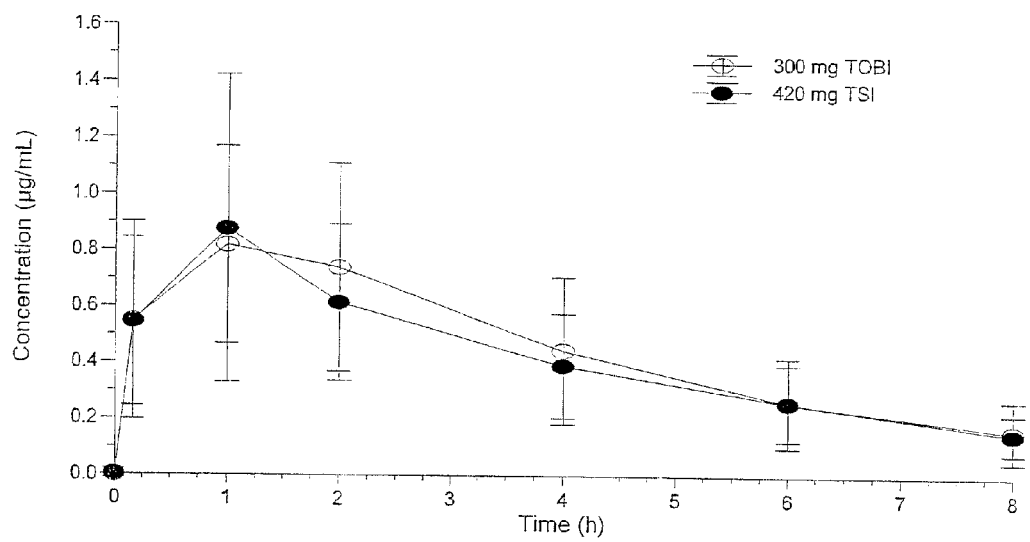
FIG. 10 is a graphical representation showing the average serum-time profiles of tobramycin after administration of 300 mg tobramycin (TOBI) and 420 mg tobramycin solution for inhalation (TSI), as described in Example 3.
Figure 11:
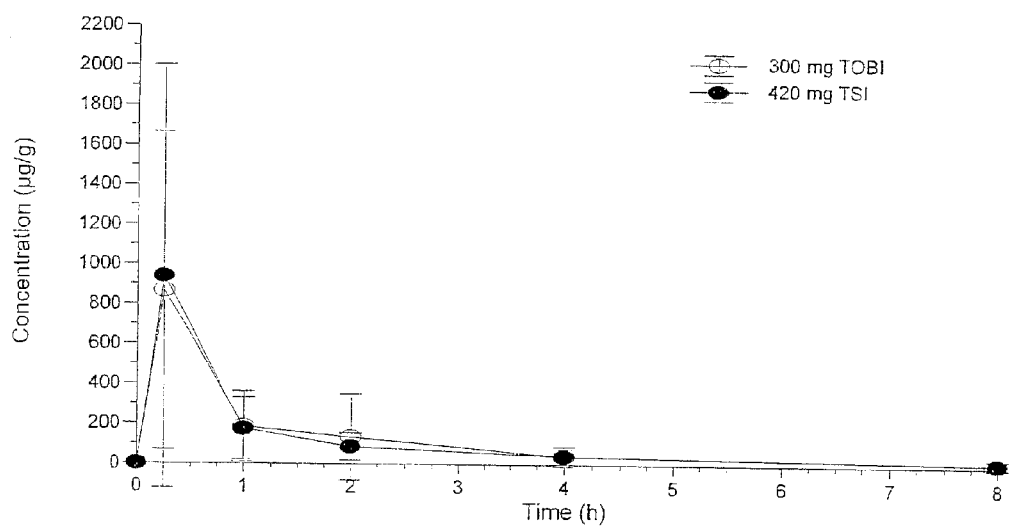
FIG. 11 is a graphical representation showing the average sputum-time profiles of tobramycin after administration of 300 mg tobramycin (TOBI) and 420 mg tobramycin solution for inhalation (TSI), as described in Example 3.

The serum and sputum concentration-time curves for both treatments were virtually superimposable (FIGS. 10 and 11; Tables 19 and 20). Serum parameters ($C_{max}$, $t_{max}$, AUC, CL/F, $V_z$/F) showed no statistically significant differences between the treatment groups (Table 19). Sputum parameters (AUC, $C_{max}$, and $\lambda_z$) also showed no statistically significant treatment differences (Table 20). Neither age nor body weight had a statistically significant effect on these pharmacokinetic parameters. In addition, there were no statistically significant correlations between serum and sputum AUC, and between serum and sputum $C_{max}$. The variability of the pharmacokinetic parameters in serum and in sputum was similar to previous trials. In summary, these findings indicate that it is possible to achieve comparable serum and sputum levels of tobramycin to the 300 mg TOBI® formulation by using the 420 mg TSI formulation.

Secondary Aerosol Delivery Analyses

Nebulization Time: Nebulization time was substantially reduced during administration of the test 420 mg TSI formulation below that observed during administration of the marketed 300 mg TOBI® formulation. Mean ±SD total nebulization time was 9.7±3.0 minutes during 420 mg TSI administration compared to 18.1±3.6 minutes during 300 mg TOBI® administration (Table 21). These findings indicate that the reduced nebulization times used in the 420 mg TSI treatment did not change the pharmacokinetics of tobramycin relative to the marketed 300 mg TOBI® formulation.

TABLE 21

MEAN (SD) NEBULIZATION TIME

| Parameter [mean (SD)] | 300 mg TOBI PARI LC PLUS[a] PulmoAide Compressor (n = 13) | 420 mg TSI PARI LC PLUS[b] MOBILAIRE Compressor (n = 24) |
|---|---|---|
| Nebulization Time (min) | 18.1 (3.6) | 9.7 (3.0) |
| No. pts with data | 12 | 23 |

Source: Table 14.2.2.1.
Notes:
[a]Reference treatment = TOBI 300 mg delivered by PARI LC PLUS nebulizer with PulmoAide compressor. Nebulization time for patient 07/132 indeterminate due to interruption in dosing and unrecorded stop/start times.
[b]Test treatment = TSI 420 mg delivered by PARI LC PLUS nebulizer with MOBILAIRE compressor. Nebulization time for patient 07/126 indeterminate due to interruption in dosing and unrecorded stop/start times.

Nebulizer Weight: Nebulizer weight changes from before to after dosing indicated that the test 420 mg TSI formulation delivered less product to patients than the marketed 300 mg TOBI® formulation. Mean ±SD amounts of product delivered to patients was 1.86±0.53 gm during 420 mg TSI administration and 2.74±1.64 gm during 300 mg TOBI® administration (Table 14.2.2.2), as summarized in Table 11.4-4 below. These findings likely reflect the smaller 3.5 mL volume of TSI formulation in the nebulizer compared to the 5 mL volume of the TOBI® formulation.

TABLE 22

MEAN (SD) NEBULIZER WEIGHT AND CHANGE IN WEIGHT

| Parameter [mean (SD)] | 300 mg TOBI[a] PARI LC PLUS PulmoAide Compressor (n = 13) | 420 mg TSI[b] PARI LC PLUS MOBILAIRE Compressor (n = 24) |
|---|---|---|
| Nebulizer Weight (gm) | | |
| Predose | 68.25 (7.30) | 69.17 (0.61) |
| No. patients with data | 13 | 24 |
| Postdose | 65.51 (6.89) | 67.30 (0.80) |
| No. patients with data | 13 | 23 |

TABLE 22-continued

MEAN (SD) NEBULIZER WEIGHT AND CHANGE IN WEIGHT

| Parameter [mean (SD)] | 300 mg TOBI[a] PARI LC PLUS PulmoAide Compressor (n = 13) | 420 mg TSI[b] PARI LC PLUS MOBILAIRE Compressor (n = 24) |
|---|---|---|
| Change in weight | -2.74 (1.64)[c] | -1.86 (0.53) |
| No. patients with data | 13 | 23 |

Notes:
[a]Reference treatment = TOBI 300 mg delivered by PARI LC PLUS nebulizer with PulmoAide compressor.
[b]Test treatment = TSI 420 mg delivered by PARI LC PLUS nebulizer with MOBILAIRE compressor. Nebulizer weight for patient 02/116 not recorded after dosing.
[c]The posttreatment nebulizer weight for patient 07/132 included the weight of the filter, and the pretreatment to posttreatment change in nebulizer weight was an increase by 2.20 gm. Excluding this erroneous value yields a mean (SD) change of -3.16 ( ) gm.

Discussion

Aerosol delivery findings indicate that it is possible to achieve comparable serum and sputum levels of tobramycin to the 300 mg TOBI® formulation by using the 420 mg TSI formulation. Present findings also indicate that the reduced nebulization times and reduced amount of product delivered to patients during administration of the 420 mg TSI treatment did not change the pharmacokinetics of tobramycin relative to the marketed 300 mg TOBI® formulation.

Mean serum tobramycin concentration-time plots for both formulations indicate that tobramycin is rapidly absorbed: all subjects achieved maximum concentrations in the time span of 10 min to 4 h. An elimination phase was also observed in the concentration-time profiles, with individual estimates of half-life ranging from 1.1 to 6.8 h. In sputum, maximum concentrations were achieved between 15 min and 2 h, and individual estimates of half-life ranged from 0.48 to 9.47 h.

The serum and sputum concentration-time curves for both treatments in the present study were virtually superimposable. Serum parameters ($C_{max}$, $t_{max}$, AUC, CL/F, $V_z/F$) showed no statistically significant differences between the treatment groups. Mean (±SD) serum $C_{max}$ results for both the 420 mg TSI and the 300 mg TOBI® groups (0.906±0.542 μg/mL vs. 0.861±0.344 μg/mL, respectively) were consistent with results from previous studies.[5,40,41] The average serum concentration of tobramycin one hour after inhalation of a single 300 mg dose of TOBI® by CF patients was 0.95 μg/mL.[5] After 20 weeks of therapy on the TOBI® regimen, the average serum tobramycin concentration one hour after dosing was 1.05 μg/mL.

Sputum parameters (AUC, $C_{max}$, and $\lambda_z$) also showed no statistically significant treatment differences in the present study. Mean (±SD) sputum $C_{max}$ results for both the 420 mg TSI and the 300 mg TOBI® groups (935±1040 μg/g vs. 930±795 μg/g, respectively) were consistent with results from previous studies.[5,40,41] Sputum results in the present study were highly variable. By comparison, high variability of tobramycin concentration in sputum was also observed in both Phase 3 trials.[29,30] Ten minutes after inhalation of the first 300 mg dose of TOBI® in the Phase 3 trials, the average concentration of tobramycin in sputum was 1237 μg/g (ranging from 35 to 7414 μg/g). Tobramycin does not accumulate in sputum; after 20 weeks of therapy with the TOBI® regimen, the average concentration of tobramycin at ten minutes after inhalation was 1154 μg/g (ranging from 39 to 8085 μg/g). Two hours after inhalation, sputum concentrations declined to approximately 14% of the tobramycin levels measured at ten minutes after inhalation.

Neither age nor body weight had a statistically significant effect on serum and sputum pharmacokinetic parameters. In addition, there were no statistically significant correlations between serum and sputum AUC and between serum and sputum $C_{max}$.

Nebulization time for the test 420 mg TSI formulation was substantially reduced below that observed during administration of the marketed 300 mg TOBI® formulation (mean ±SD=9.7±3.0 min vs. 18.1±3.6 min, respectively). Nebulization times for the marketed 300 mg TOBI® formulation were consistent with previous studies.[40,41] Therefore, the study achieved a key benchmark with the demonstration that the alternative delivery system, consisting of 3.5 mL of a 120 mg/mL (total 420 mg tobramycin) Tobramycin Solution for Inhalation (TSI) delivered using a PARI LC PLUS™ jet nebulizer driven by an Invacare MOBILAIRE™ compressor, reduced nebulization time below 10 minutes on the average.

Finally, present findings indicate that the reduced nebulization times during administration of the 420 mg TSI treatment did not change the pharmacokinetics of tobramycin relative to the marketed 300 mg TOBI® formulation.

Safety findings indicate that both a single dose of the 420 mg TSI formulation and a single dose of the marketed 300 mg TOBI® formulation were well-tolerated by patients with cystic fibrosis. The incidence of bronchospasm (≧10% relative decrease in $FEV_1$) was approximately 8% for each treatment (two 420 mg TSI and one 300 mg TOBI® patients); a single patient in the 300 mg TOBI® group had clinically significant bronchospasm (≧10% relative decrease in $FEV_1$). The treatment mean relative decrease in $FEV_1$ was −3.36±5.47% for 420 mg TSI and −2.14±9.62% for 300 mg TOBI®.

By comparison, in the Phase III trials of TOBI®, the median change in $FEV_1$ 30 minutes after the first dose of study drug had been administered was −1.8% in the tobramycin group. At Week 20, the median change in $FEV_1$ was −2.0% in the tobramycin group. Because up to 95% of CF patients have bronchodilator-responsive airflow obstruction, and the within-subject variability for pulmonary function tests in CF patients has been documented to be greater than in normal patients, a ≧20% decrease in $FEV_1$ was considered clinically significant.[33] Twelve of 258 TOBI® patients (4.7%) had a ≧20% decrease in $FEV_1$ with TOBI® administration. Only two of these patients documented acute symptoms, and no patients had a ≧20% decrease in $FEV_1$ more than once with TOBI®.

The present study also showed that the incidence of other treatment-related adverse events was very low (2 of 24 TSI patients and 1 of 13 TOBI® patients=8%) and did not differ between treatments. All three patients reported mild to moderate decreased pulmonary function test results, and one of the three patients also reported severe cough. Among all treatment-emergent AEs, events reported most frequently by 420 mg TSI patients were cough (4 patients=17%), crepitations and sore throat (13%), and pyrexia, nasal congestion, rhinorrhoea, and sputum increased (8%). AEs reported most frequently by 300 mg TOBI® patients were cough (3 patients=23%) and sore throat, dyspnoea, and rhinorrhoea (15%). These events were mostly mild to moderate in intensity (two instances of severe cough), were most likely related to patients underlying cystic fibrosis and other medical conditions, and were consistent with previous large Phase 3 study results.[29,30] A single patient experienced serious non-drug-related symptoms (SAEs) indicative of an exacerbation of CF. None of the patients in the study were withdrawn due to AEs, and no other clinically significant findings were noted in physical examinations, vital signs, or other safety measurements that represented an increase in risk to patients by reason of administration of study treatments.

CONCLUSIONS

The findings of the present study indicate that it is possible to achieve comparable serum and sputum levels of tobramycin to the 300 mg TOBI® formulation by using 420 mg TSI formulation. Current findings also indicate that the reduced nebulization times used in the 420 mg TSI treatment did not change the pharmacokinetics of tobramycin relative to the marketed 300 mg TOBI® formulation. Mean plasma concentration-time plots for both formulations in serum indicate that tobramycin is rapidly absorbed: all subjects achieved maximum concentrations in the time span of 10 min to 4 h. An elimination phase was also observed in the concentration-time profiles, with individual estimates of half-life ranging from 1.1 to 6.8 h. In sputum, maximum concentrations were achieved between 15 min and 2 h, and individual estimates of half-life ranged from 0.48 to 9.47 h. These estimates are consistent with previous studies.

The serum and sputum concentration-time curves for both treatments were virtually superimposable. Serum parameters ($C_{max}$, $t_{max}$, AUC, CL/F, $V_z/F$) showed no statistically significant differences between the treatment groups. Sputum parameters (AUC, $C_{max}$, and $\lambda_z$) also showed no statistically significant treatment differences. Neither age nor body weight had a statistically significant effect on these pharmacokinetic parameters. In addition, there were no statistically significant correlations between serum and sputum AUC, and between serum and sputum $C_{max}$.

During administration of the test 420 mg TSI formulation, nebulization time was substantially reduced below that observed during administration of the marketed 300 mg TOBI® formulation (mean ±SD=9.7±3.0 min vs. 18.1±3.6 min, respectively). The apparent treatment difference in change in nebulizer weight likely reflected the different starting volumes of TSI and TOBI® formulations in the nebulizer (mean ±SD=1.86±0.53 g vs. 2.74±1.64 g, respectively).

Aerosol delivery findings indicate that it is possible to achieve comparable serum and sputum levels of tobramycin to the 300 mg TOBI® formulation by using the 420 mg TSI formulation. Current findings also indicate that the reduced nebulization times during administration of the 420 mg TSI treatment did not change the pharmacokinetics of tobramycin relative to the marketed 300 mg TOBI® formulation.

While the preferred embodiments of the invention have been illustrated and described, it will be appreciated that various changes can be made therein without departing from the spirit and scope of the invention.

The embodiments of the invention in which an exclusive property or privilege is claimed are defined as follows:

1. A method of the treatment of a cystic fibrosis patient having an endobronchial *Pseudomonas aeruginosa* infection comprising administering to the patient for inhalation a nebulized unit dose of 3.5 ml or less of an aqueous solution comprising an amount of tobramycin in a physiologically acceptable carrier effective to treat the *Pseudomonas aeruginosa* infection in the endobronchial space of the patient, for a duration of nebulization less than about 10 minutes, using a piezoelectric oscillator inhalation device having a rate of aerosol output of not less than about 4 μl/sec, that releases at least about 75% of the loaded dose, and that produces aerosol particles having particle sizes between about 1 μm to about 5 μm.

2. A method of claim 1 wherein the dose comprises 2.0 ml or less of the nebulized aerosol formulation.

3. A method of claim 1 wherein the dose comprises 1.5 ml or less of the nebulized aerosol formulation.

4. A method of claim 1 wherein the aerosol formulation comprises from about 80 to about 180 mg/ml of tobramycin.

5. A method of claim 1 wherein the aerosol formulation comprises from about 90 to about 150 mg/ml of tobramycin.

6. A method of claim 1 wherein the duration of nebulization is less that about 8 minutes.

7. A method of claim 1 wherein the duration of nebulization is less that about 6 minutes.

8. A method of claim 1 wherein the inhalation device has a rate of aerosol output of not less than about 5 µl/sec.

9. A method of claim 1 wherein the inhalation device has a rate of aerosol output of not less than about 8 µl/sec.

10. A method of claim 1 wherein the inhalation device releases at least about 80% of the loaded dose.

11. A method of claim 1 wherein the inhalation device releases at least about 85% of the loaded dose.

12. A method of claim 1 wherein the aerosol formulation comprises from about 60 to about 200 mg/ml of tobramycin.

13. A method of claim 12 wherein the aerosol formulation comprises from about 60 to about 150 mg/ml of tobramycin.

14. A method of claim 12 wherein the aerosol formulation comprises from about 60 to about 120 mg/ml of tobramycin.

15. A method of claim 12 wherein the aerosol formulation comprises from about 90 to about 150 mg/ml of tobramycin.

16. A method of claim 12 wherein the aerosol formulation comprises from about 90 to about 120 mg/ml of tobramycin.

\* \* \* \* \*